US010301627B2

(12) United States Patent
Bennett et al.

(10) Patent No.: US 10,301,627 B2
(45) Date of Patent: May 28, 2019

(54) TARGETING MICRORNAS FOR THE TREATMENT OF LIVER CANCER

(71) Applicants: Regulus Therapeutics Inc., San Diego, CA (US); Rosetta Genomics Ltd., Rehovot (IL)

(72) Inventors: C. Frank Bennett, Carlsbad, CA (US); Ayelet Chajut, Rehovot (IL); Christine Esau, La Jolla, CA (US); Eric Marcusson, San Francisco, CA (US); Noga Yerushalmi, Rehovot (IL)

(73) Assignees: Regulus Therapeutics Inc., San Diego, CA (US); Rosetta Genomics Ltd., Rehovot (IL)

( * ) Notice: Subject to any disclaimer, the term of this patent is extended or adjusted under 35 U.S.C. 154(b) by 0 days.

(21) Appl. No.: 15/813,584

(22) Filed: Nov. 15, 2017

(65) Prior Publication Data

US 2018/0127755 A1   May 10, 2018

Related U.S. Application Data

(62) Division of application No. 15/334,422, filed on Oct. 26, 2016, now Pat. No. 9,845,470, which is a division of application No. 14/833,889, filed on Aug. 24, 2015, now Pat. No. 9,506,062, which is a division of application No. 14/168,812, filed on Jan. 30, 2014, now Pat. No. 9,150,857, which is a division of application No. 13/481,105, filed on May 25, 2012, now Pat. No. 8,680,067, which is a division of application No. 12/740,211, filed as application No. PCT/US2008/081645 on Oct. 29, 2008, now Pat. No. 8,211,867.

(60) Provisional application No. 60/983,231, filed on Oct. 29, 2007.

(51) Int. Cl.

| C12N 15/113 | (2010.01) |
| A61K 31/7105 | (2006.01) |
| A61K 31/7088 | (2006.01) |
| A61K 45/06 | (2006.01) |
| A61K 31/407 | (2006.01) |
| A61K 31/44 | (2006.01) |
| A61K 31/4745 | (2006.01) |
| A61K 31/513 | (2006.01) |
| A61K 31/555 | (2006.01) |
| A61K 31/704 | (2006.01) |
| A61K 31/7048 | (2006.01) |
| A61K 31/7068 | (2006.01) |

(52) U.S. Cl.
CPC .......... *C12N 15/113* (2013.01); *A61K 31/407* (2013.01); *A61K 31/44* (2013.01); *A61K 31/4745* (2013.01); *A61K 31/513* (2013.01); *A61K 31/555* (2013.01); *A61K 31/704* (2013.01); *A61K 31/7048* (2013.01); *A61K 31/7068* (2013.01); *A61K 31/7088* (2013.01); *A61K 31/7105* (2013.01); *A61K 45/06* (2013.01); *C12N 2310/113* (2013.01); *C12N 2310/141* (2013.01); *C12N 2310/315* (2013.01); *C12N 2310/321* (2013.01); *C12N 2310/3341* (2013.01); *C12N 2310/346* (2013.01)

(58) Field of Classification Search
CPC ................ A01K 2207/05; A61K 31/407; C12N 15/113; C12N 2310/113; C12N 2310/141; C12N 2310/315; C12N 2310/321

See application file for complete search history.

(56) References Cited

U.S. PATENT DOCUMENTS

| 7,683,036 B2 | 3/2010 | Esau et al. |
| 8,017,763 B2 | 9/2011 | Manoharan et al. |
| 8,084,199 B2 | 12/2011 | Croce et al. |
| 8,110,558 B2 | 2/2012 | Bennett et al. |
| 8,133,876 B2 | 3/2012 | Bennett et al. |
| 8,173,611 B2 | 5/2012 | Brown et al. |
| 8,211,867 B2 | 7/2012 | Bennett et al. |
| 8,680,067 B2 | 3/2014 | Bennett et al. |

(Continued)

FOREIGN PATENT DOCUMENTS

| CN | 1800388 | 7/2006 |
| EP | 1777301 A2 | 4/2007 |

(Continued)

OTHER PUBLICATIONS

Huang et al. Hepatology Research 39:786-794 (Year: 2009).*
Bi et al. PloS One, 7:e40169, pp. 1-11 (Year: 2012).*
Li et al. Int. J. Cancer 123, 1616-1622 (Year: 2008).*
Kong et al. Tumor Biol. 37:511-519 (Year: 2016).*
Chan et al., "MicroRNA-21 is an antiapoptotic factor in human glioblastoma cells" Cancer Research, American Association for Cancer Research, Baltimore, MD., US, Jul. 15, 2005, 65(14):6029-6033.

(Continued)

*Primary Examiner* — Brian Whiteman
(74) *Attorney, Agent, or Firm* — McNeill Baur PLLC

(57) ABSTRACT

Provided herein are methods for the treatment of liver cancer. These methods encompass the administration of a compound comprising a modified oligonucleotide, wherein the modified oligonucleotide is targeted to a miRNA. Also provided herein are compositions for the treatment of liver cancer. Such compositions include compounds comprising a modified oligonucleotide, wherein the modified oligonucleotide is targeted to a miRNA. Certain miRNAs have been identified as overexpressed in liver cancer, such as, for example, hepatocellular carcinoma, and are thus selected for targeting by modified oligonucleotides. Further, certain miRNAs have been identified as overexpressed in hepatocellular carcinoma cells exposed to dioxin, and are thus selected for targeting by modified oligonucleotides. Antisense inhibition of certain of these miRNAs has been found to inhibit cell proliferation and induce apoptosis.

24 Claims, 9 Drawing Sheets

Specification includes a Sequence Listing.

(56) References Cited

U.S. PATENT DOCUMENTS

| | | | |
|---|---|---|---|
| 8,946,177 | B2 | 2/2015 | Brown et al. |
| 9,150,857 | B2 | 10/2015 | Bennett et al. |
| 9,506,062 | B2 | 11/2016 | Bennett et al. |
| 2005/0182005 | A1 | 8/2005 | Tuschl et al. |
| 2006/0019286 | A1 | 1/2006 | Horvitz et al. |
| 2006/0127891 | A1 | 6/2006 | McSwiggen et al. |
| 2007/0055448 | A1 | 3/2007 | Mendrick et al. |
| 2007/0065844 | A1 | 3/2007 | Golub et al. |
| 2009/0192102 | A1 | 7/2009 | Bader et al. |
| 2013/0143945 | A1 | 6/2013 | Brown et al. |
| 2013/0303591 | A1 | 11/2013 | Brown et al. |
| 2014/0031415 | A1 | 1/2014 | Brown et al. |

FOREIGN PATENT DOCUMENTS

| | | |
|---|---|---|
| JP | 2007-097429 | 4/2007 |
| WO | WO 2003/029459 | 4/2003 |
| WO | WO 2005/013901 | 2/2005 |
| WO | WO 2005/078139 A2 | 8/2005 |
| WO | WO 2005/118806 | 12/2005 |
| WO | WO 2006/111512 | 10/2006 |
| WO | WO 2007/073737 | 7/2007 |
| WO | WO 2007/090073 | 8/2007 |
| WO | WO 2007/095387 A2 | 8/2007 |
| WO | WO 2007/095614 | 8/2007 |
| WO | WO 2007/112753 A2 | 10/2007 |
| WO | WO 2008/025025 A2 | 2/2008 |
| WO | WO 2008/054828 A2 | 5/2008 |
| WO | WO 2009/043353 | 4/2009 |

OTHER PUBLICATIONS

Cheng et al, "Antisense inhibition of human miRNAs and indications for an involvement of miRNA in cell growth and apoptosis" Nucleic Acids Research, Mar. 1, 2005 33(4):1290-1297.

Database WPI Week 200721 Thomson Scientific, London, GB; AN 2007-200997 XP002550945-& CN 1 800 388 a (Radiology Inst Pla Military Medical Acad) Jul. 12, 2006; p. 1 (1 page).

Davis et al., "Improved targeting of miRNA with antisense oligonucleotides," Nucleic Acids Res, 2006, 34(8):2294-2304.

Decision on Suggestion to Declare Interference, dated Oct. 28, 2014, 2 pages.

English Abstract of JP 2007-097429, published Apr. 19, 2007 (1 page).

English abstract of CN1800388, published Jul. 12, 2006 (1 page).

Machine translation of CN1800388, published in Chinese Jul. 12, 2006, 24 pages.

Machine translation of CN1800388, published in Chinese Jul. 12, 2006, 10 pages.

Geary et al., "Pharmacokinetic Properties of 2'-O-(2-Methoxyethyl)-Modified Oligonucleotide Analogs in Rats," JPET, 2001, 296:8890-8897.

Gramantieri et al., "Cyclin G1 is a target of miR-122a, a microRNA frequently down-regulated in human hepatocellular carcinoma," Cancer Res. 2007,67(13):6092-6099.

International Preliminary Report on Patentability dated May 4, 2010, for Application No. PCT/US2008/081645, filed Oct. 29, 2008 (7 pages).

Iyoda et al., "Involvement of the p38 Mitogen-Activated Protein Kinase Cascade in Hepatocellular Carcinoma," Cancer 2003, 97: 3017-3026.

Kutay et al., "Downregulation of miR-122 in the Rodent and Human Hepatocellular Carcinomas," J. Cell. Biochem., Oct. 15, 2006; 99(3): 671-678.

Liebman et al., "Des-gamma-carboxy (abnormal) prothrombin as a serum marker of primary hepatocellular carcinoma," N Engl J Med., 1984, 310:1427-1431 (Abstract), 1 page.

Manoharan, "Oligonucleotide Conjugates as Potential Antisense Drugs with Improved Uptake, Biodistribution, Targeted Delivery, and Mechanism of Action," Antisense & Nucleic Acid Drug Development, 2002, 12:103-128.

Meng et al., "Involvement of Human Micro-RNA in Growth and Response to Chemotherapy in Human Cholangiocarcinoma Cell Lines," Gastroenterology, 2006, 130:2113-2129.

Meng et al., "MicroRNA-21 regulates expression of the PTEN tumor suppressor gene in human hepatocellular cancer" Gastroenterology, May 21, 2007 133(2):647-658.

The Merck Manual of Diagnosis and Therapy, 2006, 18th edition, Merck Research Laboratories, Whitehouse Station, NJ, 3 pages.

Moffat et al., "MicroRNAs in Adult Liver are Refractory to Dioxin Treatment" Toxicological Sciences, Aug. 13, 2007 (Aug. 13, 2007), 99(2):470-487.

Murakami et al., "Comprehensive analysis of microRNA expression patterns in hepatocellular carcinoma and non-tumorous tissues," Oncogene, 2006, 25(17):2537-45.

National Cancer Institute Fact Sheet on Metastatic Cancer, http://www.cancer.gov/cancertopics/factsheet/Sites-Types/metastatic, retrieved May 23, 2011, 5 pages.

Si et al., "miR-21-mediated tumor growth," Oncogene; 2007; 26: 2799-2803.

Suggestion to Declare Interference, filed May 3, 2013, in U.S. Appl. No. 13/299,255, 8 pages.

Supplemental Submission Further to Suggestion to Declare Interference and Declaration of Dr. Sinil Kim, filed Jul. 1, 2013, in U.S. Appl. No. 13/299,255, 5 pages.

U.S. Appl. No. 60/627,171, filed Nov. 12, 2004, David Lance et al., 376 pages.

Volinia et al., "A microRNA expression signature of human solid tumors defines cancer gene targets," Proc Natl Acad Sci U S A; 2006; 103(7): 2257-2261.

Wong et al. "Frequent up-regulations of miR-222 in hepatitis-B related heptacellular carcinoma," Proceedings of the American Association for Cancer Research Annual Meeting, Apr. 2007, 48:1072.

Wong et al., "Quantitative comparison of alpha-fetoprotein and albumin mRNA levels in hepatocellular carcinoma/adenoma, non-tumor liver and blood: implications in cancer detection and monitoring," Cancer Lett, 2000, 156:141-149 (Abstract) 1 page.

Yuan et al., "Measurement of des-gamma-caroxy prothrombin levels in cancer and non-cancer tissue in patients with hepatocellular carcinoma," Oncology Reports, 2004, 12:269-273 (Abstract) 1 page.

Applicant's arguments in U.S. Appl. No. 12/488,394, filed Jun. 19, 2009, pp. 1-15.

File History of U.S. Appl. No. 12/740,211, filed Apr. 28, 2010.
File History of U.S. Appl. No. 13/481,105, filed May 25, 2012.
File History of U.S. Appl. No. 14/168,812, filed Jan. 30, 2014.
File History of U.S. Appl. No. 14/833,889, filed Aug. 24, 2015.
File History of U.S. Appl. No. 15/334,422, filed Oct. 26, 2016.

* cited by examiner

SEQUENCE LISTING

```
<160> NUMBER OF SEQ ID NOS: 40

<210> SEQ ID NO 1
<211> LENGTH: 72
<212> TYPE: RNA
<213> ORGANISM: Homo sapiens

<400> SEQUENCE: 1
ugucggguag cuuaucagac ugauguugac uguugaaucu cauggcaaca ccagucgaug     60
ggcugucuga ca                                                         72

<210> SEQ ID NO 2
<211> LENGTH: 86
<212> TYPE: RNA
<213> ORGANISM: Homo sapiens

<400> SEQUENCE: 2
ugccagucuc uaggucccug agacccuuua accugugagg acauccaggg ucacagguga     60
gguucuuggg agccuggcgu cuggcc                                          86

<210> SEQ ID NO 3
<211> LENGTH: 92
<212> TYPE: RNA
<213> ORGANISM: Homo sapiens

<400> SEQUENCE: 3
cggcuggaca gcgggcaacg gaaucccaaa agcagcuguu gucuccagag cauuccagcu     60
gcgcuuggau uucguccccu gcucuccugc cu                                   92

<210> SEQ ID NO 4
<211> LENGTH: 110
<212> TYPE: RNA
<213> ORGANISM: Homo sapiens

<400> SEQUENCE: 4
acccggcagu gccuccaggc gcagggcagc cccugcccac cgcacacugc gcugcccag      60
```

```
acccacugug cgugugacag cggcugaucu gugccugggc agcgcgaccc        110
```

<210> SEQ ID NO 5
<211> LENGTH: 110
<212> TYPE: RNA
<213> ORGANISM: Homo sapiens

<400> SEQUENCE: 5

```
gcugcuggaa gguguaggua cccucaaugg cucaguagcc aguguagauc cugucuuucg    60
uaaucagcag cuacaucugg cuacuggguc ucgauggca ucuucuagcu                110
```

<210> SEQ ID NO 6
<211> LENGTH: 66
<212> TYPE: RNA
<213> ORGANISM: Homo sapiens

<400> SEQUENCE: 6

```
agggcuccug acuccagguc cuguguguua ccuagaaaua gcacuggacu uggagucaga    60
aggccu                                                              66
```

<210> SEQ ID NO 7
<211> LENGTH: 94
<212> TYPE: RNA
<213> ORGANISM: Homo sapiens

<400> SEQUENCE: 7

```
auaaaggaag uuaggcugag gggcagagag cgagacuuuu cuauuuucca aaagcucggu    60
cugaggcccc ucagucuugc uuccuaaccc gcgc                                94
```

<210> SEQ ID NO 8
<211> LENGTH: 100
<212> TYPE: RNA
<213> ORGANISM: Homo sapiens

<400> SEQUENCE: 8

```
gugagcgggc gcggcaggga ucgcgggcgg guggcggccu agggcgcgga gggcggaccg    60
ggaauggcgc gccgugcgcc gccggcguaa cugcggcgcu                          100
```

<210> SEQ ID NO 9
<211> LENGTH: 22
<212> TYPE: RNA
<213> ORGANISM: Homo sapiens

<400> SEQUENCE: 9

```
uagcuuauca gacugauguu ga                                            22
```

<210> SEQ ID NO 10
<211> LENGTH: 24
<212> TYPE: RNA
<213> ORGANISM: Homo sapiens

<400> SEQUENCE: 10

```
ucccugagac ccuuuaaccu guga                                          24
```

<210> SEQ ID NO 11
<211> LENGTH: 23
<212> TYPE: RNA
<213> ORGANISM: Homo sapiens

<400> SEQUENCE: 11

```
caacggaauc ccaaaagcag cug                                           23
```

```
<210> SEQ ID NO 12
<211> LENGTH: 22
<212> TYPE: RNA
<213> ORGANISM: Homo sapiens

<400> SEQUENCE: 12
cugugcgugu gacagcggcu ga                                               22

<210> SEQ ID NO 13
<211> LENGTH: 21
<212> TYPE: RNA
<213> ORGANISM: Homo sapiens

<400> SEQUENCE: 13
agcuacaucu ggcuacuggg u                                                21

<210> SEQ ID NO 14
<211> LENGTH: 21
<212> TYPE: RNA
<213> ORGANISM: Homo sapiens

<400> SEQUENCE: 14
acuggacuug gagucagaag g                                                21

<210> SEQ ID NO 15
<211> LENGTH: 23
<212> TYPE: RNA
<213> ORGANISM: Homo sapiens

<400> SEQUENCE: 15
agcucggucu gaggccccuc agu                                              23

<210> SEQ ID NO 16
<211> LENGTH: 25
<212> TYPE: RNA
<213> ORGANISM: Homo sapiens

<400> SEQUENCE: 16
agggaucgcg ggcgguggc ggccu                                             25

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
tcaacatcag tctgataagc ta                                               22

<210> SEQ ID NO 18
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 18
cacaggttaa agggtctcag gga                                              23

<210> SEQ ID NO 19
<211> LENGTH: 24
<212> TYPE: DNA
```

```
<213> ORGANISM: Artificial Sequence
<220> FEATURE:
<223> OTHER INFORMATION: Synthetic Oligonucleotide

<400> SEQUENCE: 19
tcacaggtta aagggtctca ggga                                              24

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 20
agctgctttt gggattccgt tg                                                22

<210> SEQ ID NO 21
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 21
cagctgcttt tgggattccg ttg                                               23

<210> SEQ ID NO 22
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 22
tcagccgctg tcacacgcac ag                                                22

<210> SEQ ID NO 23
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 23
gagacccagt agccagatgt agct                                              24

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
acccagtagc cagatgtagc t                                                 21

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
ccttctgact ccaagtccag                                                   20
```

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 26
ggccttctga ctccaagtcc ag                                              22

<210> SEQ ID NO 27
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 27
ccttctgact ccaagtccag t                                               21

<210> SEQ ID NO 28
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 28
ctgaggggcc tcagaccgag ct                                              22

<210> SEQ ID NO 29
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 29
tctgaggggc tcagaccga gct                                              23

<210> SEQ ID NO 30
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 30
aggccgccac ccgcccgcga tccct                                           25

<210> SEQ ID NO 31
<211> LENGTH: 23
<212> TYPE: RNA
<213> ORGANISM: Homo sapiens

<400> SEQUENCE: 31
aacauucaac gcugucggug agu                                             23

<210> SEQ ID NO 32
<211> LENGTH: 22
<212> TYPE: RNA
<213> ORGANISM: Homo sapiens

<400> SEQUENCE: 32
accaucgacc guugauugua cc                                                22

<210> SEQ ID NO 33
<211> LENGTH: 23
<212> TYPE: RNA
<213> ORGANISM: Homo sapiens

<400> SEQUENCE: 33
aacauucauu gcugucggug ggu                                               23

<210> SEQ ID NO 34
<211> LENGTH: 110
<212> TYPE: RNA
<213> ORGANISM: Homo sapiens

<400> SEQUENCE: 34
ugaguuuuga gguugcuuca gugaacauuc aacgcugucg gugaguuugg aauuaaaauc       60
aaaaccaucg accguugauu gucccuaug gcuaaccauc aucuacucca                  110

<210> SEQ ID NO 35
<211> LENGTH: 110
<212> TYPE: RNA
<213> ORGANISM: Homo sapiens

<400> SEQUENCE: 35
agaagggcua ucaggccagc uucagagga cuccaaggaa cauucaacgc ugucggugag        60
uuugggauuu gaaaaaacca cugaccguug acuguaccuu ggggguccuua                110

<210> SEQ ID NO 36
<211> LENGTH: 110
<212> TYPE: RNA
<213> ORGANISM: Homo sapiens

<400> SEQUENCE: 36
ccugugcaga gauuauuuuu uaaaagguca caaucaacau ucauugcugu cgguggguug       60
aacugugugg acaagcucac ugaacaauga augcaacugu ggccccgcuu                 110

<210> SEQ ID NO 37
<211> LENGTH: 89
<212> TYPE: RNA
<213> ORGANISM: Homo sapiens

<400> SEQUENCE: 37
cugauggcug cacucaacau ucauugcugu cggggguuu gagucugaau caacucacug        60
aucaaugaau gcaaacugcg gaccaaaca                                         89

<210> SEQ ID NO 38
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 38
actcaccgac agcgttgaat gtt                                               23

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide

```
<400> SEQUENCE: 39
ggtacaatca acggtcgatg gt                                              22

<210> SEQ ID NO 40
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 40
acccaccgac agcaatgaat gtt                                             23
```

US 10,301,627 B2

TARGETING MICRORNAS FOR THE TREATMENT OF LIVER CANCER

CROSS REFERENCE TO RELATED APPLICATIONS

The present application is a divisional of U.S. patent application Ser. No. 15/334,422, filed Oct. 26, 2016, which is a divisional of U.S. patent application Ser. No. 14/833,889, filed Aug. 24, 2015, now U.S. Pat. No. 9,506,062, which is a divisional of U.S. patent application Ser. No. 14/168,812, filed Jan. 30, 2014, now U.S. Pat. No. 9,150,857, which is a divisional of U.S. patent application Ser. No. 13/481,105, filed May 25, 2012, now U.S. Pat. No. 8,680,067, which is a divisional of U.S. patent application Ser. No. 12/740,211, filed Apr. 28, 2010, now U.S. Pat. No. 8,211,867, which is a § 371 national entry of International Application No. PCT/US2008/081645, filed Oct. 29, 2008, which claims priority under 35 U.S.C. § 119(e) to U.S. Provisional Application No. 60/983,231, filed Oct. 29, 2007, each of which is incorporated by reference herein in its entirety for any purpose.

INCORPORATION OF SEQUENCE LISTING

The present application is filed with a Sequence Listing in electronic format. The Sequence Listing is provided as a file entitled "2015-08-24_01138-0003-03US_Sequence_Listing_ST25.txt" created on Aug. 6, 2015, which is 8,147 bytes in size. The information in the electronic format of the sequence listing is incorporated herein by reference in its entirety.

FIELD OF INVENTION

Provided herein are methods and compositions for the treatment of liver cancer, including but not limited to hepatocellular carcinoma. Provided herein are also methods and compositions for the treatment of dioxin induced liver cancer, including but not limited to dioxin induced hepatocellular carcinoma. Such methods comprise administering a compound comprising a modified oligonucleotide targeted to a miRNA.

DESCRIPTION OF RELATED ART

MicroRNAs (miRNAs), also known as "mature miRNA" are small (approximately 18-24 nucleotides in length), non-coding RNA molecules encoded in the genomes of plants and animals. In certain instances, highly conserved, endogenously expressed miRNAs regulate the expression of genes by binding to the 3'-untranslated regions (3'-UTR) of specific mRNAs. More than 1000 different miRNAs have been identified in plants and animals certain mature miRNAs appear to originate from long endogenous primary miRNA transcripts (also known as pri-miRNAs, pri-mirs, pri-miRs or pri-pre-miRNAs) that are often hundreds of nucleotides in length (Lee, et al., EMBO J., 2002, 21(17), 4663-4670).

Functional analyses of miRNAs have revealed that these small non-coding RNAs contribute to different physiological processes in animals, including developmental timing, organogenesis, differentiation, patterning, embryogenesis, growth control and programmed cell death. Examples of particular processes in which miRNAs participate include stem cell differentiation, neurogenesis, angiogenesis, hematopoiesis, and exocytosis (reviewed by Alvarez-Garcia and Miska, Development, 2005, 132, 4653-4662). In some instances, miRNAs are thought to exercise post-transcriptional control in most eukaryotic organisms and have been detected in plants and animals as well as certain viruses.

Families of miRNAs can be characterized by nucleotide identity at positions 2-8 of the miRNA, a region known as the seed sequence. Lewis et al. describe several miRNA families, as well as miRNA superfamilies, which are characterized by related seed sequences (Lewis et al. Cell. 2005, 120(1):15-20).

SUMMARY OF INVENTION

In certain embodiments, the present invention provides methods for treating liver cancer, comprising administering to a subject in need thereof a compound comprising a modified oligonucleotide consisting of 15 to 30 linked nucleosides, wherein the modified oligonucleotide has a nucleobase sequence that is complementary to a nucleobase sequence selected from SEQ ID NO: 1, 2, 3, 4, 5, 6, 7, and 8; or to a sequence at least 80% identical thereto.

In certain embodiments, the present invention provides methods for treating liver cancer, comprising administering to the subject in need thereof a compound comprising a modified oligonucleotide consisting of 15 to 30 linked nucleosides and having a nucleobase sequence that is complementary to a nucleobase sequence selected from SEQ ID NOs: 9, 10, 11, 12, 13, 14, 15, and 16; or to a nucleobase sequence at least 80% identical thereto.

In certain embodiments, the present invention provides methods for treating liver cancer, comprising administering to a subject in need thereof a compound comprising a modified oligonucleotide consisting of 15 to 30 linked nucleosides, wherein the modified oligonucleotide has a nucleobase sequence comprising at least 15 contiguous nucleobases of a nucleobase sequence selected from among the nucleobase sequences recited in SEQ ID NOs 17, 18, 19, 20, 21, 22, 23, 24, 25, 26, 27, 28, 29, and 30; or a sequence at least 80% identical thereto.

In certain embodiments, the present invention provides methods for treating liver cancer, comprising administering to a subject in need thereof a pharmaceutical composition comprising a modified oligonucleotide consisting of 15 to 30 linked nucleosides, wherein the modified oligonucleotide has a nucleobase sequence that is complementary to a nucleobase sequence selected from SEQ ID NO: 1, 2, 3, 4, 5, 6, 7, and 8; or to a sequence at least 80% identical thereto.

In certain embodiments, the present invention provides methods for treating liver cancer, comprising administering to the subject in need thereof a pharmaceutical composition comprising a modified oligonucleotide consisting of 15 to 30 linked nucleosides and having a nucleobase sequence that is complementary to a nucleobase sequence selected from SEQ ID NOs: 9, 10, 11, 12, 13, 14, 15, and 16; or to a nucleobase sequence at least 80% identical thereto.

In certain embodiments, the present invention provides methods for treating liver cancer, comprising administering to a subject in need thereof a pharmaceutical composition comprising a modified oligonucleotide consisting of 15 to 30 linked nucleosides, wherein the modified oligonucleotide has a nucleobase sequence comprising at least 15 contiguous nucleobases of a nucleobase sequence selected from among the nucleobase sequences recited in SEQ ID NOs 17, 18, 19, 20, 21, 22, 23, 24, 25, 26, 27, 28, 29, and 30; or a sequence at least 80% identical thereto.

In certain embodiments, the present invention provides a compound comprising a modified oligonucleotide consisting of 15 to 30 linked nucleosides, wherein the modified oligonucleotide has a nucleobase sequence that is complementary to a nucleobase sequence selected from SEQ ID NO: 1, 2, 3, 4, 5, 6, 7, and 8; or to a sequence at least 80% identical thereto, for use in treating liver cancer.

In certain embodiments, the present invention provides a compound comprising a modified oligonucleotide consisting of 15 to 30 linked nucleosides, wherein the modified oligonucleotide has a nucleobase sequence that is complementary to a nucleobase sequence selected from SEQ ID NO: 9, 10, 11, 12, 13, 14, 15, and 16; or to a sequence at least 80% identical thereto, for use in treating liver cancer.

In certain embodiments, the present invention provides a compound comprising a modified oligonucleotide consisting of 15 to 30 linked nucleosides, wherein the modified oligonucleotide has a nucleobase sequence comprising at least 15 contiguous nucleobases of a nucleobase sequence selected from among the nucleobase sequences recited in SEQ ID NOs 17, 18, 19, 20, 21, 22, 23, 24, 25, 26, 27, 28, 29, and 30; or to a sequence at least 80% identical thereto, for use in treating liver cancer.

In certain embodiments, the invention provides methods for treating a dioxin induced liver cancer comprising administering to a subject in need thereof a compound comprising a modified oligonucleotide consisting of 15 to 30 linked nucleosides, wherein the modified oligonucleotide has a nucleobase sequence that is complementary to a sequence selected from SEQ ID NO: 31, 32, 33, 34, 35, 36, and 37; or to a sequence at least about 80% identical thereto.

In certain embodiments, the invention provides a compound comprising a modified oligonucleotide consisting of 15 to 30 linked nucleosides, wherein the modified oligonucleotide has a nucleobase sequence that is complementary to a sequence selected from SEQ ID NO: 31, 32, 33, 34, 35, 36, and 37; or to a sequence at least about 80% identical thereto, for use in treating a dioxin induced liver cancer.

In certain embodiments, the invention provides methods for treating a dioxin induced liver cancer comprising administering to a subject in need thereof a compound comprising a modified oligonucleotide consisting of 15 to 30 linked nucleosides, wherein the modified oligonucleotide has a nucleobase sequence comprising at least 15 contiguous nucleobases of a nucleobase sequence selected from among the nucleobase sequences recited in SEQ ID NOs 38, 39, and 40; or to a sequence at least about 80% identical thereto.

In certain embodiments, the invention provides a compound comprising a modified oligonucleotide consisting of 15 to 30 linked nucleosides, wherein the modified oligonucleotide has a nucleobase sequence comprising at least 15 contiguous nucleobases of a nucleobase sequence selected from among the nucleobase sequences recited in SEQ ID NOs 38, 39, and 40; or to a sequence at least about 80% identical thereto, for use in treating a dioxin induced liver cancer.

In certain embodiments, the dioxin induced liver cancer is hepatocellular carcinoma.

In certain embodiments, the present invention provides a compound comprising a modified oligonucleotide consisting of 15 to 30 linked nucleosides and having a nucleobase sequence that is complementary to a nucleobase sequence selected from SEQ ID NO: 1, 2, 3, 4, 5, 6, 7, and 8; or to a sequence at least about 80% identical thereto.

In certain embodiments, the present invention provides a compound comprising a modified oligonucleotide consisting of 15 to 30 linked nucleosides and having a nucleobase sequence that is complementary to a nucleobase sequence selected from SEQ ID NO: 1, 2, 3, 4, 5, 6, 7, and 8; or to a sequence at least about 80% identical thereto, for use in treating liver cancer.

In certain embodiments, the present invention provides a compound comprising a modified oligonucleotide consisting of 15 to 30 linked nucleosides and having a nucleobase sequence that is complementary to a nucleobase sequence selected from SEQ ID NOs: 9, 10, 11, 12, 13, 14, 15, and 16; or to a sequence at least about 80% identical thereto.

In certain embodiments, the present invention provides a compound comprising a modified oligonucleotide consisting of 15 to 30 linked nucleosides and having a nucleobase sequence that is complementary to a nucleobase sequence selected from SEQ ID NOs: 9, 10, 11, 12, 13, 14, 15, and 16; or to a sequence at least about 80% identical thereto, for use in treating liver cancer.

In certain embodiments, the present invention provides a compound comprising a modified oligonucleotide consisting of 15 to 30 linked nucleosides and having a nucleobase sequence comprising at least 15 contiguous nucleobases of a nucleobase sequence selected from among the nucleobase sequences recited in SEQ ID NOs 17, 18, 19, 20, 21, 22, 23, 24, 25, 26, 27, 28, 29, and 30.

In certain embodiments, the present invention provides a compound comprising a modified oligonucleotide consisting of 15 to 30 linked nucleosides and having a nucleobase sequence comprising at least 15 contiguous nucleobases of a nucleobase sequence selected from among the nucleobase sequences recited in SEQ ID NOs 17, 18, 19, 20, 21, 22, 23, 24, 25, 26, 27, 28, 29, and 30, for use in treating liver cancer.

In certain embodiments, the present invention provides a compound comprising a modified oligonucleotide consisting of 15 to 30 linked nucleosides and having a nucleobase sequence comprising at least 15 contiguous nucleobases of a nucleobase sequence selected from among the nucleobase sequences recited in SEQ ID NOs 38, 39, and 40, for use in treating liver cancer.

In certain embodiments, the present invention provides a pharmaceutical composition comprising a modified oligonucleotide of the invention or a salt thereof and a pharmaceutically acceptable carrier or diluent.

In certain embodiments, the compound consists of a modified oligonucleotide.

In certain embodiments, the modified oligonucleotide consists of 15, 16, 17, 18, 19, 20, 21, 22, 23, 24, or 25 linked nucleosides.

In certain embodiments, the nucleobase sequence of the modified oligonucleotide has no more than two mismatches to a nucleobase sequence selected from SEQ ID NO: 1, 2, 3, 4, 5, 6, 7, and 8. In certain embodiments, the nucleobase sequence of the modified oligonucleotide has no more than one mismatch to a nucleobase sequence selected from SEQ ID NO: 1, 2, 3, 4, 5, 6, 7, and 8. In certain embodiments, the nucleobase sequence of the modified oligonucleotide has one mismatch to a nucleobase sequence selected from SEQ ID NO: 1, 2, 3, 4, 5, 6, 7, and 8. In certain embodiments, the nucleobase sequence of the modified oligonucleotide has no mismatches to a nucleobase sequence selected from SEQ ID NO: 1, 2, 3, 4, 5, 6, 7, and 8.

In certain embodiments, the nucleobase sequence of the modified oligonucleotide has no more than two mismatches to a nucleobase sequence selected from SEQ ID NOs: 9, 10, 11, 12, 13, 14, 15, and 16. In certain embodiments, the nucleobase sequence of the modified oligonucleotide has no more than one mismatch to a nucleobase sequence selected from SEQ ID NOs: 9, 10, 11, 12, 13, 14, 15, and 16. In certain embodiments, the nucleobase sequence of the modified oligonucleotide has one mismatch to a nucleobase sequence selected from SEQ ID NOs: 9, 10, 11, 12, 13, 14, 15, and 16. In certain embodiments, the nucleobase sequence of the modified oligonucleotide has no mismatches to a nucleobase sequence selected from SEQ ID NOs: 9, 10, 11, 12, 13, 14, 15, and 16.

In certain embodiments, the nucleobase sequence of the modified oligonucleotide has no more than two mismatches to a nucleobase sequence selected from SEQ ID NOs: 31, 32, 33, 34, 35, 36, and 37. In certain embodiments, the nucleobase sequence of the modified oligonucleotide has no more than one mismatch to a nucleobase sequence selected from SEQ ID NOs: 31, 32, 33, 34, 35, 36, and 37. In certain embodiments, the nucleobase sequence of the modified oligonucleotide has one mismatch to a nucleobase sequence selected from SEQ ID NOs: 31, 32, 33, 34, 35, 36, and 37. In certain embodiments, the nucleobase sequence of the modified oligonucleotide has no mismatches to a nucleobase sequence selected from SEQ ID NOs: 31, 32, 33, 34, 35, 36, and 37.

In certain embodiments, the modified oligonucleotide has a nucleobase sequence comprising at least 16 contiguous nucleobases of a nucleobase sequence selected from among the nucleobase sequences recited in SEQ ID NOs 17, 18, 19, 20, 21, 22, 23, 24, 25, 26, 27, 28, 29, and 30.

In certain embodiments, the modified oligonucleotide has a nucleobase sequence comprising at least 17 contiguous nucleobases of a nucleobase sequence selected from among the nucleobase sequences recited in SEQ ID NOs 17, 18, 19, 20, 21, 22, 23, 24, 25, 26, 27, 28, 29, and 30.

In certain embodiments, the modified oligonucleotide has a nucleobase sequence comprising at least 18 contiguous nucleobases of a nucleobase sequence selected from among the nucleobase sequences recited in SEQ ID NOs 17, 18, 19, 20, 21, 22, 23, 24, 25, 26, 27, 28, 29, and 30.

In certain embodiments, the modified oligonucleotide has a nucleobase sequence comprising at least 19 contiguous nucleobases of a nucleobase sequence selected from among the nucleobase sequences recited in SEQ ID NOs 17, 18, 19, 20, 21, 22, 23, 24, 25, 26, 27, 28, 29, and 30.

In certain embodiments, the modified oligonucleotide has a nucleobase sequence comprising at least 20 contiguous nucleobases of a nucleobase sequence selected from among the nucleobase sequences recited in SEQ ID NOs 17, 18, 19, 20, 21, 22, 23, 24, 25, 26, 27, 28, 29, and 30.

In certain embodiments, the modified oligonucleotide has a nucleobase sequence comprising at least 21 contiguous nucleobases of a nucleobase sequence selected from among the nucleobase sequences recited in SEQ ID NOs 17, 18, 19, 20, 21, 22, 23, 24, 25, 26, 27, 28, 29, and 30.

In certain embodiments, the modified oligonucleotide has a nucleobase sequence comprising at least 22 contiguous nucleobases of a nucleobase sequence selected from among the nucleobase sequences recited in SEQ ID NOs 17, 18, 19, 20, 21, 22, 23, 24, 25, 26, 27, 28, 29, and 30.

In certain embodiments, the modified oligonucleotide has a nucleobase sequence comprising at least 23 contiguous nucleobases of a nucleobase sequence selected from among the nucleobase sequences recited in SEQ ID NOs 17, 18, 19, 20, 21, 22, 23, 24, 25, 26, 27, 28, 29, and 30.

In certain embodiments, the modified oligonucleotide has a nucleobase sequence consisting of a nucleobase sequence selected from among the nucleobase sequences recited in SEQ ID NOs 17, 18, 19, 20, 21, 22, 23, 24, 25, 26, 27, 28, 29, and 30.

In certain embodiments, the modified oligonucleotide has a nucleobase sequence comprising at least 16, at least 17, at least 18, at least 19, at least 20, at least 21, at least 22, or at least 23 contiguous nucleobases of a nucleobase sequence from among the nucleobase sequences recited in SEQ ID Nos 38, 39, and 40.

In certain embodiments, the modified oligonucleotide comprises one or more modified sugars, internucleoside linkages, or nucleobases. In certain embodiments, at least one internucleoside linkage is a modified internucleoside linkage. For example, at least one internucleoside linkage may be a phosphorothioate internucleoside linkage. In certain embodiments, each internucleoside linkage is a modified internucleoside linkage. For example, each internucleoside linkage may be a phosphorothioate internucleoside linkage.

In certain embodiments, at least one nucleoside of the modified oligonucleotide comprises a modified sugar. In certain embodiments, each of a plurality of nucleosides comprises a modified sugar. In certain embodiments, each nucleoside of the modified oligonucleotide comprises a modified sugar. In each of these embodiments, the modified sugar may be a 2'-O-methoxyethyl sugar, a 2'-fluoro sugar, a 2'-O-methyl sugar, or a bicyclic sugar moiety. In certain embodiments, each of a plurality of nucleosides comprises a 2'-O-methoxyethyl sugar and each of a plurality of nucleosides comprises a 2'-fluoro sugar.

In certain embodiments, the modified oligonucleotide comprises at least one modified nucleobase. In certain such embodiments, the modified nucleobase is a 5-methylcytosine. In certain embodiments, at least one nucleoside comprises a cytosine, wherein the cytosine is a 5-methylcytosine. In certain such embodiments, each cytosine is a 5-methylcytosine.

In certain embodiments, the liver cancer is hepatocellular carcinoma. In certain embodiments, the subject is a human. In certain embodiments, the hepatocellular carcinoma is dioxin-induced.

In certain embodiments, administration of a compound of the invention comprises intravenous administration, subcutaneous administration, intratumoral administration, or chemoembolization.

In certain embodiments, the methods of the present invention further comprise administering at least one additional therapy. The additional therapy may be a chemotherapeutic agent. The chemotherapeutic agent may be selected from 5-fluorouracil, gemcitabine, doxorubicine, mitomycin c, sorafenib, etoposide, carboplatin, epirubicin, irinotecan and oxaliplatin. The additional therapy may be administered at the same time, less frequently, or more frequently than a compound or pharmaceutical composition of the invention.

In certain embodiments, the modified oligonucleotide is administered at a dose selected from 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, and 800 mg. The modified oligonucleotide may be administered one per day, once per week, once per two weeks, once per three weeks, or once per four weeks.

In certain embodiments, the administration of a compound of the invention results in reduction of liver tumor size and/or liver tumor number. In certain embodiments, the administration of a compound of the invention prevents an increase in tumor size and/or tumor number. In certain embodiments, the administration of a compound of the invention prevents, slows, and/or stops metastatic progression. In certain embodiments, the administration of a compound of the invention extends the overall survival time of the subject. In certain embodiments, the administration of a compound of the invention extends the progression-free survival of the subject. In certain embodiments, administration of a compound of the invention prevents the recurrence of liver tumors. In certain embodiments, administration of a compound of the invention prevents recurrence of liver tumor metastasis. In certain embodiments, administration of a compound of the invention prevents recurrence of HCC-derived tumors. In certain embodiments, administration of a compound of the invention prevents recurrence of HCC-derived tumor metastasis.

In certain embodiments, a subject selected for treatment for liver cancer has liver lesions. In certain embodiments, a subject selected for treatment for liver cancer has elevated serum alpha-fetoprotein and/or elevated serum des-gamma-carboxyprothrombin. In certain embodiments, a subject selected for treatment of liver cancer has abnormal liver function.

In certain embodiments, administration of a compound of the invention reduces serum alpha-fetoprotein and/or serum des-gamma-carboxyprothrombin in a subject having liver cancer. In certain embodiments, levels of serum alpha-fetoprotein and/or serum des-gamma-carboxyprothrombin are measured to assess therapeutic efficacy. In certain embodiments, administration of a compound of the invention improves liver function of the subject.

These and other embodiments of the present invention will become apparent in conjunction with the figures, description and claims that follow.

MiRNAs with relatively high expression values in the treated cells include hsa-miR-191, hsa-miR-181a, hsa-miR-181b, and hsa-miR-181a*.

Figure 6:
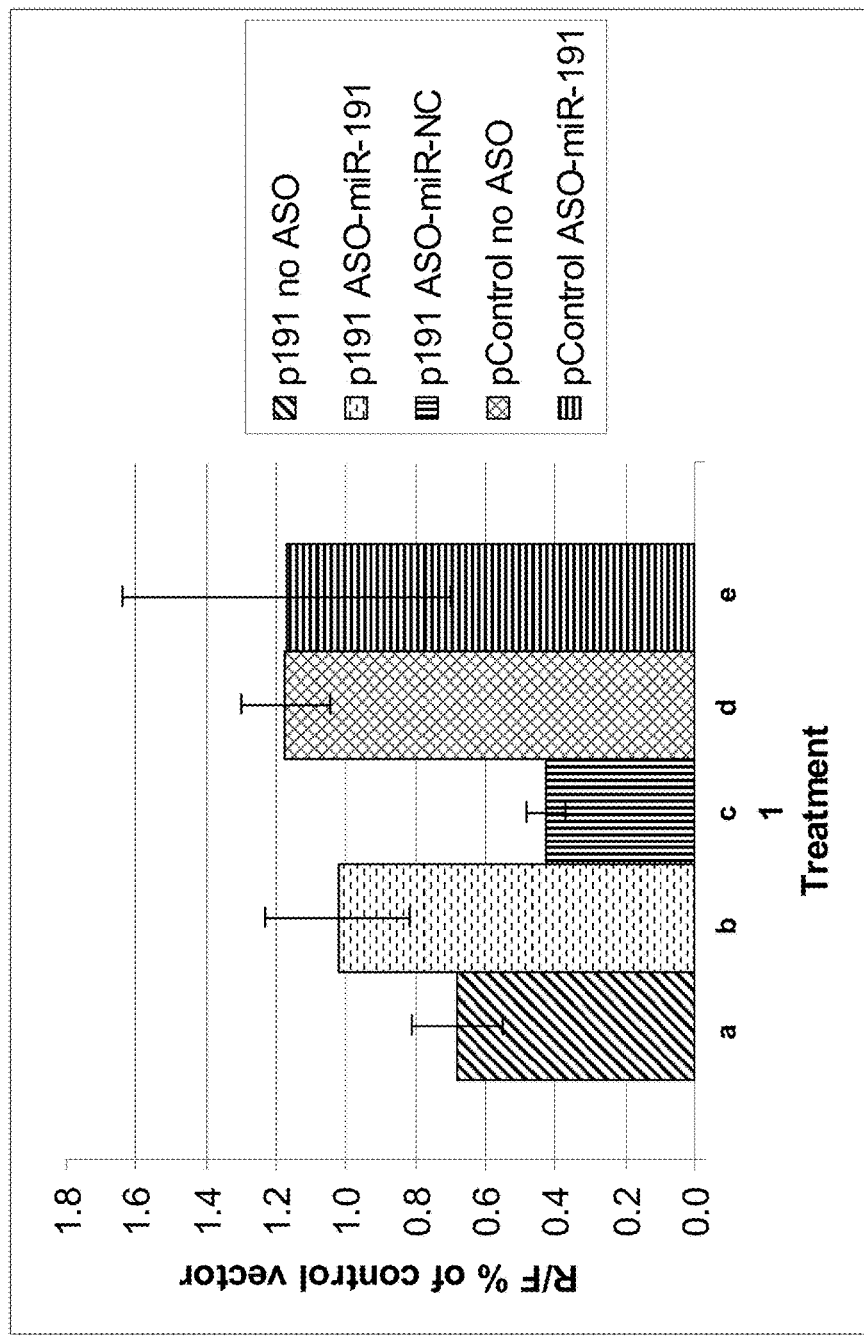

FIG. 6: The results of the Dual-Luciferase Reporter Assay are presented in a bar-chart, in which the Y-axis represents the R/F % ratio of control vector. Each bar depicts the normalized luminescence as follows: Bar a—p191 (plasmid baring reverse complement seq of miR-191 at the 3'UTR of *renilla* luciferase only with no modified oligonucleotides), Bar b—p191 ASO-miR-NC; Bar c—pControl (control plasmid) ASO-miR-191; Bar d—p191 ASO-miR-191; Bar e—pControl (no modified oligonucleotides).

Figure 7:
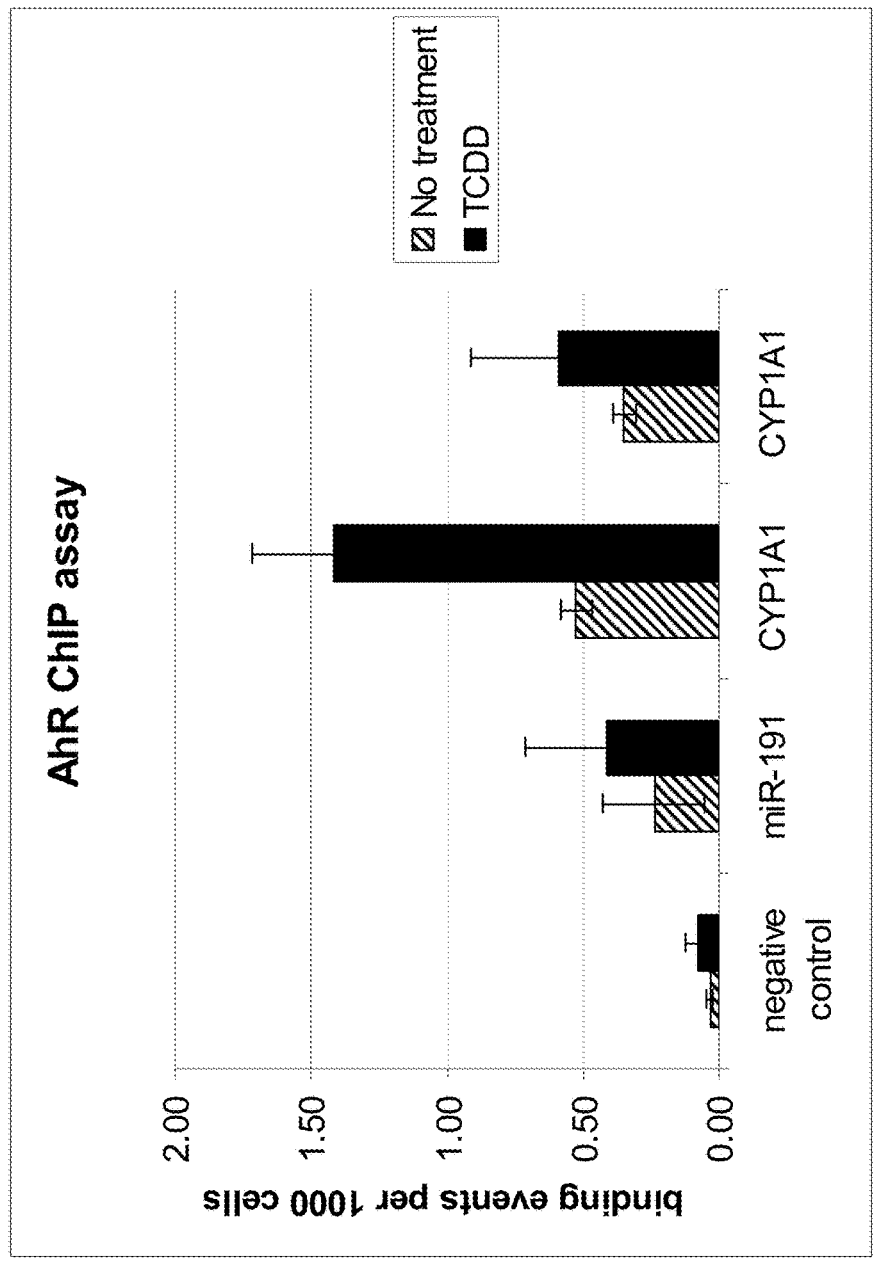

FIG. 7. ChIP (Chromatin Immuno Precipitation) assay using a specific antibody for AhR. The Y-axis depicts binding events per 1,000 cells, with the bars with diagonal stripes representing cells treated with TCDD, and the bars with dots representing cells which were not treated. The pair of bars on the left represents the negative control. The two pairs of bars on the right represent the two binding sites for the AhR/Arnt TF on CYP1A1.

DETAILED DESCRIPTION

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain such techniques and procedures may be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can command go, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Definitions

"Liver cancer" means malignancy of the liver, either a primary cancer or metastasized cancer. In certain embodiments, liver cancer includes, but is not limited to, cancer arising from hepatocytes, such as, for example, hepatomas and hepatocellular carcinomas; fibrolamellar carcinoma; and cholangiocarcinomas (or bile duct cancer).

"Hepatocellular carcinoma" means primary cancer of the liver arising from hepatocytes.

"Dioxin induced liver cancer" means a liver cancer that is caused by dioxin exposure. In certain embodiments, a dioxin-induced liver cancer is dioxin-induced hepatocellular carcinoma.

"Subject" means a human or non-human animal selected for treatment or therapy.

"Subject in need thereof" means a subject identified as in need of a therapy or treatment. In certain embodiments, a subject has liver cancer. In such embodiments, a subject has one or more clinical indications of liver cancer or is at risk for developing liver cancer.

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein.

"Intratumoral administration" means administration within a tumor.

"Chemoembolization" means a procedure in which the blood supply to a tumor is blocked surgically, mechanically, or chemically and chemotherapeutic agents are administered directly into the tumor.

"Duration" means the period of time during which an activity or event continues. In certain embodiments, the duration of treatment is the period of time during which doses of a pharmaceutical agent or pharmaceutical composition are administered.

"Therapy" means a disease treatment method. In certain embodiments, therapy includes, but is not limited to, chemotherapy, surgical resection, liver transplant, and/or chemoembolization.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Prevention" refers to delaying or forestalling the onset or development or progression of a condition or disease for a period of time, including weeks, months, or years.

"Therapeutic agent" means a pharmaceutical agent used for the cure, amelioration or prevention of a disease.

"Chemotherapeutic agent" means a pharmaceutical agent used to treat cancer.

"Chemotherapy" means treatment of a subject with one or more pharmaceutical agents that kills cancer cells and/or slows the growth of cancer cells.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a modified oligonucleotide and a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Metastasis" means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

"Overall survival time" means the time period for which a subject survives after diagnosis of or treatment for a disease. In certain embodiments, the disease is cancer.

"Progression-free survival" means the time period for which a subject having a disease survives, without the disease getting worse. In certain embodiments, progression-free survival is assessed by staging or scoring the disease. In certain embodiments, progression-free survival of a subject having liver cancer is assessed by evaluating tumor size, tumor number, and/or metastasis.

"Blood tumor marker" means a biomarker that increases or decreases in the blood of a subject having cancer.

"Improved liver function" means the change in liver function toward normal limits. In certain embodiments, liver function is assessed by measuring molecules found in a subject's blood. For example, in certain embodiments, improved liver function is measured by a reduction in blood liver transaminase levels.

"Acceptable safety profile" means a pattern of side effects that is within clinically acceptable limits.

"Side effect" means a physiological response attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

"Injection site reaction" means inflammation or abnormal redness of skin at a site of injection in an individual.

"Subject compliance" means adherence to a recommended or prescribed therapy by a subject.

"Comply" means the adherence with a recommended therapy by a subject.

"Recommended therapy" means a treatment recommended by a medical professional for the treatment, amelioration, or prevention of a disease.

"Target nucleic acid," "target RNA," "target RNA transcript" and "nucleic acid target" all mean any nucleic acid capable of being targeted by antisense compounds.

"Targeting" means the process of design and selection of nucleobase sequence that will hybridize to a target nucleic acid and induce a desired effect.

"Targeted to" means having a nucleobase sequence that will allow hybridization to a target nucleic acid to induce a desired effect. In certain embodiments, a desired effect is reduction of a target nucleic acid.

"Modulation" means to a perturbation of function or activity. In certain embodiments, modulation means an increase in gene expression. In certain embodiments, modulation means a decrease in gene expression.

"Expression" means any functions and steps by which a gene's coded information is converted into structures present and operating in a cell.

"5' target site" refers to the nucleobase of a target nucleic acid which is complementary to the 5'-most nucleobase of a particular oligonucleotide.

"3' target site" means the nucleobase of a target nucleic acid which is complementary to the 3'-most nucleobase of a particular oligonucleotide.

"Region" means a portion of linked nucleosides within a nucleic acid. In certain embodiments, a modified oligonucleotide has a nucleobase sequence that is complementary to a region of a target nucleic acid. For example, in certain such embodiments a modified oligonucleotide is complementary to a region of a miRNA stem-loop sequence. In certain such embodiments, a modified oligonucleotide is fully complementary to a region of a miRNA stem-loop sequence.

"Segment" means a smaller or sub-portion of a region.

"Nucleobase sequence" means the order of contiguous nucleobases, in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means a first nucleobase sequence is at least 60%, at least 65%, at least 70%, at least 75%, at least 80%, at least 85%, at least 90%, at least 95%, at least 97%, at least 98% at least 99%, or 100%, identical to the complement of a second nucleobase sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the two sequences hybridize under stringent hybridization conditions.

"Complementarity" means the nucleobase pairing ability between a first nucleic acid and a second nucleic acid.

"Fully complementary" means each nucleobase of a first nucleic acid is capable of pairing with a nucleobase at each corresponding position in a second nucleic acid. For example, in certain embodiments, a modified oligonucleotide wherein each nucleobase has complementarity to a nucleobase within a region of a miRNA stem-loop sequence is fully complementary to the miRNA stem-loop sequence. In certain embodiments, a modified oligonucleotide that is fully complementary to a miRNA or a precursor thereof has a nucleobase sequence that is identical to the complement of a miRNA or a precursor thereof over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases.

"Percent complementarity" means the number of complementary nucleobases in a nucleic acid divided by the length of the nucleic acid. In certain embodiments, percent complementarity of a modified oligonucleotide means the number of nucleobases that are complementary to the target nucleic acid, divided by the length of the modified oligonucleotide.

"Percent identity" means the number of nucleobases in first nucleic acid that are identical to nucleobases at corresponding positions in a second nucleic acid, divided by the total number of nucleobases in the first nucleic acid.

"Substantially identical" used herein may mean that a first and second nucleobase sequence are at least 60%, at least 65%, at least 70%, at least 75%, at least 80%, at least 85%, at least 90%, at least 95%, at least 97%, at least 98% at least 99%, or 100%, identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Non-complementary nucleobase" means two nucleobases that are not capable of pairing through hydrogen bonding.

"Identical" means having the same nucleobase sequence.

"miR-21" means the mature miRNA having the nucleobase sequence set forth in SEQ ID NO: 9.

"miR-21 stem-loop sequence" means the stem-loop sequence having the nucleobase sequence set forth in SEQ ID NO: 1.

"miR-125a-5p" means the mature miRNA having the nucleobase sequence set forth in SEQ ID NO: 10.

"miR-125a stem-loop sequence" means the stem-loop sequence having the nucleobase sequence set forth in SEQ ID NO: 2.

"miR-191" means the mature miRNA having the nucleobase sequence set forth in SEQ ID NO: 11.

"miR-191 stem-loop sequence" means the stem-loop sequence having the nucleobase sequence set forth in SEQ ID NO: 3.

"miR-210" means the mature miRNA having the nucleobase sequence set forth in SEQ ID NO: 12.

"miR-210 stem-loop sequence" means the stem-loop sequence having the nucleobase sequence set forth in SEQ ID NO: 4.

"miR-222" means the mature miRNA having the nucleobase sequence set forth in SEQ ID NO: 13.

"miR-222 stem-loop sequence" means the stem-loop sequence having the nucleobase sequence set forth in SEQ ID NO: 5.

"miR-378" means the mature miRNA having the nucleobase sequence set forth in SEQ ID NO: 14.

"miR-378 stem-loop sequence" means the stem-loop sequence having the nucleobase sequence set forth in SEQ ID NO: 6.

"miR-423-3p" means the mature miRNA having the nucleobase sequence set forth in SEQ ID NO: 15.

"miR-423 stem-loop sequence" means the stem-loop sequence having the nucleobase sequence set forth in SEQ ID NO: 7.

"miR-638" means the mature miRNA having the nucleobase sequence set forth in SEQ ID NO: 16.

"miR-638 stem-loop sequence" means the stem-loop sequence having the nucleobase sequence set forth in SEQ ID NO: 8.

"miR-181a" means the mature miRNA having the nucleobase sequence set forth in SEQ ID NO: 31.

"miR-181a*" means the mature miRNA having the nucleobase sequence set forth in SEQ ID NO: 32.

"miR-181b" means the mature miRNA having the nucleobase sequence set forth in SEQ ID NO: 33.

"miR-181a-1 stem-loop sequence" means the stem-loop sequence having the nucleobase sequence set forth in SEQ ID NO: 34.

"miR-181a-2 stem-loop sequence" means the stem-loop sequence having the nucleobase sequence set forth in SEQ ID NO: 35.

"miR-181b-1 stem-loop sequence" means the stem-loop sequence having the nucleobase sequence set forth in SEQ ID NO: 36.

"miR-181b-2 stem-loop sequence" means the stem-loop sequence having the nucleobase sequence set forth in SEQ ID NO: 37.

"miRNA" or "miR" means a non-coding RNA between 18 and 25 nucleobases in length, which is the product of cleavage of a pre-miRNA by the enzyme Dicer. Examples of mature miRNAs are found in the miRNA database known as miRBase (microrna.sanger.ac.uk).

"Pre-miRNA" or "pre-miR" means a non-coding RNA having a hairpin structure, which is the product of cleavage of a pri-miR by the double-stranded RNA-specific ribonuclease known as Drosha.

"Stem-loop sequence" means an RNA having a hairpin structure and containing a mature miRNA sequence. Pre-miRNA sequences and stem-loop sequences may overlap. Examples of stem-loop sequences are found in the miRNA database known as miRBase (microrna.sanger.ac.uk).

"Pri-miRNA" or "pri-miR" means a non-coding RNA having a hairpin structure that is a substrate for the double-stranded RNA-specific ribonuclease Drosha.

"miRNA precursor" means a transcript that originates from a genomic DNA and that comprises a non-coding, structured RNA comprising one or more miRNA sequences. For example, in certain embodiments a miRNA precursor is a pre-miRNA. In certain embodiments, a miRNA precursor is a pri-miRNA.

"Monocistronic transcript" means a miRNA precursor containing a single miRNA sequence.

"Polycistronic transcript" means a miRNA precursor containing two or more miRNA sequences.

"Seed sequence" means nucleotides 2 to 6 or 2 to 7 from the 5'-end of a mature miRNA sequence.

"Oligomeric compound" means a compound comprising a polymer of linked monomeric subunits.

"Oligonucleotide" means a polymer of linked nucleosides, each of which can be modified or unmodified, independent from one another.

"Naturally occurring internucleoside linkage" means a 3' to 5' phosphodiester linkage between nucleosides.

"Natural sugar" means a sugar found in DNA (2'-H) or RNA (2'-OH).

"Natural nucleobase" means a nucleobase that is unmodified relative to its naturally occurring form.

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar.

"Nucleotide" means a nucleoside having a phosphate group covalently linked to the sugar portion of a nucleoside.

"Modified oligonucleotide" means an oligonucleotide having one or more modifications relative to a naturally occurring terminus, sugar, nucleobase, and/or internucleoside linkage.

"Single-stranded modified oligonucleotide" means a modified oligonucleotide which is not hybridized to a complementary strand.

"Modified internucleoside linkage" means any change from a naturally occurring internucleoside linkage.

"Phosphorothioate internucleoside linkage" means a linkage between nucleosides where one of the non-bridging atoms is a sulfur atom.

"Modified sugar" means substitution and/or any change from a natural sugar.

"Modified nucleobase" means any substitution and/or change from a natural nucleobase.

"5-methylcytosine" means a cytosine modified with a methyl group attached to the 5' position.

"2'-O-methyl sugar" or "2'-OMe sugar" means a sugar having a O-methyl modification at the 2' position.

"2'-O-methoxyethyl sugar" or "2'-MOE sugar" means a sugar having a 0-methoxyethyl modification at the 2' position.

"2'-O-fluoro" or "2'-F" means a sugar having a fluoro modification of the 2' position.

"Bicyclic sugar moiety" means a sugar modified by the bridging of two non-geminal ring atoms.

"2'-O-methoxy ethyl nucleoside" means a 2'-modified nucleoside having a 2'-O-methoxyethyl sugar modification.

"2'-fluoro nucleoside" means a 2'-modified nucleoside having a 2'-fluoro sugar modification.

"2'-O-methyl" nucleoside means a 2'-modified nucleoside having a 2'-O-methyl sugar modification.

"Bicyclic nucleoside" means a 2'-modified nucleoside having a bicyclic sugar moiety.

"Motif" means a pattern of modified and/or unmodified nucleobases, sugars, and/or internucleoside linkages in an oligonucleotide.

A "fully modified oligonucleotide" means each nucleobase, each sugar, and/or each internucleoside linkage is modified.

A "uniformly modified oligonucleotide" means each nucleobase, each sugar, and/or each internucleoside linkage has the same modification throughout the modified oligonucleotide.

A "gapmer" means a modified oligonucleotide having an internal region of linked nucleosides positioned between two external regions of linked nucleosides, where the nucleosides of the internal region comprise a sugar moiety different than that of the nucleosides of each external region.

A "gap segment" is an internal region of a gapmer that is positioned between the external regions.

A "wing segment" is an external region of a gapmer that is located at the 5' or 3' terminus of the internal region.

A "symmetric gapmer" means each nucleoside of each external region comprises the same sugar modification.

An "asymmetric gapmer" means each nucleoside of one external region comprises a first sugar modification, and each nucleoside of the other external region comprises a second sugar modification.

A "stabilizing modification" means a modification to a nucleoside that provides enhanced stability to a modified oligonucleotide, in the presence of nucleases, relative to that provided by 2'-deoxynucleosides linked by phosphodiester internucleoside linkages. For example, in certain embodiments, a stabilizing modification is a stabilizing nucleoside modification. In certain embodiments, a stabilizing modification is a internucleoside linkage modification.

A "stabilizing nucleoside" means a nucleoside modified to provide enhanced nuclease stability to an oligonucleotide, relative to that provided by a 2'-deoxynucleoside. In one embodiment, a stabilizing nucleoside is a 2'-modified nucleoside.

A "stabilizing internucleoside linkage" means an internucleoside linkage that provides enhanced nuclease stability to an oligonucleotide relative to that provided by a phosphodiester internucleoside linkage. In one embodiment, a stabilizing internucleoside linkage is a phosphorothioate internucleoside linkage.

Overview

Liver cancer is a common cause of cancer deaths in both men and women worldwide. The incidence of hepatocellular carcinoma (HCC), the most common type of liver cancer, is rising in relation to the increasing incidence of hepatitis C viral infection. Certain HCC cases have been linked to chronic hepatitis B infection, chronic hepatitis C infection, or cirrhosis.

Subjects with HCC have a very poor prognosis, with typical median survival from the date of diagnosis ranging from 7 to 8 months, and a 5 year survival rate of less than 5%. Limited treatments are available for HCC. Subjects with early stage disease may be treated by liver resection or liver transplantation. However, in approximately 85% of subjects the disease is too advanced at the time of diagnosis for liver resection or transplantation. Subjects with intermediate disease may be candidates for chemoembolization. However, the poor health of subjects with advanced disease limits the use of chemoembolization.

Certain changes in miRNA expression patterns in cancer cells, including liver cancer cells such as HCC, relative to non-cancerous cells, have been reported. Both increases and decreases in miRNA expression have been described in relation to cancer. The total number of miRNAs in the human genome is estimated to range from approximately 500 to several thousand. In view of this high number of total miRNAs, identification of particular miRNAs linked to particular cancer types is necessary in order to identify miRNAs that could be targeted for cancer therapy, either through inhibition or augmentation of the miRNA.

Accordingly, there exists a need for the identification of miRNAs that can be inhibited for the treatment of liver cancer, including HCC. Also needed are inhibitory agents useful for the treatment of liver cancer, such as HCC. Further, there exists a need for methods of treating liver cancer, such as HCC, by administering to a subject in need thereof a pharmaceutical agent capable of inhibiting a miRNA identified as dysregulated in connection with liver cancer, such as HCC. As cancer is a disease caused by the uncontrolled proliferation of cells, as well as increased cell survival, desirable traits of pharmaceutical agents for the treatment of liver cancer include the ability to reduce cell proliferation, and/or induce apoptosis, which will in turn reduce tumor size, reduce tumor number, and/or prevent or slow the metastasis of liver cancer cells.

In certain embodiments, the methods provided herein are useful for the treatment of liver cancer, such as HCC. These methods may result in one or more clinically desirable outcomes in a subject having liver cancer, such as reduction in tumor number and/or size, reduced metastatic progression, prolonged survival time, and/or increased progression-free survival time. Also provided herein are pharmaceutical agents, such as modified oligonucleotides, that may be used for the treatment of liver cancer, such as HCC.

As illustrated herein, using microarrays containing probes designed to about 700 miRNAs, liver samples from HCC tumors were compared to normal liver tissue samples. Of the about 700 miRNAs tested, approximately 90 were found to be upregulated in HCC samples relative to normal liver tissue samples. Following in vitro experiments in HCC-derived cell lines, 8 miRNAs were selected as candidate miRNAs to be targeted for HCC therapy: miR-21, miR-125a-5p, miR-191, miR-210, miR-222, miR-378, miR-423-3p, and miR-638. As illustrated herein, a reduction in cell proliferation was observed following the inhibition of 8 of these miRNAs in liver cancer cell lines, using modified oligonucleotides complementary to the miRNAs. Additionally, inhibition of 7 of the miRNAs resulted in increased apoptosis of liver cancer cells. As such, the modified oligonucleotides complementary to each of these 8 miRNAs are pharmaceutical agents for the treatment of liver cancer, including HCC.

As illustrated herein in a mouse subcutaneous tumor model, the administration of a modified oligonucleotide targeted to microRNAs identified as upregulated in HCC resulted in tumor volume reduction. Accordingly, such modified oligonucleotides are pharmaceutical agents for the treatment of liver cancer, including HCC.

Certain Treatments

In certain embodiments, the present invention provides methods for the treatment of cancer comprising administering to a subject in need thereof a modified oligonucleotide complementary to a miRNA. A subject may be diagnosed with liver cancer following the administration of medical tests well-known to those in the medical profession. The liver cancer may be hepatocellular carcinoma (HCC). The diagnosis of hepatocellular carcinoma is typically made by liver imaging tests such as abdominal ultrasound, helical computed tomography (CT) scan or triple phase CT scan. Such imaging tests may be performed in conjunction with measurement of blood levels of alpha-fetoprotein and/or blood levels of des-gamma-carboxyprothrombin. In certain subjects, MRI may be used in place of CT scan. The liver imaging tests allow the assessment of the tumor size, number, location, metastasis outside the liver, patency and or invasion of the arteries and veins of the liver by the tumor. This assessment aids the decision as to the mode of therapeutic or palliative intervention that is appropriate. The final diagnosis is typically confirmed by needle biopsy and histopathological examination.

Accordingly, in certain embodiments, the liver cancer is detected following a computed tomography (CT) scan that detects tumors. In certain embodiments, the liver cancer is detected following magnetic resonance imaging (MRI). In certain embodiments, HCC is characterized as a single primary tumor. In certain embodiments, HCC is characterized as multiple primary tumors. In certain embodiments, HCC is characterized as a poorly defined primary tumor with an infiltrative growth pattern. In certain embodiments, the HCC is a single primary tumor with vascular invasion.

In certain embodiments, the HCC is characterized as multiple primary tumors with vascular invasion. In certain embodiments, the HCC has metastasized to one or more lymph nodes. In certain such embodiments, the lymph nodes are regional lymph nodes. In certain embodiments, the HCC has metastasized to one or more distant tissues. In certain embodiments, the HCC has metastasized to other regions of the liver, the portal vein, lymph nodes, adrenal glands, bone or lungs. In certain embodiments, fibrosis is present.

A number of systems have been employed to predict the prognosis for HCC, including the TNM system, the Okuda system, the Barcelona Clinic Liver Cancer (BCLC) and the CLIP score. Each of these systems incorporates four features that have been recognized as being important determinants of survival: the severity of underlying liver disease, the size of the tumor, extension of the tumor into adjacent structures, and the presence of metastases. The TNM system classifies HCC as stage I, II, III, IV, or V. The BCLC classifies HCC as Stage A1, A2, A3, A4, B, C, and D, and includes consideration of a Child-Pugh score.

In certain embodiments, liver cancer is classified as Stage 1, Stage 2, Stage 3A, Stage 3B, Stage 3C, or Stage 4. Stage 1 is characterized by a cancer is no bigger than 2 cm in size and that has not begun to spread. At Stage 2, the cancer is affecting blood vessels in the liver, or there is more than one tumor in the liver. At Stage 3A, the cancer is bigger than 5 cm in size or has spread to the blood vessels near the liver. At Stage 3B, the cancer has spread to nearby organs, such as the bowel or the stomach, but has not spread to the lymph nodes. At Stage 3C the cancer can be of any size and has spread to nearby lymph nodes. At Stage 4 the cancer has spread to parts of the body further away from the liver, such as the lungs.

Biomarkers in a subject's blood may be used to augment a diagnosis of liver cancer, stage a liver cancer, or develop a prognosis for survival. Such biomarkers include blood tumor biomarkers, such as alpha-fetoprotein and des-gamma carboxyprothrombin. In certain such embodiments, the subject has elevated blood alpha-fetoprotein. In certain such embodiments, the subject has elevated blood des-gamma carboxyprothrombin.

A subject having liver cancer may also suffer from abnormal liver function. Liver function may be assessed by liver function tests, which measure, among other things, blood levels of liver transaminases. In certain embodiments, a subject having abnormal liver function has elevated blood liver transaminases. Blood liver transaminases include alanine aminotransferase (ALT) and aspartate aminotransferase (AST). In certain embodiments, a subject having abnormal liver function has elevated blood bilirubin. In certain embodiments, a subject has abnormal blood albumin levels.

In certain embodiments, a subject's liver function is assessed by the Child-Pugh classification system, which defines three classes of liver function. In this classification system, points are assigned to measurements in one of five categories: bilirubin levels, albumin levels, prothrombin time, ascites, and encephalopathy. One point is assigned per each of the following characteristics present: blood bilirubin of less than 2.0 mg/dl; blood albumin of greater than 3.5 mg/dl; a prothrombin time of less than 1.7 international normalized ratio (INR); ascites is absent; or encephalopathy is absent. Two points are assigned per each of the following characteristics present: blood bilirubin of 2-3 mg/dl; blood bilirubin of 3.5 to 2.8 mg/dl; prothrombin time of 1.7-2.3 INR; ascites is mild to moderate; or encephalopathy is mild. Three points are assigned per each of the following characteristics present: bilirubin of greater than 3.0 mg/dl; blood albumin of less than 2.8 mg/dl; prothrombin time of greater than 2.3 INR; ascites is severe to refractory; or encephalopathy is severe. The scores are added and Class A is assigned for a score of 5-6 points, Class B is assigned for a score of 7-9 points, and Class C is assigned for a score of 10-15 points, A subject having liver cancer may have suffered from chronic hepatitis C infection, chronic hepatitis B infection, or cirrhosis. Subjects having liver cancer caused by hepatitis C infection, hepatitis B infection, or cirrhosis may be treated by the methods described herein.

A subject's response to treatment may be evaluated by tests similar to those used to diagnosis the liver cancer, including, without limitation, CT scan, MRI, and needle biopsy. Response to treatment may also be assessed by measuring biomarkers in blood, for comparison to pre-treatment levels of biomarkers.

Administration of a pharmaceutical composition of the present invention to a subject having liver cancer results in one or more clinically desirable outcomes. Such clinically desirable outcomes include reduction of tumor number or reduction of tumor size. Additional clinically desirable outcomes include the extension of overall survival time of the subject, and/or extension of progression-free survival time of the subject. In certain embodiments, administration of a pharmaceutical composition of the invention prevents an increase in tumor size and/or tumor number. In certain embodiments, administration of a pharmaceutical composition of the invention prevents metastatic progression. In certain embodiments, administration of a pharmaceutical composition of the invention slows or stops metastatic progression. In certain embodiments, administration of a pharmaceutical composition of the invention prevents the recurrence of liver tumors. In certain embodiments, administration of a pharmaceutical composition of the invention prevents recurrence of liver tumor metastasis. In certain embodiments, administration of a pharmaceutical composition of the invention prevents the recurrence of HCC-derived tumors. In certain embodiments, administration of a pharmaceutical composition of the invention prevents the recurrence of HCC-derived tumor metastasis.

Administration of a pharmaceutical composition of the present invention to liver cancer cells, including HCC cells, may result in desirable phenotypic effects. In certain embodiments, a modified oligonucleotide may stop, slow or reduce the uncontrolled proliferation of liver cancer cells. In certain embodiments, a modified oligonucleotide may induce apoptosis in liver cancer cells. In certain embodiments, a modified oligonucleotide may reduce liver cancer cell survival.

A miRNA hybridizes to a mRNA to regulate expression of the mRNA and its protein product. Generally, the hybridization of a miRNA to its mRNA target inhibits expression of the mRNA. Thus, the inhibition of a miRNA may result in the increased expression of a miRNA nucleic acid target. In certain embodiments, the inhibition of a miRNA results in the increase of a protein encoded by a miRNA nucleic acid target. For example, in certain embodiments, the antisense inhibition of miR-222 results in an increase of $p27^{kip1}$.

Certain desirable clinical outcomes may be assessed by measurements of blood biomarkers. In certain embodiments, administration of a pharmaceutical composition of the invention may result in the decrease of blood alpha-fetoprotein and/or blood des-gamma carboxyprothrombin. Administration of a pharmaceutical composition of the invention may further result in the improvement of liver function, as evidenced by a reduction in blood ALT and/or AST levels.

Certain Compounds

The compounds provided herein are useful for the treatment of liver cancer, such as HCC. In certain embodiments, the compound comprises a modified oligonucleotide. In certain such embodiments, the compound consists of a modified oligonucleotide.

In certain such embodiments, the compound comprises a modified oligonucleotide hybridized to a complementary strand, i.e. the compound comprises a double-stranded oligomeric compound. In certain embodiments, the hybridization of a modified oligonucleotide to a complementary strand forms at least one blunt end. In certain such embodiments, the hybridization of a modified oligonucleotide to a complementary strand forms a blunt end at each terminus of the double-stranded oligomeric compound. In certain embodiments, a terminus of a modified oligonucleotide comprises one or more additional linked nucleosides relative to the number of linked nucleosides of the complementary strand. In certain embodiments, the one or more additional nucleosides are at the 5' terminus of a modified oligonucleotide. In certain embodiments, the one or more additional nucleosides are at the 3' terminus of a modified oligonucleotide. In certain embodiments, at least one nucleobase of a nucleoside of the one or more additional nucleosides is complementary to the target RNA. In certain embodiments, each nucleobase of each one or more additional nucleosides is complementary to the target RNA. In certain embodiments, a terminus of the complementary strand comprises one or more additional linked nucleosides relative to the number of linked nucleosides of a modified oligonucleotide. In certain embodiments, the one or more additional linked nucleosides are at the 3' terminus of the complementary strand. In certain embodiments, the one or more additional linked nucleosides are at the 5' terminus of the complementary strand. In certain embodiments, two additional linked nucleosides are linked to a terminus. In certain embodiments, one additional nucleoside is linked to a terminus.

In certain embodiments, the compound comprises a modified oligonucleotide conjugated to one or more moieties which enhance the activity, cellular distribution or cellular uptake of the resulting antisense oligonucleotides. In certain such embodiments, the moiety is a cholesterol moiety or a lipid moiety. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to a modified oligonucleotide. In certain embodiments, a conjugate group is attached to a modified oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises a modified oligonucleotide having one or more stabilizing groups that are attached to one or both termini of a modified oligonucleotide to enhance properties such as, for example, nuclease stability. Included in stabilizing groups are cap structures. These terminal modifications protect a modified oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-amino-alkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Certain Nucleobase Sequences

In certain embodiments, a modified oligonucleotide has a sequence that is complementary to a miRNA or a precursor thereof. Nucleobase sequences of mature miRNAs and their corresponding stem-loop sequences described herein are the sequences found in miRBase, an online searchable database of miRNA sequences and annotation, found at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. For example, miR-378 of Release 10.0 described herein was formerly named miR-422b. A sequence database release may result in a variation of a mature miRNA sequence. For example, miR-125a-5p of Release 10.0 is found at nucleobases 15-38 of the miR-125a stem-loop sequence (SEQ ID NO: 2). miR-125a in a previous database Releases is found at nucleobases 15-37 of the miR-125a stem-loop sequence (SEQ ID NO: 2). The compositions of the present invention encompass modified oligonucleotides that are complementary to any nucleobase sequence version of the miRNAs described herein.

In certain embodiments, a modified oligonucleotide has a nucleobase sequence that is complementary to a miRNA or a precursor thereof, meaning that the nucleobase sequence of a modified oligonucleotide is a least 60%, 65%, 70%, 75%, 80%, 85%, 90%, 95%, 97%, 98% or 99% identical to the complement of a miRNA or precursor thereof over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the two sequences hybridize under stringent hybridization conditions. Accordingly, in certain embodiments the nucleobase sequence of a modified oligonucleotide may have one or more mismatched basepairs with respect to its target miRNA or precursor sequence, and is capable of hybridizing to its target sequence. In certain embodiments, a modified oligonucleotide has a nucleobase sequence that is fully complementary to a miRNA or precursor thereof, meaning that the nucleobase sequence of a modified oligonucleotide is 100% identical of the complement of an miRNA or a precursor thereof over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases.

In certain embodiments, a modified oligonucleotide has a sequence that is complementary to a nucleobase sequence of a miRNA stem-loop sequence selected from the miR-21 stem-loop sequence (SEQ ID NO: 1), the miR-125a stem-loop sequence (SEQ ID NO: 2), the miR-191 stem-loop sequence (SEQ ID NO: 3), the miR-210 stem-loop sequence (SEQ ID NO: 4), the miR-222 stem-loop sequence (SEQ ID NO: 5), the miR-378 stem-loop sequence (SEQ ID NO: 6), the miR-423 stem-loop sequence (SEQ ID NO: 7), and the miR-638 stem-loop sequence (SEQ ID NO: 8).

In certain embodiments, a modified oligonucleotide has a sequence that is complementary to a nucleobase sequence of a miRNA, where the nucleobase sequence of the miRNA is selected from SEQ ID NO: 9, 10, 11, 12, 13, 14, 15, and 16.

In certain embodiments, a modified oligonucleotide has a nucleobase sequence that is complementary to a region of the miR-21 stem-loop sequence (SEQ ID NO: 1). In certain embodiments, a modified oligonucleotide has a nucleobase sequence that is complementary to the region of nucleobases 8-29 of SEQ ID NO: 1. In certain embodiments, a modified oligonucleotide has a nucleobase sequence that is complementary to the nucleobase sequence of miR-21 (SEQ ID NO: 9). In certain embodiments, a modified oligonucleotide has a nucleobase sequence that is complementary to nucleobases 1-22 of SEQ ID NO: 9. In certain embodiments, a modified oligonucleotide has a nucleobase sequence comprising the nucleobase sequence TCAACATCAGTCTGATAAGCTA (SEQ ID NO: 17). In certain embodiments, a modified oligonucleotide has a nucleobase sequence consisting of the nucleobase sequence TCAACATCAGTCTGATAAGCTA (SEQ ID NO: 17).

In certain embodiments, a modified oligonucleotide has a nucleobase sequence that is complementary to a region of the miR-125a stem-loop sequence (SEQ ID NO: 2). In certain embodiments, a modified oligonucleotide has a nucleobase sequence that is complementary to the region of nucleobases 15-37 of SEQ ID NO: 2. In certain embodiments, a modified oligonucleotide has a nucleobase sequence that is complementary to the region of nucleobases 15-38 of SEQ ID NO: 2. In certain embodiments, a modified oligonucleotide has a nucleobase sequence that is complementary to the nucleobase sequence of miR-125-5p (SEQ ID NO: 10). In certain embodiments, a modified oligonucleotide has a nucleobase sequence that is complementary to nucleobases 1-23 of SEQ ID NO: 10. In certain embodiments, a modified oligonucleotide has a nucleobase sequence that is complementary to nucleobases 1-24 of SEQ ID NO: 10. In certain embodiments, a modified oligonucleotide has a nucleobase sequence comprising the nucleobase sequence CACAGGTTAAAGGGTCTCAGGGA (SEQ ID NO: 18). In certain embodiments, a modified oligonucleotide has a nucleobase sequence consisting of the nucleobase sequence CACAGGTTAAAGGGTCTCAGGGA (SEQ ID NO: 18). In certain embodiments, a modified oligonucleotide has a nucleobase sequence consisting of the nucleobase sequence TCACAGGTTAAAGGGTCTCAGGGA (SEQ ID NO: 19).

In certain embodiments, a modified oligonucleotide has a nucleobase sequence that is complementary to a region of the miR-191 stem-loop sequence (SEQ ID NO: 3). In certain embodiments, a modified oligonucleotide has a nucleobase sequence that is complementary to the region of nucleobases 16-37 of SEQ ID NO: 3. In certain embodiments, a modified oligonucleotide has a nucleobase sequence that is complementary to the region of nucleobases 16-38 of SEQ ID NO: 3. In certain embodiments, a modified oligonucleotide has a nucleobase sequence that is complementary to the nucleobase sequence of miR-191 (SEQ ID NO: 11). In certain embodiments, a modified oligonucleotide has a nucleobase sequence comprising the nucleobase sequence AGCTGCTTTTGGGATTCCGTTG (SEQ ID NO: 20). In certain embodiments, a modified oligonucleotide has a nucleobase sequence consisting of the nucleobase sequence AGCTGCTTTTGGGATTCCGTTG (SEQ ID NO: 20). In certain embodiments, a modified oligonucleotide has a nucleobase sequence consisting of the nucleobase sequence of CAGCTGCTTTTGGGATTCCGTTG (SEQ ID NO: 21).

In certain embodiments, a modified oligonucleotide has a nucleobase sequence that is complementary to a region of the miR-210 stem-loop sequence (SEQ ID NO: 4). In certain embodiments, a modified oligonucleotide has a nucleobase sequence that is complementary to the region of nucleobases 66-87 of SEQ ID NO: 4. In certain embodiments, a modified oligonucleotide has a nucleobase sequence that is complementary to the nucleobase sequence of miR-210 (SEQ ID NO: 12). In certain embodiments, a modified oligonucleotide has a nucleobase sequence comprising the nucleobase sequence TCAGCCGCTGTCACACGCACAG (SEQ ID NO: 22). In certain embodiments, a modified oligonucleotide has a nucleobase sequence consisting of the nucleobase sequence TCAGCCGCTGTCACACGCACAG (SEQ ID NO: 22).

In certain embodiments, a modified oligonucleotide has a nucleobase sequence that is complementary to a region of the miR-222 stem-loop sequence (SEQ ID NO: 5). In certain embodiments, a modified oligonucleotide has a nucleobase sequence that is complementary to the region of nucleobases 69-89 of SEQ ID NO: 5. In certain embodiments, a modified oligonucleotide has a nucleobase sequence that is complementary to the region of nucleobases 69-91 of SEQ ID NO: 5. In certain embodiments, a modified oligonucleotide has a nucleobase sequence that is complementary to the nucleobase sequence of miR-222 (SEQ ID NO: 13). In certain embodiments, a modified oligonucleotide has a nucleobase sequence comprising the nucleobase sequence ACCCAGTAGCCAGATGTAGCT (SEQ ID NO: 24). In certain embodiments, a modified oligonucleotide has a nucleobase sequence consisting of the nucleobase sequence ACCCAGTAGCCAGATGTAGCT (SEQ ID NO: 24). In certain embodiments, a modified oligonucleotide has a nucleobase sequence consisting of the nucleobase sequence GAGACCCAGTAGCCAGATGTAGCT (SEQ ID NO: 23).

In certain embodiments, a modified oligonucleotide has a nucleobase sequence that is complementary to a region of the miR-378 stem-loop sequence (SEQ ID NO: 6). In certain embodiments, a modified oligonucleotide has a nucleobase sequence that is complementary to the region of nucleobases 43-63 of SEQ ID NO: 6. In certain embodiments, a modified oligonucleotide has a nucleobase sequence that is complementary to the region of nucleobases 44-65 of SEQ ID NO: 6. In certain embodiments, a modified oligonucleotide has a nucleobase sequence that is complementary to the nucleobase sequence of miR-378 (SEQ ID NO: 14). In certain embodiments, a modified oligonucleotide has a nucleobase sequence comprising the nucleobase sequence CCTTCTGACTCCAAGTCCAG (SEQ ID NO: 25). In certain embodiments, a modified oligonucleotide has a nucleobase sequence consisting of the nucleobase sequence GGCCTTCTGACTCCAAGTCCAG (SEQ ID NO: 26). In certain embodiments, a modified oligonucleotide has a nucleobase sequence consisting of the nucleobase sequence CCTTCTGACTCCAAGTCCAGT (SEQ ID NO: 27).

In certain embodiments, a modified oligonucleotide has a nucleobase sequence that is complementary to a region of the miR-423 stem-loop sequence (SEQ ID NO: 7). In certain embodiments, a modified oligonucleotide has a nucleobase sequence that is complementary to the region of nucleobases 53-75 of SEQ ID NO: 7. In certain embodiments, a modified oligonucleotide has a nucleobase sequence that is complementary to the region of nucleobases 53-74 of SEQ ID NO: 7. In certain embodiments, a modified oligonucleotide has a nucleobase sequence that is complementary to the nucleobase sequence of miR-423-3p (SEQ ID NO: 15). In certain embodiments, a modified oligonucleotide has a nucleobase sequence comprising the nucleobase sequence CTGAGGGGCCTCAGACCGAGCT (SEQ ID NO: 28).

In certain embodiments, a modified oligonucleotide has a nucleobase sequence consisting of the nucleobase sequence CTGAGGGGCCTCAGACCGAGCT (SEQ ID NO: 28). In certain embodiments, a modified oligonucleotide has a nucleobase sequence consisting of the nucleobase sequence TCTGAGGGGCCTCAGACCGAGCT (SEQ ID NO: 29).

In certain embodiments, a modified oligonucleotide has a nucleobase sequence that is complementary to a region of the miR-638 stem-loop sequence (SEQ ID NO: 8). In certain embodiments, a modified oligonucleotide has a nucleobase sequence that is complementary to the region of nucleobases 16-40 of SEQ ID NO: 8. In certain embodiments, a modified oligonucleotide has a nucleobase sequence that is complementary to the nucleobase sequence of miR-638 (SEQ ID NO: 16). In certain embodiments, a modified oligonucleotide has a nucleobase sequence comprising the nucleobase sequence AGGCCGCCACCCGCCCGCGATCCCT (SEQ ID NO: 30). In certain embodiments, a modified oligonucleotide has a nucleobase sequence consisting of the nucleobase sequence AGGCCGCCACCCGCCCGCGATCCCT (SEQ ID NO: 30).

In certain embodiments, a modified oligonucleotide has a nucleobase sequence that is complementary to a region of the miR-181a-1 stem-loop sequence (SEQ ID NO: 34). In certain embodiments, a modified oligonucleotide has a nucleobase sequence that is complementary to the region of nucleobases 24-46 of SEQ ID NO: 34. In certain embodiments, a modified oligonucleotide has a nucleobase sequence that is complementary to a region of the miR-181a-2 stem-loop sequence (SEQ ID NO: 35). In certain embodiments, a modified oligonucleotide has a nucleobase sequence that is complementary to the region of nucleobases 39-61 of SEQ ID NO: 35. In certain embodiments, a modified oligonucleotide has a nucleobase sequence that is complementary to the nucleobase sequence of miR-181a (SEQ ID NO: 31). In certain embodiments, a modified oligonucleotide has a nucleobase sequence comprising the nucleobase sequence TCACTCCGTCTGCGAAGTTAGAA (SEQ ID NO: 38).

In certain embodiments, a modified oligonucleotide has a nucleobase sequence consisting of the nucleobase sequence TCACTCCGTCTGCGAAGTTAGAA (SEQ ID NO: 38).

In certain embodiments, a modified oligonucleotide has a nucleobase sequence that is complementary to a region of the miR-181a-1 stem-loop sequence (SEQ ID NO: 34). In certain embodiments, a modified oligonucleotide has a nucleobase sequence that is complementary to the region of nucleobases 64-85 of SEQ ID NO: 34. In certain embodiments, a modified oligonucleotide has a nucleobase sequence that is complementary to a region of the miR-181a-2 stem-loop sequence (SEQ ID NO: 35). In certain embodiments, a modified oligonucleotide has a nucleobase sequence that is complementary to the region of nucleobases 77-98 of SEQ ID NO: 35. In certain embodiments, a modified oligonucleotide has a nucleobase sequence that is complementary to the nucleobase sequence of miR-181a* (SEQ ID NO: 32). In certain embodiments, a modified oligonucleotide has a nucleobase sequence comprising the nucleobase sequence GGATCTTACTTCGGACGTAGGA (SEQ ID NO: 39).

In certain embodiments, a modified oligonucleotide has a nucleobase sequence consisting of the nucleobase sequence GGATCTTACTTCGGACGTAGGA (SEQ ID NO: 39).

In certain embodiments, a modified oligonucleotide has a nucleobase sequence that is complementary to a region of the miR-181b-1 stem-loop sequence (SEQ ID NO: 36). In certain embodiments, a modified oligonucleotide has a nucleobase sequence that is complementary to the region of nucleobases 36-58 of SEQ ID NO: 36. In certain embodiments, a modified oligonucleotide has a nucleobase sequence that is complementary to a region of the miR-181b-2 stem-loop sequence (SEQ ID NO: 37). In certain embodiments, a modified oligonucleotide has a nucleobase sequence that is complementary to the region of nucleobases 16-38 of SEQ ID NO: 37. In certain embodiments, a modified oligonucleotide has a nucleobase sequence that is complementary to the nucleobase sequence of miR-181b (SEQ ID NO: 33). In certain embodiments, a modified oligonucleotide has a nucleobase sequence comprising the nucleobase sequence TCCCTCCGTCTGCTTAGTTAGAA (SEQ ID NO: 40).

In certain embodiments, a modified oligonucleotide has a nucleobase sequence consisting of the nucleobase sequence TCCCTCCGTCTGCTTAGTTAGAA (SEQ ID NO: 40).

In certain embodiments, a modified oligonucleotide has a nucleobase sequence that is complementary to a nucleobase sequence of a pre-miR sequence comprising a mature miRNA selected from miR-21, miR-125a-5p, miR-191, miR-210, miR-222, miR-378, miR-423-3p, and miR-638.

In certain embodiments, a modified oligonucleotide has a nucleobase sequence that is complementary to a nucleobase sequence of a pri-miR sequence comprising a mature miRNA selected from miR-21, miR-125a-5p, miR-191, miR-210, miR-222, miR-378, miR-423-3p, and miR-638.

In certain embodiments, a modified oligonucleotide has a nucleobase sequence that is complementary to a nucleobase sequence of a pri-miR sequence comprising a mature miRNA selected from miR-181a, miR-181a*, and miR-181b. In certain embodiments, a modified oligonucleotide has a nucleobase sequence that is complementary to a nucleobase sequence of a pre-miR sequence comprising a mature miRNA selected from miR-181a, miR-181a*, and miR-181b.

In certain embodiments, a modified oligonucleotide has a nucleobase sequence that is complementary to a nucleobase sequence having at least 80% identity to a nucleobase sequence of a miR stem-loop sequence selected from SEQ ID NO: 1, 2, 3, 4, 5, 6, 7, and 8. In certain embodiments, a modified oligonucleotide has a nucleobase sequence that is complementary to a nucleobase sequence having at least 85%, at least 90%, at least 92%, at least 94%, at least 96%, at least 98% identity, or 100% identity to a nucleobase sequence of a miR stem-loop sequence selected from SEQ ID NOs 1, 2, 3, 4, 5, 6, 7, and 8.

In certain embodiments, a modified oligonucleotide has a nucleobase sequence that is complementary to a nucleobase sequence having at least 80% identity to a nucleobase sequence of a miRNA having a nucleobase sequence selected from SEQ ID NO: 9, 10, 11, 12, 13, 14, 15, and 16. In certain embodiments, a modified oligonucleotide has a nucleobase sequence that is complementary to a nucleobase sequence having at least 85%, at least 90%, at least 92%, at least 94%, at least 96%, at least 98% identity, or 100% identity to a nucleobase sequence of a miRNA nucleobase sequence selected from SEQ ID NOs 9, 10, 11, 12, 13, 14, 15, and 16.

In certain embodiments, a modified oligonucleotide has a nucleobase sequence that is complementary to a nucleobase sequence having at least 80% identity to a nucleobase sequence of a miR stem-loop sequence selected from SEQ ID NO: 34, 35, 36, and 37. In certain embodiments, a modified oligonucleotide has a nucleobase sequence that is complementary to a nucleobase sequence having at least 85%, at least 90%, at least 92%, at least 94%, at least 96%, at least 98% identity, or 100% identity to a nucleobase sequence of a miR stem-loop sequence selected from SEQ ID NOs 34, 35, 36, and 37.

In certain embodiments, a modified oligonucleotide has a nucleobase sequence that is complementary to a nucleobase sequence having at least 80% identity to a nucleobase sequence of a miRNA having a nucleobase sequence selected from SEQ ID NO: 31, 32, and 33. In certain embodiments, a modified oligonucleotide has a nucleobase sequence that is complementary to a nucleobase sequence having at least 85%, at least 90%, at least 92%, at least 94%, at least 96%, at least 98% identity, or 100% identity to a nucleobase sequence of a miRNA nucleobase sequence selected from SEQ ID NOs 31, 32, and 33.

In certain embodiments, a nucleobase sequence of a modified oligonucleotide is fully complementary to a miRNA nucleobase sequence listed herein, or a precursor thereof. In certain embodiments, a modified oligonucleotide has a nucleobase sequence having one mismatch with respect to the nucleobase sequence of the mature miRNA, or a precursor thereof. In certain embodiments, a modified oligonucleotide has a nucleobase sequence having two mismatches with respect to the nucleobase sequence of the miRNA, or a precursor thereof. In certain such embodiments, a modified oligonucleotide has a nucleobase sequence having no more than two mismatches with respect to the nucleobase sequence of the mature miRNA, or a precursor thereof. In certain such embodiments, the mismatched nucleobases are contiguous. In certain such embodiments, the mismatched nucleobases are not contiguous.

In certain embodiments, a modified oligonucleotide consists of a number of linked nucleosides that is equal to the length of the mature miR to which it is complementary.

In certain embodiments, the number of linked nucleosides of a modified oligonucleotide is less than the length of the mature miRNA to which it is complementary. In certain such embodiments, the number of linked nucleosides of a modified oligonucleotide is one less than the length of the mature miR to which it is complementary. In certain such embodiments, a modified oligonucleotide has one less nucleoside at the 5' terminus. In certain such embodiments, a modified oligonucleotide has one less nucleoside at the 3' terminus. In certain such embodiments, a modified oligonucleotide has two fewer nucleosides at the 5' terminus. In certain such embodiments, a modified oligonucleotide has two fewer nucleosides at the 3' terminus. A modified oligonucleotide having a number of linked nucleosides that is less than the length of the miRNA, wherein each nucleobase of a modified oligonucleotide is complementary to each nucleobase at a corresponding position in a miRNA, is considered to be a modified oligonucleotide having a nucleobase sequence that is fully complementary to a portion of a miRNA sequence.

In certain embodiments, the number of linked nucleosides of a modified oligonucleotide is greater than the length of the miRNA to which it is complementary. In certain such embodiments, the nucleobase of an additional nucleoside is complementary to a nucleobase of a miRNA stem-loop sequence. In certain embodiments, the number of linked nucleosides of a modified oligonucleotide is one greater than the length of the miRNA to which it is complementary. In certain such embodiments, the additional nucleoside is at the 5' terminus of a modified oligonucleotide. In certain such embodiments, the additional nucleoside is at the 3' terminus of a modified oligonucleotide. In certain embodiments, the number of linked nucleosides of a modified oligonucleotide is two greater than the length of the miRNA to which it is complementary. In certain such embodiments, the two additional nucleosides are at the 5' terminus of a modified oligonucleotide. In certain such embodiments, the two additional nucleosides are at the 3' terminus of a modified oligonucleotide. In certain such embodiments, one additional nucleoside is located at the 5' terminus and one additional nucleoside is located at the 3' terminus of a modified oligonucleotide.

In certain embodiments, a portion of the nucleobase sequence of a modified oligonucleotide is fully complementary to the nucleobase sequence of the miRNA, but the entire modified oligonucleotide is not fully complementary to the miRNA. In certain such embodiments, the number of nucleosides of a modified oligonucleotide having a fully complementary portion is greater than the length of the miRNA. For example, a modified oligonucleotide consisting of 24 linked nucleosides, where the nucleobases of nucleosides 1 through 23 are each complementary to a corresponding position of a miRNA that is 23 nucleobases in length, has a 23 nucleoside portion that is fully complementary to the nucleobase sequence of the miRNA and approximately 96% overall complementarity to the nucleobase sequence of the miRNA.

In certain embodiments, the nucleobase sequence of a modified oligonucleotide is fully complementary to a portion of the nucleobase sequence of a miRNA. For example, a modified oligonucleotide consisting of 22 linked nucleosides, where the nucleobases of nucleosides 1 through 22 are each complementary to a corresponding position of a miRNA that is 23 nucleobases in length, is fully complementary to a 22 nucleobase portion of the nucleobase sequence of a miRNA. Such a modified oligonucleotide has approximately 96% overall complementarity to the nucleobase sequence of the entire miRNA, and has 100% complementarity to a 22 nucleobase portion of the miRNA.

In certain embodiments, a portion of the nucleobase sequence of a modified oligonucleotide is fully complementary to a portion of the nucleobase sequence of a miRNA, or a precursor thereof. In certain such embodiments, 15 contiguous nucleobases of a modified oligonucleotide are each complementary to 15 contiguous nucleobases of a miRNA, or a precursor thereof. In certain such embodiments, 16 contiguous nucleobases of a modified oligonucleotide are each complementary to 16 contiguous nucleobases of a miRNA, or a precursor thereof. In certain such embodiments, 17 contiguous nucleobases of a modified oligonucleotide are each complementary to 17 contiguous nucleobases of a miRNA, or a precursor thereof. In certain such embodiments, 18 contiguous nucleobases of a modified oligonucleotide are each complementary to 18 contiguous nucleobases of a miRNA, or a precursor thereof. In certain such embodiments, 19 contiguous nucleobases of a modified oligonucleotide are each complementary to 19 contiguous nucleobases of a miRNA, or a precursor thereof. In certain such embodiments, 20 contiguous nucleobases of a modified oligonucleotide are each complementary to 20 contiguous nucleobases of a miRNA, or a precursor thereof. In certain such embodiments, 22 contiguous nucleobases of a modified oligonucleotide are each complementary to 22 contiguous nucleobases of a miRNA, or a precursor thereof. In certain such embodiments, 23 contiguous nucleobases of a modified oligonucleotide are each complementary to 23 contiguous nucleobases of a miRNA, or a precursor thereof. In certain such embodiments, 24 contiguous nucleobases of a modified oligonucleotide are each complementary to 24 contiguous nucleobases of a miRNA, or a precursor thereof.

The nucleobase sequences set forth herein, including but not limited to those found in the Examples and in the sequence listing, are independent of any modification to the nucleic acid. As such, nucleic acids defined by a SEQ ID NO may comprise, independently, one or more modifications to one or more sugar moieties, to one or more internucleoside linkages, and/or to one or more nucleobases.

Although the sequence listing accompanying this filing identifies each nucleobase sequence as either "RNA" or "DNA" as required, in reality, those sequences may be modified with any combination of chemical modifications. One of skill in the art will readily appreciate that such designation as "RNA" or "DNA" to describe modified oligonucleotides is somewhat arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified bases, such as "AT$^{me}$CGAUCG," wherein $^{me}$C indicates a cytosine base comprising a methyl group at the 5-position.

Nucleic acids described herein by Isis Number (Isis NO.) comprise a combination of nucleobase sequence and certain identified modifications.

Certain Modified Oligonucleotides

In certain embodiments, a modified oligonucleotide consists of 15 to 30 linked nucleosides. In certain embodiments, a modified oligonucleotide consists of 19 to 24 linked nucleosides. In certain embodiments, a modified oligonucleotide consists of 21 to 24 linked nucleosides. In certain embodiments, a modified oligonucleotide consists of 15 linked nucleosides. In certain embodiments, a modified oligonucleotide consists of 16 linked nucleosides. In certain embodiments, a modified oligonucleotide consists of 17 linked nucleosides. In certain embodiments, a modified oligonucleotide consists of 18 linked nucleosides. In certain embodiments, a modified oligonucleotide consists of 19 linked nucleosides. In certain embodiments, a modified oligonucleotide consists of 20 linked nucleosides. In certain embodiments, a modified oligonucleotide consists of 21 linked nucleosides. In certain embodiments, a modified oligonucleotide consists of 22 linked nucleosides. In certain embodiments, a modified oligonucleotide consists of 23 linked nucleosides. In certain embodiments, a modified oligonucleotide consists of 24 linked nucleosides. In certain embodiments, a modified oligonucleotide consists of 25 linked nucleosides. In certain embodiments, a modified oligonucleotide consists of 26 linked nucleosides. In certain embodiments, a modified oligonucleotide consists of 27 linked nucleosides. In certain embodiments, a modified oligonucleotide consists of 28 linked nucleosides. In certain embodiments, a modified oligonucleotide consists of 29 linked nucleosides. In certain embodiments, a modified oligonucleotide consists of 30 linked nucleosides.

Certain Modifications

Modified oligonucleotides of the present invention comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide of the present invention comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N(R$_1$)—, —C(R$_1$)(R$_2$)—, —C(R$_1$)=C(R$_1$)—, —C(R$_1$)=

N—, —C(=NR$_1$)—, —Si(R$_1$)(R$_2$)—, —S(=O)$_2$—, —S(=O)—, —C(=O)— and —C(=S)—; where each R$_1$ and R$_2$ is, independently, H, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is, independently, halogen, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, amino, substituted amino, acyl, substituted acyl, C$_1$-C$_{12}$ aminoalkyl, C$_1$-C$_{12}$ aminoalkoxy, substituted C$_1$-C$_{12}$ aminoalkyl, substituted C$_1$-C$_{12}$ aminoalkoxy or a protecting group.

In some embodiments, the bicyclic sugar moiety is bridged between the 2' and 4' carbon atoms with a biradical group selected from —O—(CH$_2$)$_p$—, —O—CH$_2$—, —O—CH$_2$CH$_2$—, —O—CH(alkyl)-, —NH—(CH$_2$)$_p$—, —N(alkyl)-(CH$_2$)$_p$—, —O—CH(alkyl)-, —(CH(alkyl))-(CH$_2$)$_p$—, —NH—O—(CH$_2$)$_p$—, —N(alkyl)-O—(CH$_2$)$_p$—, or —O—N(alkyl)-(CH$_2$)$_p$—, wherein p is 1, 2, 3, 4 or 5 and each alkyl group can be further substituted. In certain embodiments, p is 1, 2 or 3.

In certain embodiments, a 2'-modified nucleoside comprises a 2'-substituent group selected from halo, allyl, amino, azido, SH, CN, OCN, CF$_3$, OCF$_3$, O—, S—, or N(R$_m$)-alkyl; O—, S—, or N(R$_m$)-alkenyl; O—, S— or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-modified nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), —O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-modified nucleoside comprises a 2'-substituent group selected from F, OCF$_3$, O—CH$_3$, OCH$_2$CH$_2$OCH$_3$, 2'-O(CH$_2$)$_2$SCH$_3$, O—(CH$_2$)$_2$—O—N(CH$_3$)$_2$, —O(CH$_2$)$_2$O(CH$_2$)$_2$N—(CH$_3$)$_2$, and O—CH$_2$—C(=O)—N(H)CH$_3$.

In certain embodiments, a 2'-modified nucleoside comprises a 2'-substituent group selected from F, O—CH$_3$, and OCH$_2$CH$_2$OCH$_3$.

In certain embodiments, a sugar-modified nucleoside is a 4'-thio modified nucleoside. In certain embodiments, a sugar-modified nucleoside is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-OCH$_3$, 2'-O—(CH$_2$)$_2$—OCH$_3$, and 2'-F.

In certain embodiments, a modified oligonucleotide of the present invention comprises one or more internucleoside modifications. In certain such embodiments, each internucleoside linkage of a modified oligonucleotide is a modified internucleoside linkage. In certain embodiments, a modified internucleoside linkage comprises a phosphorus atom.

In certain embodiments, a modified oligonucleotide of the present invention comprises at least one phosphorothioate internucleoside linkage. In certain embodiments, each internucleoside linkage of a modified oligonucleotide is a phosphorothioate internucleoside linkage.

In certain embodiments, a modified internucleoside linkage does not comprise a phosphorus atom. In certain such embodiments, an internucleoside linkage is formed by a short chain alkyl internucleoside linkage. In certain such embodiments, an internucleoside linkage is formed by a cycloalkyl internucleoside linkages. In certain such embodiments, an internucleoside linkage is formed by a mixed heteroatom and alkyl internucleoside linkage. In certain such embodiments, an internucleoside linkage is formed by a mixed heteroatom and cycloalkyl internucleoside linkages. In certain such embodiments, an internucleoside linkage is formed by one or more short chain heteroatomic internucleoside linkages. In certain such embodiments, an internucleoside linkage is formed by one or more heterocyclic internucleoside linkages. In certain such embodiments, an internucleoside linkage has an amide backbone. In certain such embodiments, an internucleoside linkage has mixed N, O, S and CH$_2$ component parts.

In certain embodiments, a modified oligonucleotide comprises one or more modified nucleobases. In certain embodiments, a modified oligonucleotide comprises one or more 5-methylcytosines. In certain embodiments, each cytosine of a modified oligonucleotide comprises a 5-methylcytosine.

In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and 0-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

Certain Oligonucleotide Motifs

Suitable motifs for modified oligonucleotides of the present invention include, but are not limited to, fully modified, uniformly modified, positionally modified, and gapmer. Modified oligonucleotides having a fully modified motif, including a uniformly modified motif, may be designed to target mature miRNAs. Alternatively, modified oligonucleotides having a fully modified motif, including a uniformly modified motif, may be designed to target certain sites of pri-miRNAs or pre-miRNAs, to block the processing of miRNA precursors into mature miRNAs. Modified oligonucleotides having a fully modified motif or uniformly modified motif are effective inhibitors of miRNA activity.

In certain embodiments, a fully modified oligonucleotide comprises a sugar modification at each nucleoside. In certain such embodiments, pluralities of nucleosides are 2'-O- methoxyethyl nucleosides and the remaining nucleosides are 2'-fluoro nucleosides. In certain such embodiments, each of a plurality of nucleosides is a 2'-O-methoxyethyl nucleoside and each of a plurality of nucleosides is a bicyclic nucleoside. In certain such embodiments, a fully modified oligonucleotide further comprises at least one modified internucleoside linkage. In certain such embodiments, each internucleoside linkage of a fully sugar-modified oligonucleotide is a modified internucleoside linkage. In certain embodiments, a fully sugar-modified oligonucleotide further comprises at least one phosphorothioate internucleoside linkage. In certain such embodiments, each internucleoside linkage of a fully sugar-modified oligonucleotide is a phosphorothioate internucleoside linkage.

In certain embodiments, a fully modified oligonucleotide is modified at each internucleoside linkage. In certain such embodiments, each internucleoside linkage of a fully modified oligonucleotide is a phosphorothioate internucleoside linkage.

In certain embodiments, a uniformly modified oligonucleotide comprises the same sugar modification at each nucleoside. In certain such embodiments, each nucleoside of a modified oligonucleotide comprises a 2'-O-methoxyethyl sugar modification. In certain embodiments, each nucleoside of a modified oligonucleotide comprises a 2'-O-methyl sugar modification. In certain embodiments, each nucleoside of a modified oligonucleotide comprises a 2'-fluoro sugar modification. In certain such embodiments, a uniformly modified oligonucleotide further comprises at least one modified internucleoside linkage. In certain such embodiments, each internucleoside linkage of a uniformly sugar-modified oligonucleotide is a modified internucleoside linkage. In certain embodiments, a uniformly sugar-modified oligonucleotide further comprises at least one phosphorothioate internucleoside linkage. In certain such embodiments, each internucleoside linkage of a uniformly sugar-modified oligonucleotide is a phosphorothioate internucleoside linkage.

In certain embodiments, a uniformly modified oligonucleoside comprises the same internucleoside linkage modifications throughout. In certain such embodiments, each internucleoside linkage of a uniformly modified oligonucleotide is a phosphorothioate internucleoside linkage.

Table 1 illustrates certain uniformly modified oligonucleotides complementary to the miRNAs described herein. Each nucleoside comprises a 2'-O-methoxyethyl sugar, each internucleoside linkage is phosphorothioate, and each cytosine is a 5-methylcytosine.

TABLE 1

| Modified Oligonucleotide # | SEQ ID NO | miRNA | Version 10 Sanger mir ID |
|---|---|---|---|
| 327917 | 1 | miR-21 | hsa-miR-21 |
| 341787 | 2 | miR-125a | hsa-miR-125a-5p |
| 341802 | 3 | mir-191 | hsa-miR-191 |
| 401852 | 4 | mir-210 | hsa-miR-210 |
| 327920 | 5 | mir-222 | hsa-miR-222 |
| 379242 | 6 | miR-422b | hsa-miR-378 |
| 379243 | 7 | mir-423 | hsa-miR-423-3p |
| 399329 | 8 | miR-638 | hsa-miR-638 |

In certain embodiments, a positionally modified oligonucleotide comprises regions of linked nucleosides, where each nucleoside of each region comprises the same sugar moiety, and where each nucleoside of each region comprises a sugar moiety different from that of an adjacent region.

In certain embodiments, a positionally modified oligonucleotide comprises at least 10 2'-fluoro modified nucleosides. Such a positionally modified oligonucleotide may be represented by the following formula I:

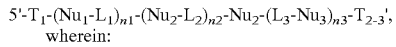

wherein:

each $Nu_1$ and $Nu_3$ is, independently, a stabilizing nucleoside;

at least 10 $Nu_2$ are 2'-fluoro nucleosides;

each $L_1$, $L_2$ and $L_3$ is, independently, an internucleoside linkage;

each $T_1$ and $T_2$ is, independently, H, a hydroxyl protecting group, an optionally linked conjugate group or a capping group;

$n_1$ is from 0 to about 3;

$n_2$ is from about 14 to about 22;

$n_3$ is from 0 to about 3; and provided that dm is 0 then $T_1$ is not H or a hydroxyl protecting group, and if $n_3$ is 0, then $T_2$ is not H or a hydroxyl protecting group.

In certain such embodiments, $n_1$ and $n_3$ are each, independently, from 1 to about 3. In certain embodiments, $n_1$ and $n_3$ are each, independently, from 2 to about 3. In certain embodiments, $n_1$ is 1 or 2 and $n_3$ is 2 or 3. In certain embodiments, $n_1$ and $n_3$ are each 2. In certain embodiments, at least one of $n_1$ and $n_3$ is greater than zero. In certain embodiments, $n_1$ and $n_3$ is each greater than zero. In certain embodiments, one of $n_1$ and $n_3$ is greater than zero. In certain embodiments, one of $n_1$ and $n_3$ is greater than one.

In certain embodiments, $n_2$ is from 16 to 20. In certain embodiments, $n_2$ is from 17 to 19. In certain embodiments, $n_2$ is 18. In certain embodiments, $n_2$ is 19. In certain embodiments, $n_2$ is 20.

In certain embodiments, about 2 to about 8 of the $Nu_2$ nucleosides are stabilizing nucleosides. In certain embodiments, from about 2 to about 6 of the $Nu_2$ nucleosides are stabilizing nucleosides. In certain embodiments, from about 3 to about 4 of the $Nu_2$ nucleosides are stabilizing nucleosides. In certain embodiments, 3 of the $Nu_2$ nucleosides are stabilizing nucleosides.

In certain embodiments, each of the $Nu_2$ stabilizing nucleosides is separated from the $Nu_3$ stabilizing nucleosides by from 2 to about 8 2'-fluoro nucleosides. In certain embodiments each of the $Nu_2$ stabilizing nucleosides is separated from the $Nu_3$ stabilizing nucleosides by from 3 to about 8 2'-fluoro nucleosides. In certain embodiments each of the $Nu_2$ stabilizing nucleosides is separated from the $Nu_3$ stabilizing nucleosides by from 5 to about 8 2'-fluoro nucleosides.

In certain embodiments, a modified oligonucleotide comprises from 2 to about 6 $Nu_2$ stabilizing nucleosides. In certain embodiments, a modified oligonucleotide comprises 3 $Nu_2$ stabilizing nucleosides.

In certain embodiments, each of the $Nu_2$ stabilizing nucleosides is linked together in one contiguous sequence. In certain embodiments, at least two of the $Nu_2$ stabilizing nucleosides are separated by at least one of the 2'-fluoro nucleosides. In certain embodiments, each of the $Nu_2$ stabilizing nucleosides is separated by at least one of the 2'-fluoro nucleosides.

In certain embodiments, at least two contiguous sequences of the $Nu_2$ 2'-fluoro nucleosides are separated by at least one of the stabilizing nucleosides wherein each of the contiguous sequences have the same number of 2'-fluoro nucleosides.

In certain embodiments, $T_1$ and $T_2$ are each, independently, H or a hydroxyl protecting group. In certain embodiments, at least one of $T_1$ and $T_2$ is 4,4'-dimethoxytrityl. In certain embodiments, at least one of $T_1$ and $T_2$ is an optionally linked conjugate group. In certain embodiments, at least one of $T_1$ and $T_2$ is a capping group. In certain embodiments, the capping group is an inverted deoxy abasic group.

In certain embodiments, a positionally modified oligonucleotide comprises at least one modified internucleoside linkage. In certain such embodiments, each internucleoside linkage of a positionally modified oligonucleoside is a modified internucleoside linkage. In certain embodiments, at least one internucleoside linkage of a positionally modified oligonucleotide is a phosphorothioate internucleoside linkage. In certain such embodiments, each internucleoside linkage of a positionally modified oligonucleotide is a phosphorothioate internucleoside linkage.

In certain embodiments, a positionally modified motif is represented by the following formula II, which represents a modified oligonucleotide consisting of linked nucleosides:

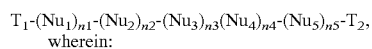

$T_1$-$(Nu_1)_{n1}$-$(Nu_2)_{n2}$-$(Nu_3)_{n3}$$(Nu_4)_{n4}$-$(Nu_5)_{n5}$-$T_2$,
wherein:

$Nu_1$ and $Nu_5$ are, independently, 2' stabilizing nucleosides;
$Nu_2$ and $Nu_4$ are 2'-fluoro nucleosides;
$Nu_3$ is a 2'-modified nucleoside;
each of $n_1$ and $n_5$ is, independently, from 0 to 3;
the sum of $n_2$ plus $n_4$ is between 10 and 25;
$n_3$ is from 0 and 5; and
each $T_1$ and $T_2$ is, independently, H, a hydroxyl protecting group, an optionally linked conjugate group or a capping group.

In certain embodiments, the sum of $n_2$ and $n_4$ is 16. In certain embodiments, the sum of $n_2$ and $n_4$ is 17. In certain embodiments, the sum of $n_2$ and $n_4$ is 18. In certain embodiments, $n_1$ is 2; $n_3$ is 2 or 3; and $n_5$ is 2.

In certain embodiments, $Nu_1$ and $Nu_5$ are, independently, 2'-modified nucleosides.

In certain embodiments, $Nu_1$ is O—$(CH_2)_2$—$OCH_3$, $Nu_3$ is O—$(CH_2)_2$—$OCH_3$, $Nu_5$ O—$(CH_2)_2$—$OCH_3$, $T_1$ is H and $T_2$ is H.

In certain embodiments, a modified oligonucleotide complementary to a miRNA and consisting of 21 linked nucleosides has a Formula II selected from Table 2, where each internucleoside linkage is a phosphorothioate internucleoside linkage. In certain embodiments, a modified oligonucleotide having a Formula II selected from Table 2 has a nucleobase sequence selected from the nucleobase sequences recited in SEQ ID NOs 24 and 27.

TABLE 2

| $n_1$ | $n_2$ | $n_3$ | $n_4$ | $n_5$ | $Nu_1$ | $Nu_3$ | $Nu_5$ | $T_1$ | $T_2$ |
|---|---|---|---|---|---|---|---|---|---|
| 2 | 17 | 0 | 0 | 2 | 2'-MOE | 2'-MOE | 2'-MOE | H | H |
| 2 | 2 | 2 | 13 | 2 | 2'-MOE | 2'-MOE | 2'-MOE | H | H |
| 2 | 3 | 2 | 12 | 2 | 2'-MOE | 2'-MOE | 2'-MOE | H | H |
| 2 | 4 | 2 | 11 | 2 | 2'-MOE | 2'-MOE | 2'-MOE | H | H |
| 2 | 5 | 2 | 10 | 2 | 2'-MOE | 2'-MOE | 2'-MOE | H | H |
| 2 | 6 | 2 | 9 | 2 | 2'-MOE | 2'-MOE | 2'-MOE | H | H |
| 2 | 7 | 2 | 8 | 2 | 2'-MOE | 2'-MOE | 2'-MOE | H | H |
| 2 | 8 | 2 | 7 | 2 | 2'-MOE | 2'-MOE | 2'-MOE | H | H |
| 2 | 9 | 2 | 6 | 2 | 2'-MOE | 2'-MOE | 2'-MOE | H | H |

TABLE 2 -continued

| $n_1$ | $n_2$ | $n_3$ | $n_4$ | $n_5$ | $Nu_1$ | $Nu_3$ | $Nu_5$ | $T_1$ | $T_2$ |
|---|---|---|---|---|---|---|---|---|---|
| 2 | 10 | 2 | 5 | 2 | 2'-MOE | 2'-MOE | 2'-MOE | H | H |
| 2 | 11 | 2 | 4 | 2 | 2'-MOE | 2'-MOE | 2'-MOE | H | H |
| 2 | 12 | 2 | 3 | 2 | 2'-MOE | 2'-MOE | 2'-MOE | H | H |
| 2 | 13 | 2 | 2 | 2 | 2'-MOE | 2'-MOE | 2'-MOE | H | H |
| 2 | 2 | 3 | 12 | 2 | 2'-MOE | 2'-MOE | 2'-MOE | H | H |
| 2 | 3 | 3 | 11 | 2 | 2'-MOE | 2'-MOE | 2'-MOE | H | H |
| 2 | 4 | 3 | 10 | 2 | 2'-MOE | 2'-MOE | 2'-MOE | H | H |
| 2 | 5 | 3 | 9 | 2 | 2'-MOE | 2'-MOE | 2'-MOE | H | H |
| 2 | 6 | 3 | 8 | 2 | 2'-MOE | 2'-MOE | 2'-MOE | H | H |
| 2 | 7 | 3 | 7 | 2 | 2'-MOE | 2'-MOE | 2'-MOE | H | H |
| 2 | 8 | 3 | 6 | 2 | 2'-MOE | 2'-MOE | 2'-MOE | H | H |
| 2 | 9 | 3 | 5 | 2 | 2'-MOE | 2'-MOE | 2'-MOE | H | H |
| 2 | 10 | 3 | 4 | 2 | 2'-MOE | 2'-MOE | 2'-MOE | H | H |
| 2 | 11 | 3 | 3 | 2 | 2'-MOE | 2'-MOE | 2'-MOE | H | H |
| 2 | 12 | 3 | 2 | 2 | 2'-MOE | 2'-MOE | 2'-MOE | H | H |
| 2 | 8 | 6 | 3 | 2 | 2'-MOE | 2'-MOE | 2'-MOE | H | H |

In certain embodiments, a modified oligonucleotide complementary to a miRNA and consisting of 22 linked nucleosides has a Formula II selected from Table 3, where each internucleoside linkage is a phosphorothioate internucleoside linkage. In certain embodiments, a modified oligonucleotide having a Formula II selected from Table 3 has a nucleobase sequence selected from the nucleobase sequences recited in SEQ ID NOs 17, 20, 22, 26, and 28.

TABLE 3

| $n_1$ | $n_2$ | $n_3$ | $n_4$ | $n_5$ | $Nu_1$ | $Nu_3$ | $Nu_5$ | $T_1$ | $T_2$ |
|---|---|---|---|---|---|---|---|---|---|
| 2 | 18 | 0 | 0 | 2 | 2'-MOE | 2'-MOE | 2'-MOE | H | H |
| 2 | 2 | 2 | 14 | 2 | 2'-MOE | 2'-MOE | 2'-MOE | H | H |
| 2 | 3 | 2 | 13 | 2 | 2'-MOE | 2'-MOE | 2'-MOE | H | H |
| 2 | 4 | 2 | 12 | 2 | 2'-MOE | 2'-MOE | 2'-MOE | H | H |
| 2 | 5 | 2 | 11 | 2 | 2'-MOE | 2'-MOE | 2'-MOE | H | H |
| 2 | 6 | 2 | 10 | 2 | 2'-MOE | 2'-MOE | 2'-MOE | H | H |
| 2 | 7 | 2 | 9 | 2 | 2'-MOE | 2'-MOE | 2'-MOE | H | H |
| 2 | 8 | 2 | 8 | 2 | 2'-MOE | 2'-MOE | 2'-MOE | H | H |
| 2 | 9 | 2 | 7 | 2 | 2'-MOE | 2'-MOE | 2'-MOE | H | H |
| 2 | 10 | 2 | 6 | 2 | 2'-MOE | 2'-MOE | 2'-MOE | H | H |
| 2 | 11 | 2 | 5 | 2 | 2'-MOE | 2'-MOE | 2'-MOE | H | H |
| 2 | 12 | 2 | 4 | 2 | 2'-MOE | 2'-MOE | 2'-MOE | H | H |
| 2 | 13 | 2 | 3 | 2 | 2'-MOE | 2'-MOE | 2'-MOE | H | H |
| 2 | 14 | 2 | 2 | 2 | 2'-MOE | 2'-MOE | 2'-MOE | H | H |
| 2 | 2 | 3 | 13 | 2 | 2'-MOE | 2'-MOE | 2'-MOE | H | H |

TABLE 3 -continued

| $n_1$ | $n_2$ | $n_3$ | $n_4$ | $n_5$ | $Nu_1$ | $Nu_3$ | $Nu_5$ | $T_1$ | $T_2$ |
|---|---|---|---|---|---|---|---|---|---|
| 2 | 3 | 3 | 12 | 2 | 2'-MOE | 2'-MOE | 2'-MOE | H | H |
| 2 | 4 | 3 | 11 | 2 | 2'-MOE | 2'-MOE | 2'-MOE | H | H |
| 2 | 5 | 3 | 10 | 2 | 2'-MOE | 2'-MOE | 2'-MOE | H | H |
| 2 | 6 | 3 | 9 | 2 | 2'-MOE | 2'-MOE | 2'-MOE | H | H |
| 2 | 7 | 3 | 8 | 2 | 2'-MOE | 2'-MOE | 2'-MOE | H | H |
| 2 | 8 | 3 | 7 | 2 | 2'-MOE | 2'-MOE | 2'-MOE | H | H |
| 2 | 9 | 3 | 6 | 2 | 2'-MOE | 2'-MOE | 2'-MOE | H | H |
| 2 | 10 | 3 | 5 | 2 | 2'-MOE | 2'-MOE | 2'-MOE | H | H |
| 2 | 11 | 3 | 4 | 2 | 2'-MOE | 2'-MOE | 2'-MOE | H | H |
| 2 | 12 | 3 | 3 | 2 | 2'-MOE | 2'-MOE | 2'-MOE | H | H |
| 2 | 13 | 3 | 2 | 2 | 2'-MOE | 2'-MOE | 2'-MOE | H | H |
| 2 | 8 | 6 | 4 | 2 | 2'-MOE | 2'-MOE | 2'-MOE | H | H |

In certain embodiments, a modified oligonucleotide complementary to a miRNA and consisting of 23 linked nucleosides has a Formula II selected from Table 4, where each internucleoside linkage is a phosphorothioate internucleoside linkage. In certain embodiments, a modified oligonucleotide having a Formula II selected from Table 4 has a nucleobase sequence selected from the nucleobase sequences recited in SEQ ID NOs 18, 21, and 23.

TABLE 4

| $n_1$ | $n_2$ | $n_3$ | $n_4$ | $n_5$ | $Nu_1$ | $Nu_3$ | $Nu_5$ | $T_1$ | $T_2$ |
|---|---|---|---|---|---|---|---|---|---|
| 2 | 19 | 0 | 0 | 2 | 2'-MOE | 2'-MOE | 2'-MOE | H | H |
| 2 | 2 | 2 | 15 | 2 | 2'-MOE | 2'-MOE | 2'-MOE | H | H |
| 2 | 3 | 2 | 14 | 2 | 2'-MOE | 2'-MOE | 2'-MOE | H | H |
| 2 | 4 | 2 | 13 | 2 | 2'-MOE | 2'-MOE | 2'-MOE | H | H |
| 2 | 5 | 2 | 12 | 2 | 2'-MOE | 2'-MOE | 2'-MOE | H | H |
| 2 | 6 | 2 | 11 | 2 | 2'-MOE | 2'-MOE | 2'-MOE | H | H |
| 2 | 7 | 2 | 10 | 2 | 2'-MOE | 2'-MOE | 2'-MOE | H | H |
| 2 | 8 | 2 | 9 | 2 | 2'-MOE | 2'-MOE | 2'-MOE | H | H |
| 2 | 9 | 2 | 8 | 2 | 2'-MOE | 2'-MOE | 2'-MOE | H | H |
| 2 | 10 | 2 | 7 | 2 | 2'-MOE | 2'-MOE | 2'-MOE | H | H |
| 2 | 11 | 2 | 6 | 2 | 2'-MOE | 2'-MOE | 2'-MOE | H | H |
| 2 | 12 | 2 | 5 | 2 | 2'-MOE | 2'-MOE | 2'-MOE | H | H |
| 2 | 13 | 2 | 4 | 2 | 2'-MOE | 2'-MOE | 2'-MOE | H | H |
| 2 | 14 | 2 | 3 | 2 | 2'-MOE | 2'-MOE | 2'-MOE | H | H |
| 2 | 15 | 2 | 2 | 2 | 2'-MOE | 2'-MOE | 2'-MOE | H | H |
| 2 | 2 | 3 | 14 | 2 | 2'-MOE | 2'-MOE | 2'-MOE | H | H |
| 2 | 3 | 3 | 13 | 2 | 2'-MOE | 2'-MOE | 2'-MOE | H | H |
| 2 | 4 | 3 | 12 | 2 | 2'-MOE | 2'-MOE | 2'-MOE | H | H |
| 2 | 5 | 3 | 11 | 2 | 2'-MOE | 2'-MOE | 2'-MOE | H | H |
| 2 | 6 | 3 | 10 | 2 | 2'-MOE | 2'-MOE | 2'-MOE | H | H |
| 2 | 7 | 3 | 9 | 2 | 2'-MOE | 2'-MOE | 2'-MOE | H | H |
| 2 | 8 | 3 | 8 | 2 | 2'-MOE | 2'-MOE | 2'-MOE | H | H |
| 2 | 9 | 3 | 7 | 2 | 2'-MOE | 2'-MOE | 2'-MOE | H | H |
| 2 | 10 | 3 | 6 | 2 | 2'-MOE | 2'-MOE | 2'-MOE | H | H |
| 2 | 11 | 3 | 5 | 2 | 2'-MOE | 2'-MOE | 2'-MOE | H | H |
| 2 | 12 | 3 | 4 | 2 | 2'-MOE | 2'-MOE | 2'-MOE | H | H |
| 2 | 13 | 3 | 3 | 2 | 2'-MOE | 2'-MOE | 2'-MOE | H | H |
| 2 | 14 | 3 | 2 | 2 | 2'-MOE | 2'-MOE | 2'-MOE | H | H |
| 2 | 8 | 6 | 5 | 2 | 2'-MOE | 2'-MOE | 2'-MOE | H | H |

In certain embodiments, a modified oligonucleotide complementary to a miRNA and consisting of 24 linked nucleosides has a Formula II selected from Table 5, where each internucleoside linkage is a phosphorothioate internucleoside linkage. In certain embodiments, a modified oligonucleotide having a Formula II selected from Table 5 has a nucleobase sequence selected from the nucleobase sequences recited in SEQ ID NOs 19 and 23.

TABLE 5

| $n_1$ | $n_2$ | $n_3$ | $n_4$ | $n_5$ | $Nu_1$ | $Nu_3$ | $Nu_5$ | $T_1$ | $T_2$ |
|---|---|---|---|---|---|---|---|---|---|
| 2 | 20 | 0 | 0 | 2 | 2'-MOE | 2'-MOE | 2'-MOE | H | H |
| 2 | 2 | 2 | 16 | 2 | 2'-MOE | 2'-MOE | 2'-MOE | H | H |
| 2 | 3 | 2 | 15 | 2 | 2'-MOE | 2'-MOE | 2'-MOE | H | H |
| 2 | 4 | 2 | 14 | 2 | 2'-MOE | 2'-MOE | 2'-MOE | H | H |
| 2 | 5 | 2 | 13 | 2 | 2'-MOE | 2'-MOE | 2'-MOE | H | H |
| 2 | 6 | 2 | 12 | 2 | 2'-MOE | 2'-MOE | 2'-MOE | H | H |
| 2 | 7 | 2 | 11 | 2 | 2'-MOE | 2'-MOE | 2'-MOE | H | H |
| 2 | 8 | 2 | 10 | 2 | 2'-MOE | 2'-MOE | 2'-MOE | H | H |
| 2 | 9 | 2 | 9 | 2 | 2'-MOE | 2'-MOE | 2'-MOE | H | H |
| 2 | 10 | 2 | 8 | 2 | 2'-MOE | 2'-MOE | 2'-MOE | H | H |
| 2 | 11 | 2 | 7 | 2 | 2'-MOE | 2'-MOE | 2'-MOE | H | H |
| 2 | 12 | 2 | 6 | 2 | 2'-MOE | 2'-MOE | 2'-MOE | H | H |
| 2 | 13 | 2 | 5 | 2 | 2'-MOE | 2'-MOE | 2'-MOE | H | H |
| 2 | 14 | 2 | 4 | 2 | 2'-MOE | 2'-MOE | 2'-MOE | H | H |
| 2 | 15 | 2 | 3 | 2 | 2'-MOE | 2'-MOE | 2'-MOE | H | H |
| 2 | 16 | 2 | 2 | 2 | 2'-MOE | 2'-MOE | 2'-MOE | H | H |
| 2 | 2 | 3 | 15 | 2 | 2'-MOE | 2'-MOE | 2'-MOE | H | H |
| 2 | 3 | 3 | 14 | 2 | 2'-MOE | 2'-MOE | 2'-MOE | H | H |
| 2 | 4 | 3 | 13 | 2 | 2'-MOE | 2'-MOE | 2'-MOE | H | H |
| 2 | 5 | 3 | 12 | 2 | 2'-MOE | 2'-MOE | 2'-MOE | H | H |
| 2 | 6 | 3 | 11 | 2 | 2'-MOE | 2'-MOE | 2'-MOE | H | H |

TABLE 5-continued

| n₁ | n₂ | n₃ | n₄ | n₅ | Nu₁ | Nu₃ | Nu₅ | T₁ | T₂ |
|---|---|---|---|---|---|---|---|---|---|
| 2 | 7 | 3 | 10 | 2 | 2'-MOE | 2'-MOE | 2'-MOE | H | H |
| 2 | 8 | 3 | 9 | 2 | 2'-MOE | 2'-MOE | 2'-MOE | H | H |
| 2 | 9 | 3 | 8 | 2 | 2'-MOE | 2'-MOE | 2'-MOE | H | H |
| 2 | 10 | 3 | 7 | 2 | 2'-MOE | 2'-MOE | 2'-MOE | H | H |
| 2 | 11 | 3 | 6 | 2 | 2'-MOE | 2'-MOE | 2'-MOE | H | H |
| 2 | 12 | 3 | 5 | 2 | 2'-MOE | 2'-MOE | 2'-MOE | H | H |
| 2 | 13 | 3 | 4 | 2 | 2'-MOE | 2'-MOE | 2'-MOE | H | H |
| 2 | 14 | 3 | 3 | 2 | 2'-MOE | 2'-MOE | 2'-MOE | H | H |
| 2 | 15 | 3 | 2 | 2 | 2'-MOE | 2'-MOE | 2'-MOE | H | H |
| 2 | 8 | 6 | 6 | 2 | 2'-MOE | 2'-MOE | 2'-MOE | H | H |

In certain embodiments, a modified oligonucleotide complementary to a miRNA and consisting of 25 linked nucleosides has a Formula II selected from Table 6, where each internucleoside linkage is a phosphorothioate internucleoside linkage. In certain embodiments, a modified oligonucleotide having a Formula II selected from Table 6 has the nucleobase sequence recited in SEQ ID NOs 30.

TABLE 6

| n₁ | n₂ | n₃ | n₄ | n₅ | Nu₁ | Nu₃ | Nu₅ | T₁ | T₂ |
|---|---|---|---|---|---|---|---|---|---|
| 2 | 21 | 0 | 0 | 2 | 2'-MOE | 2'-MOE | 2'-MOE | H | H |
| 2 | 2 | 2 | 17 | 2 | 2'-MOE | 2'-MOE | 2'-MOE | H | H |
| 2 | 3 | 2 | 16 | 2 | 2'-MOE | 2'-MOE | 2'-MOE | H | H |
| 2 | 4 | 2 | 15 | 2 | 2'-MOE | 2'-MOE | 2'-MOE | H | H |
| 2 | 5 | 2 | 14 | 2 | 2'-MOE | 2'-MOE | 2'-MOE | H | H |
| 2 | 6 | 2 | 13 | 2 | 2'-MOE | 2'-MOE | 2'-MOE | H | H |
| 2 | 7 | 2 | 12 | 2 | 2'-MOE | 2'-MOE | 2'-MOE | H | H |
| 2 | 8 | 2 | 11 | 2 | 2'-MOE | 2'-MOE | 2'-MOE | H | H |
| 2 | 9 | 2 | 10 | 2 | 2'-MOE | 2'-MOE | 2'-MOE | H | H |
| 2 | 10 | 2 | 9 | 2 | 2'-MOE | 2'-MOE | 2'-MOE | H | H |
| 2 | 11 | 2 | 8 | 2 | 2'-MOE | 2'-MOE | 2'-MOE | H | H |
| 2 | 12 | 2 | 7 | 2 | 2'-MOE | 2'-MOE | 2'-MOE | H | H |
| 2 | 13 | 2 | 6 | 2 | 2'-MOE | 2'-MOE | 2'-MOE | H | H |
| 2 | 14 | 2 | 5 | 2 | 2'-MOE | 2'-MOE | 2'-MOE | H | H |
| 2 | 15 | 2 | 4 | 2 | 2'-MOE | 2'-MOE | 2'-MOE | H | H |
| 2 | 16 | 2 | 3 | 2 | 2'-MOE | 2'-MOE | 2'-MOE | H | H |
| 2 | 17 | 2 | 2 | 2 | 2'-MOE | 2'-MOE | 2'-MOE | H | H |
| 2 | 2 | 3 | 16 | 2 | 2'-MOE | 2'-MOE | 2'-MOE | H | H |
| 2 | 3 | 3 | 15 | 2 | 2'-MOE | 2'-MOE | 2'-MOE | H | H |
| 2 | 4 | 3 | 14 | 2 | 2'-MOE | 2'-MOE | 2'-MOE | H | H |
| 2 | 5 | 3 | 13 | 2 | 2'-MOE | 2'-MOE | 2'-MOE | H | H |
| 2 | 6 | 3 | 12 | 2 | 2'-MOE | 2'-MOE | 2'-MOE | H | H |
| 2 | 7 | 3 | 11 | 2 | 2'-MOE | 2'-MOE | 2'-MOE | H | H |
| 2 | 8 | 3 | 10 | 2 | 2'-MOE | 2'-MOE | 2'-MOE | H | H |
| 2 | 9 | 3 | 9 | 2 | 2'-MOE | 2'-MOE | 2'-MOE | H | H |
| 2 | 10 | 3 | 8 | 2 | 2'-MOE | 2'-MOE | 2'-MOE | H | H |
| 2 | 11 | 3 | 7 | 2 | 2'-MOE | 2'-MOE | 2'-MOE | H | H |
| 2 | 12 | 3 | 6 | 2 | 2'-MOE | 2'-MOE | 2'-MOE | H | H |
| 2 | 13 | 3 | 5 | 2 | 2'-MOE | 2'-MOE | 2'-MOE | H | H |
| 2 | 14 | 3 | 4 | 2 | 2'-MOE | 2'-MOE | 2'-MOE | H | H |
| 2 | 15 | 3 | 3 | 2 | 2'-MOE | 2'-MOE | 2'-MOE | H | H |
| 2 | 16 | 3 | 2 | 2 | 2'-MOE | 2'-MOE | 2'-MOE | H | H |
| 2 | 8 | 6 | 7 | 2 | 2'-MOE | 2'-MOE | 2'-MOE | H | H |

A modified oligonucleotide having a gapmer motif may have an internal region consisting of linked 2'-deoxynucleotides, and external regions consisting of linked 2'-modified nucleosides. Such a gapmer may be designed to elicit RNase H cleavage of a miRNA precursor. The internal 2'-deoxynucleoside region serves as a substrate for RNase H, allowing the cleavage of the miRNA precursor to which a modified oligonucleotide is targeted. In certain embodiments, each nucleoside of each external region comprises the same 2'-modified nucleoside. In certain embodiments, one external region is uniformly comprised of a first 2'-modified nucleoside and the other external region is uniformly comprised of a second 2'-modified nucleoside.

A modified oligonucleotide having a gapmer motif may have a sugar modification at each nucleoside. In certain embodiments, the internal region is uniformly comprised of a first 2'-modified nucleoside and each of the wings is uniformly comprised of a second 2'-modified nucleoside. In certain such embodiments, the internal region is uniformly comprised of 2'-fluoro nucleosides and each external region is uniformly comprised of 2'-O-methoxyethyl nucleosides.

In certain embodiments, each external region of a gapmer consists of linked 2'-O-methoxyethyl nucleosides. In certain embodiments, each external region of a gapmer consists of linked 2'-O-methyl nucleosides. In certain embodiments, each external region of a gapmer consists of 2'-fluoro nucleosides. In certain embodiments, each external region of a gapmer consists of linked bicyclic nucleosides.

In certain embodiments, each nucleoside of one external region of a gapmer comprises 2'-O-methoxyethyl nucleosides and each nucleoside of the other external region comprises a different 2'-modification. In certain such embodiments, each nucleoside of one external region of a gapmer comprises 2'-O-methoxyethyl nucleosides and each nucleoside of the other external region comprises 2'-O-methyl nucleosides. In certain such embodiments, each nucleoside of one external region of a gapmer comprises 2'-O-methoxyethyl nucleosides and each nucleoside of the other external region comprises 2'-fluoro nucleosides. In certain such embodiments, each nucleoside of one external region of a gapmer comprises 2'-O-methyl nucleosides and each nucleoside of the other external region comprises 2'-fluoro nucleosides. In certain such embodiments, each nucleoside of one external region of a gapmer comprises 2'-O-methoxyethyl nucleosides and each nucleoside of the other external region comprises bicyclic nucleosides. In certain such embodiments, each nucleoside of one external region of a gapmer comprises 2'-O-methyl nucleosides and each nucleoside of the other external region comprises bicyclic nucleosides.

In certain embodiments, nucleosides of one external region comprise two or more sugar modifications. In certain embodiments, nucleosides of each external region comprise two or more sugar modifications. In certain embodiments, at least one nucleoside of an external region comprises a 2'-O-methoxyethyl sugar and at least one nucleoside of the same external region comprises a 2'-fluoro sugar. In certain embodiments, at least one nucleoside of an external region comprises a 2'-O-methoxyethyl sugar and at least one nucleoside of the same external region comprises a bicyclic sugar moiety. In certain embodiments, at least one nucleoside of an external region comprises a 2'-O-methyl sugar and at least one nucleoside of the same external region comprises a bicyclic sugar moiety. In certain embodiments at least one nucleoside of an external region comprises a 2'-O-methyl sugar and at least one nucleoside of the same external region comprises a 2'-fluoro sugar. In certain embodiments, at least one nucleoside of an external region comprises a 2'-fluoro sugar and at least one nucleoside of the same external region comprises a bicyclic sugar moiety.

In certain embodiments, each external region of a gapmer consists of the same number of linked nucleosides. In certain embodiments, one external region of a gapmer consists a number of linked nucleosides different that that of the other external region.

In certain embodiments, the external regions comprise, independently, from 1 to 6 nucleosides. In certain embodiments, an external region comprises 1 nucleoside. In certain embodiments, an external region comprises 2 nucleosides. In certain embodiments, an external region comprises 3 nucleosides. In certain embodiments, an external region comprises 4 nucleosides. In certain embodiments, an external region comprises 5 nucleosides. In certain embodiments, an external region comprises 6 nucleosides. In certain embodiments, the internal region consists of 17 to 28 linked nucleosides. In certain embodiments, an internal region consists of 17 to 21 linked nucleosides. In certain embodiments, an internal region consists of 17 linked nucleosides. In certain embodiments, an internal region consists of 18 linked nucleosides. In certain embodiments, an internal region consists of 19 linked nucleosides. In certain embodiments, an internal region consists of 20 linked nucleosides. In certain embodiments, an internal region consists of 21 linked nucleosides. In certain embodiments, an internal region consists of 22 linked nucleosides. In certain embodiments, an internal region consists of 23 linked nucleosides. In certain embodiments, an internal region consists of 24 linked nucleosides. In certain embodiments, an internal region consists of 25 linked nucleosides. In certain embodiments, an internal region consists of 26 linked nucleosides. In certain embodiments, an internal region consists of 27 linked nucleosides. In certain embodiments, an internal region consists of 28 linked nucleosides.

Certain Additional Therapies

Cancer treatments often comprise more than one therapy. As such, in certain embodiments the present invention provides methods for treating liver cancer comprising administering to a subject in need thereof a compound comprising a modified oligonucleotide complementary to a miRNA, or a precursor thereof, and further comprising administering at least one additional therapy.

In certain embodiments, an additional therapy may also be designed to treat liver cancer, such as HCC. An additional therapy may be a chemotherapeutic agent. Suitable chemotherapeutic agents include 5-fluorouracil, gemcitabine, doxorubicine, mitomycin c, sorafenib, etoposide, carboplatin, epirubicin, irinotecan and oxaliplatin. An additional suitable chemotherapeutic agent includes a modified oligonucleotide, other than a modified oligonucleotide of the present invention, that is used to treat cancer. An additional therapy may be surgical resection of a liver tumor(s), liver transplantation, or chemoembolization.

In certain embodiments, an additional therapy may be designed to treat a disease other than liver cancer, including HCC. In certain such embodiments, an additional therapy may be a treatment for hepatitis C infection or hepatitis B infection.

In certain embodiments, an additional therapy is a treatment for hepatitis C infection. Therapeutic agents for treatment of hepatitis C infection include interferons, for example, interferon alfa-2b, interferon alfa-2a, and interferon alfacon-1. Less frequent interferon dosing can be achieved using pegylated interferon (interferon attached to a polyethylene glycol moiety which significantly improves its pharmacokinetic profile). Combination therapy with interferon alfa-2b (pegylated and unpegylated) and ribavarin has also been shown to be efficacious for some patient populations. Other agents currently being developed include RNA replication inhibitors (e.g., ViroPharma's VP50406 series), antisense agents (for example, anti-miR-122), therapeutic vaccines, protease inhibitors, helicase inhibitors and antibody therapy (monoclonal and polyclonal).

In certain embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and *echinacea*), and vaccines, e.g., the immunostimulating complex (ISCOM), which comprises a vaccine formulation that combines a multimeric presentation of antigen and an adjuvant.

In certain such embodiments, the additional therapy is selected to treat or ameliorate a side effect of one or more pharmaceutical compositions of the present invention. Such side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

Certain Pharmaceutical Compositions

In certain embodiments, a compound comprising a modified oligonucleotide complementary to a miRNA, or precursor thereof, described herein is prepared as a pharmaceutical composition for the treatment of liver cancer, including HCC. Suitable administration routes include, but are not limited to, oral, rectal, transmucosal, intestinal, enteral, topical, suppository, through inhalation, intrathecal, intraventricular, intraperitoneal, intranasal, intraocular, intratumoral, and parenteral (e.g., intravenous, intramuscular, intramedullary, and subcutaneous). An additional suitable administration route includes chemoembolization. In certain embodiments, pharmaceutical intrathecals are administered to achieve local rather than systemic exposures. For example, pharmaceutical compositions may be injected directly in the area of desired effect (e.g., into a tumor).

In certain embodiments, a pharmaceutical composition of the present invention is administered in the form of a dosage unit (e.g., tablet, capsule, bolus, etc.). In certain embodiments, such pharmaceutical compositions comprise a modified oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of a modified oligonucleotide which has been prepared in water for injection, or in saline for injection, adjusted to pH 7.0-9.0 with acid or base during preparation, and then lyophilized. The lyophilized modified oligonucleotide may be 25-800 mg of a modified oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide. The lyophilized drug product may be packaged in a 2 mL Type I, clear glass vial (ammonium sulfate-treated), stoppered with a bromobutyl rubber closure and sealed with an aluminum FLIP-OFF® overseal.

In certain embodiments, the compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

In certain embodiments, pharmaceutical compositions of the present invention comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more compounds comprising a modified oligonucleotide with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition of the present invention comprises a modified oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides of the present invention is formulated as a prodrug. In certain embodiments, upon in vivo administration, a prodrug is chemically converted to the biologically, pharmaceutically or therapeutically more active form of a modified oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Certain Experimental Models

In certain embodiments, the present invention provides methods of using and/or testing modified oligonucleotides of the present invention in an experimental model. In certain embodiments, experimental models are employed to evaluate the effectiveness of modified oligonucleotides of the invention for the treatment of liver cancer, including HCC. Those having skill in the art are able to select and modify the protocols for such experimental models to evaluate a pharmaceutical agent of the invention.

Generally, modified oligonucleotides are first tested in cultured cells. Suitable cell types include those that are related to the cell type to which delivery of a modified oligonucleotide is desired in vivo. For example, suitable cell types for the study of modified oligonucleotides for the treatment of liver cancer include cell types derived from liver cancer, such as HepG2, Hep3B, SK-Hep1, 7721, SNU-398, SNU423, SNU449, Huh7, HCCLM3 and MHT cells.

In certain embodiments, the extent to which a modified oligonucleotide interferes with the activity of a miRNA is assessed in cultured cells. In certain embodiments, inhibition of miRNA activity may be assessed by measuring the levels of the miRNA. Alternatively, the level of a predicted or validated miRNA target may be measured. An inhibition of miRNA activity may result in the increase in the mRNA and/or protein of a miRNA target. Further, in certain embodiments, certain phenotypic outcomes may be measured. For example, suitable phenotypic outcomes include inhibition of cell proliferation, the induction of cell death, and/or the induction of apoptosis. Other suitable phenotypic outcomes include the arrest of cells at any point of the cell cycle, such as the G1/S transition, S phase, the G2/M transition, mitotic division, or cytokinesis.

Following the in vitro identification of a modified oligonucleotide that effectively inhibits the activity of a miRNA, modified oligonucleotides are further tested in in vivo experimental models. Suitable experimental models for the testing of chemotherapeutic agents, including modified oligonucleotides complementary to a miRNA described herein, include: a subcutaneous xenograft mouse model, an orthotopic liver xenograft mouse model, an SV40 t/T transgenic mouse model, a TGF-α/c-myc transgenic mouse model and a chemically induced carcinogenic (diethylnitrosamine) mouse model.

A suitable in vivo experimental model for the testing of modified oligonucleotides of the present invention includes the subcutaneous xenograft mouse model. In this model, cells are removed from culture and injected subcutaneously into mice. Suitable cells include, for example, Hep3B cells. Suitable mice include, for example, BALB/c nude mice. A suitable injection site is, for example, the flank of the mouse. Modified oligonucleotide, dissolved in saline, is administered to the mice at a frequency of 2 to 3 times per week. Modified oligonucleotide is administered prior to implantation, simultaneously with implantation, or after implantation. Suitable administration route include intraperitoneal administration and intratumoral administration. Modified oligonucleotide doses range from 5 to 50 mg/kg. The animals are treated for 3 to 4 weeks, after which tumor size, tumor number, and liver weight are measured. Measurements may be made with digital calipers. Saline-treated animals are used as a control group. A chemotherapeutic agent, such as, for example, 5-flurouracil, may be used as a positive control for the inhibition of tumor size or number. Various endpoints are assessed, including tumor size, tumor number, and liver weight. Modified oligonucleotide-treated mice are compared to the same endpoints in control-treated mice. Statistical analyses are employed to identify significant differences in any of the endpoints. The subcutaneous xenograft model is an art-accepted model for the in vivo evaluation of chemotherapeutic agents, including modified oligonucleotides. See, for example, Koller et al., *Cancer Res.*, 2006, 66, 2059-2066, and Cheng et al., *Cancer Res.*, 2007, 67, 309-317.

A suitable in vivo experimental model for the testing of modified oligonucleotides of the present invention is the HCCLM3 orthotopic liver xenograft model. In this model, approximately 1 million HCCLM3 cells (a highly metastatic human HCC cell line) are subcutaneously injected into the flanks of BALB/c nude mice. Once tumors are an appropriate size (e.g. 1 mm$^3$), tumor fragments are removed and intrahepatically implanted into other BALB/c nude mice. At this point, modified oligonucleotide, dissolved in saline, is administered to the mice at a frequency of 2 to 3 times per week. Alternatively, administration of modified oligonucleotide begins several days (e.g. 10 days) following implantation. Suitable administration route include intraperitoneal administration and intratumoral administration. Modified oligonucleotide doses range from 5 to 50 mg/kg. The animals are treated for 3 to 4 weeks for a short term study, after which tumor size, tumor number, and liver weight are measured. Alternatively, the animals are treated for 8 to 30 weeks for a long term study, after which various endpoints are assessed, including tumor size, tumor number, liver weight, number of metastases and survival will be measured. Metastasis is measured in tissues such as lung tissue. Measurements of tumor size and weight may be made with digital calipers. Saline-treated animals are used as a control group. A chemotherapeutic agent, such as, for example, 5-flurouracil, may be used as a positive control for the inhibition of tumor size or number. Endpoints observed in modified oligonucleotide-treated mice are compared to the same endpoints in control-treated mice. Statistical analyses are employed to identify significant differences in any of the endpoints. The orthotopic xenograft model is an art-accepted model for the in vivo evaluation of chemotherapeutic agents, including modified oligonucleotides. See, for example, Li et al., *Clin. Cancer Res.,* 2006, 12, 7140-7148. As an alternative to HCCLM3 cells, HepG2 cells may be used to establish the orthotopic model.

An additional suitable in vivo experimental model is the SV40 t/T transgenic mouse model. Transgenic mice have been engineered to express the SV40 large T antigen (SV40 t/T mice) under the control of the liver-specific C-reactive protein promoter (Ruther et al., Oncogene, 1993, 8, 87-93). The expression of SV40 large T antigen can be transiently induced by injection of bacterial lipopolysaccacharide, and results in the development of hepatocellular carcinoma. At this point, modified oligonucleotide, dissolved in saline, is administered to the mice at a frequency of 2 to 3 times per week. Modified oligonucleotide doses range from 5 to 50 mg/kg. Suitable administration route include intraperitoneal administration and intratumoral administration. The animals are treated for 3 to 4 weeks for a short term study, after which tumor size, tumor number, and liver weight are measured. Alternatively, the animals are treated for 8 to 30 weeks for a long term study, after which various endpoints are measured, including tumor size, tumor number, liver weight, number of metastases, and survival. Metastasis is measured in tissues such as lung tissue. Measurements of tumor size and weight may be made with digital calipers. Saline-treated animals are used as a control group. A chemotherapeutic agent, such as, for example, 5-flurouracil, may be used as a positive control for the inhibition of tumor size or number. Endpoints observed in modified oligonucleotide-treated mice are compared to the same endpoints in control-treated mice. Statistical analyses are employed to identify significant differences in any of the endpoints.

A suitable in vivo experimental model is a chemically-induced carcinogenic mouse model. In this model, liver cancer is induced by administration of the carcinogen diethylnitrosamine (DEN). Mice are injected intraperitoneally with 5 or 25 mg/kg DEN. Modified oligonucleotide, dissolved in saline, is administered to the mice at a frequency of 2 to 3 times per week. Modified oligonucleotide doses range from 5 to 50 mg/kg. Suitable administration route include intraperitoneal administration and intratumoral administration. The animals are treated for 4 to 8 weeks for a short term study, after which tumor size, tumor number, and liver weight are measured. Alternatively, the animals are treated for 8 to 30 weeks for a long term study, after which tumor size, tumor number, liver weight, number of metastases and survival will be measured. Metastasis is measured in tissues such as lung tissue. Measurements of tumor size and weight may be made with digital calipers. Saline-treated animals are used as a control group. A chemotherapeutic agent, such as, for example, 5-flurouracil, may be used as a positive control for the inhibition of tumor size or number. Endpoints observed in modified oligonucleotide-treated mice are compared to the same endpoints in control-treated mice. Statistical analyses are employed to identify significant differences in any of the endpoints. The DEN-induced HCC model has been used for the study of HCC. See, for example, Maeda et al., *Cell,* 2005, 121, 977-990.

Dioxins

Dioxins are a family of environmental pollutants such as 2,3,7,8-tetrachlorodibenzo-p-dioxin (TCDD), that are known to have multiple hazardous effects. TCDD is known to be a most potent carcinogen, and also to induce other adverse biological responses. Dioxin induced effects include, but are not limited to, skin diseases, birth defects, miscarriages, developmental defects, teratogenesis, immunotoxicity and cancer. Dioxins are produced in small concentrations when organic material is burned in the presence of chlorine. This procedure occurs often in a variety of industrial processes such as in the bleaching of paper, but dioxins can also be produced from natural sources such as volcanoes and forest fires. Dioxins enter the general population primarily from ingestion of food (herbicides), due to their lipophilic properties, but also by inhalation. The general treatment after dioxin exposure is dietary fat to remove it from the body since it is very lypophilic. Additional approaches for lowering dioxin include dietary intake of mineral oil (Moser and McLachlan, 1999), activated charcoal (Araki, 1974), rice bran oil (Ilda, 1995), or the fat substitute Olestra (Geusau et al., 1999, 2002), however the effectiveness of these treatments is minimal.

The mechanism of dioxins' carcinogenic effect is not yet fully understood, however it is known to be an Aryl hydrocarbon receptor (AhR) ligand, and most, if not all of its effects, are thought to be mediated through the activation of AhR.

AhR belongs to a family of ligand activated transcription factors basic helix-loop-helix/Per-Arnt-Sim (bHLH/PAS) that mediates transcriptional activation of sets of enzymes that function in the metabolism of xenobiotics. Upon ligand binding the AhR translocates to the nucleus and associates with its partner protein Arnt to form a heterodimer. The heterodimer binds to an enhancer site on the DNA designated xenobiotic responsive element (XRE) and is responsible to regulate a variety of transcription activation of enzymes involved in xenobiotic metabolism and other functions. One of the genes that are transcriptionally regulated by AhR is an AhR repressor (AhRR) that can also form a heterodimer with Arnt and bind to XRE, however this forms transcriptional repression. Since AhRR transcription is regulated by AhR, AhR and AhRR form a regulatory feedback loop.

As a result of AhR activation an "AhR gene battery" of Phase I and Phase II metabolizing enzymes consisting of CYP1A1, CYP1A2, CYP1B1, NQO1, ALHD3A1, UGT1A2 and GSTA1 is up-regulated. This response presumably evolved to be able to detect a wide range of chemicals, indicated by the wide range of substrates AhR is able to bind and facilitate their biotransformation and elimination as detoxification process.

However, AhR activation also elicits toxic responses. Toxicity results from two different pathways of AhR signaling. The first is when the induction of metabolizing enzymes results in the production of toxic intermediate metabolites. The second path to toxicity is the result of aberrant changes in global gene transcription beyond those observed in the "AhR gene battery." These global changes in gene expression lead to adverse changes in cellular processes and function.

Many studies conducted in order to elucidate the mechanism and understand the toxicity and carcinogenicity of TCDD via AhR activation resulted with paradoxical outcomes. Repeatedly inconsistent results are reported, showing both apoptotic and anti-apoptotic effects of TCDD activated AhR cellular responses, usually explained by differences in the treatment regiment and models tested.

Although the induction of the AhR by dioxins is well characterized, the function and mechanism of some of its toxicities are still unknown and the paradoxical and contradicting results appearing in many articles indicate the necessity for further study of TCDD mechanism of carcinogenicity.

To date there has been no definitive description of any miR whose expression is directly regulated by dioxins, or of the functional consequences of such regulation; Moffat et al. (Toxicol Sci. 2007 October; 99(2):470-87) showed only very moderate changes in miRs in response to TCDD in rodent models and concluded that microRNAs do not play a role in dioxin toxicity.

As demonstrated herein, hsa-miR-191, which is up-regulated in HCC, is also up-regulated after TCDD activation of the AhR transcription factor, together with miR-181a, and hsa-miR-181b, and to a lesser degree hsa-miR-181a*. Thus, the AhR transcription factor is responsible for the regulation of the expression of miRs having an AhR TFBS motif at their promoters. The involvement of miRs in the mechanism of TCDD activity can explain the down regulation of several genes as seen on expression arrays, apart from transcriptional activation through AhR.

Certain Quantitation Assays

The effects of antisense inhibition of a miRNA following the administration of modified oligonucleotides may be assessed by a variety of methods known in the art. In certain embodiments, these methods are be used to quantitate miRNA levels in cells or tissues in vitro or in vivo. In certain embodiments, changes in miRNA levels are measured by microarray analysis. In certain embodiments, changes in miRNA levels are measured by one of several commercially available PCR assays, such as the TaqMan® MicroRNA Assay (Applied Biosystems). In certain embodiments, antisense inhibition of a miRNA is assessed by measuring the mRNA and/or protein level of a target of a miRNA. Antisense inhibition of a miRNA generally results in the increase in the level of mRNA and/or protein of a target of the miRNA.

The following examples are presented in order to more fully illustrate some embodiments of the invention. They should, in no way be construed, however, as limiting the broad scope of the invention.

EXAMPLES

Example 1: Expression Profiling of miRNAs in Tissue Samples

To identify miRNAs that are dysregulated in association with cancer, miRNA expression profiles were analyzed in liver samples from subjects with hepatocellular carcinoma (HCC), and were compared to expression profiles in normal liver. Samples analyzed included: 37 liver samples from human HCC subjects; 39 liver samples of normal liver adjacent to HCC; and 2 liver samples from normal human liver. Of the 39 samples of normal liver adjacent to HCC, 36 were from the human HCC subjects.

Liver samples were also collected from transgenic mice which express the SV40 t/T antigen under the control of the C-reactive protein promoter. This promoter results in hepatocyte-specific expression of the oncogenic SV40 t/T antigen, which eventually leads to the development of liver tumors that are histologically characterized as hepatocellular carcinoma. Samples analyzed included: 12 samples from normal mouse liver; 18 HCC samples from SV40 transgenic mice.

Also analyzed were HCC-related cell lines, including HepG2, Hep3B, SK-Hep1, 7721, SNU-398, SNU423, SNU449, Huh7 and MHT. MHT cells are isolated from the livers of SV40 t/T antigen transgenic mice. Monkey hepatocytes were also analyzed.

RNA was extracted from the samples using the miRvana miRNA isolation kit (Ambion) according to the manufacturer's instructions and hybridized to a microRNA array. Custom microarrays were produced by printing DNA oligonucleotide probes representing about 700 miRNAs, including miRNAs from the Sanger database, version 9 and additional Rosetta genomics validated and predicted miRs. Each probe, printed in triplicate, carries up to 22-nt linker at the 3' end of the miRNA's complement sequence in addition to an amine group used to couple the probes to coated glass slides. 20 µM of each probe were dissolved in 2×SSC+ 0.0035% SDS and spotted in triplicate on Schott Nexterion® Slide E coated microarray slides using a Genomic Solutions® BioRobotics MicroGrid II according the MicroGrid manufacturer's directions. 64 negative control probes were designed using the sense sequences of different miRNAs. Two groups of positive control probes were designed to hybridize to miRdicator™ array (1) synthetic spikes small RNA were added to the RNA before labeling to verify the labeling efficiency and (2) probes for abundant small RNA (e.g. small nuclear RNAs (U43, U49, U24, Z30, U6, U48, U44), 5.8s and 5s ribosomal RNA) are spotted on the array to verify RNA quality. The slides were blocked in a solution containing 50 mM ethanolamine, 1M Tris (pH 9.0) and 0.1% SDS for 20 min at 50° C., then thoroughly rinsed with water and spun dry.

Five µg of total RNA was labeled by ligation of a RNA-linker p-rCrU-Cy-dye (Thomson et al., 2004, Nat Methods 1, 47-53) (Dharmacon) to the 3'-end with Cy3 or Cy5. The labeling reaction contained total RNA, spikes (0.1-20 fmoles), 300 ng RNA-linker-dye, 15% DMSO, 1x ligase buffer and 20 units of T4 RNA ligase (NEB) and proceeded at 4° C. for 1 hr followed by 1 hr at 37° C. The labeled RNA was mixed with 3× hybridization buffer (Ambion), heated to 95° C. for 3 min and than added on top of the miRdicator™ array. Slides were hybridize 12-16 hr, followed by two washes with 1×SSC and 0.2% SDS and a final wash with 0.1×SSC.

Arrays were scanned using an Agilent Microarray Scanner Bundle G2565BA (resolution of 10 µm at 100% power). Array images were analyzed using SpotReader software (Niles Scientific).

Raw data of miRNA signals were normalized and a T-test was used to identify statistically significant differentially expressed miRNAs.

Figure 1:
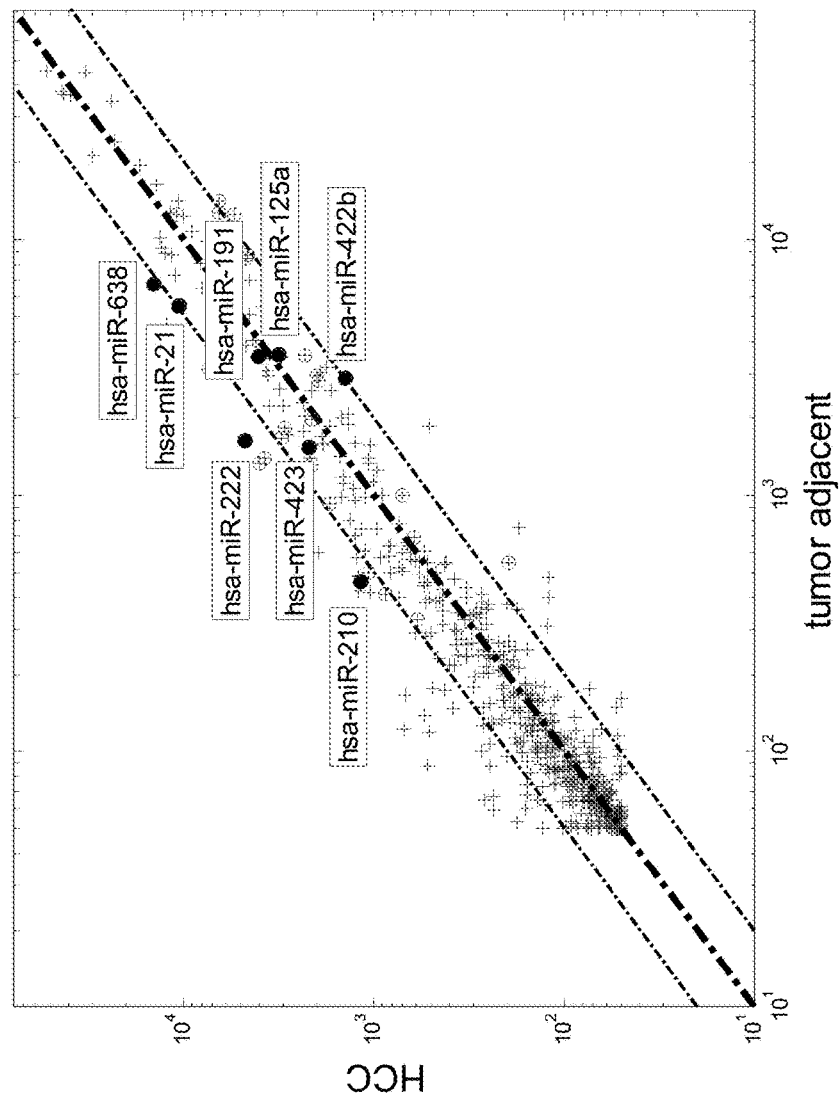
FIG. 1. Differential expression analysis of miRNAs in liver tumor samples compared to normal liver tissue samples. Data points having significant p-values are enclosed by red circles. Certain miRNA targets that were later selected for further study are represented by filled yellow circles. These miRNA targets include miR-21, miR-125a-5p (labeled as miR-125a), miR-191, miR-210, miR-222, miR-378 (labeled as miR-422b), miR-423-3p, and miR-638.

94 miRNAs were selected as candidate miRNAs for further study. These miRNAs were selected based on one or more of the following criteria: differential expression in human liver tumor samples relative to normal human liver samples; differential expression in mouse HCC samples relative to normal mouse liver samples; or high expression in human liver tissue. FIG. 1 illustrates 8 of the miRNAs that exhibited elevated expression in liver tumor samples.

Example 2: miRNA Expression Profiling of Cancer Cell Lines

The miRNA expression profiles of miRNAs in various cancer cell lines were compared to miRNA expression profiles of human liver cancer samples. It was observed that many of the miRNAs highly expressed in human liver cancer samples were also highly expressed in human cancer cell lines. These miRNAs included, for example, miR-21, and miR-191. Accordingly, the human liver cancer cell lines are useful for the identification and study of modified oligonucleotides that are candidates for the treatment of liver cancer.

Example 3: Anti-Proliferative Effects of Modified Oligonucleotides

To determine the involvement of the candidate miRNAs in cell proliferation, modified oligonucleotides were used to inhibit the activity of the candidate miRNAs.

The ability of the cells to proliferate was measured using the MTS Cell Proliferation Assay (CellTiter 96® AQueous One Solution Cell Proliferation Assay Promega Corporation Madison, Wis.). The MTS assay is a colorimetric assay that measures the reduction of a tetrazolium component (MTS reagent) into an insoluble formazan product by the mitochondria of viable cells. After incubation of the cells with the MTS reagent for approximately 2 to 4 hours, the samples are read using an ELISA plate reader at a wavelength of 490 nM. The amount of color produced is directly proportional to the number of cells.

Modified oligonucleotides complementary to the selected miRNAs were designed and synthesized. Each nucleoside of each modified oligonucleotide has a 2'-O-methoxyethyl sugar, each internucleoside linkage is a phosphorothioate internucleoside linkage, and all cytosines are 5-methylcytosines. Additional modified oligonucleotides tested included modified oligonucleotides having a 2'-O-methoxyethyl sugar at each nucleoside, and phosphodiester internucleoside linkages.

The modified oligonucleotides were tested for their antiproliferative effects in Hep3B cells and SNU423 cells. Cells were treated with 20, 40, 70, 150, or 300 nM of modified oligonucleotide, in triplicate samples, for a period of 4 hours, after which the media was replaced with normal growth media. Oligofectamine was used as the transfection reagent. Untreated cells served as controls, as well as transfection with a modified oligonucleotide with 6 mismatches to hsa-mir-122. As a control for inhibition of proliferation, cells were treated with a modified oligonucleotide known to inhibit cell proliferation. The proliferation assay was performed 48 to 72 hours following addition of the modified oligonucleotides.

Figure 2A:
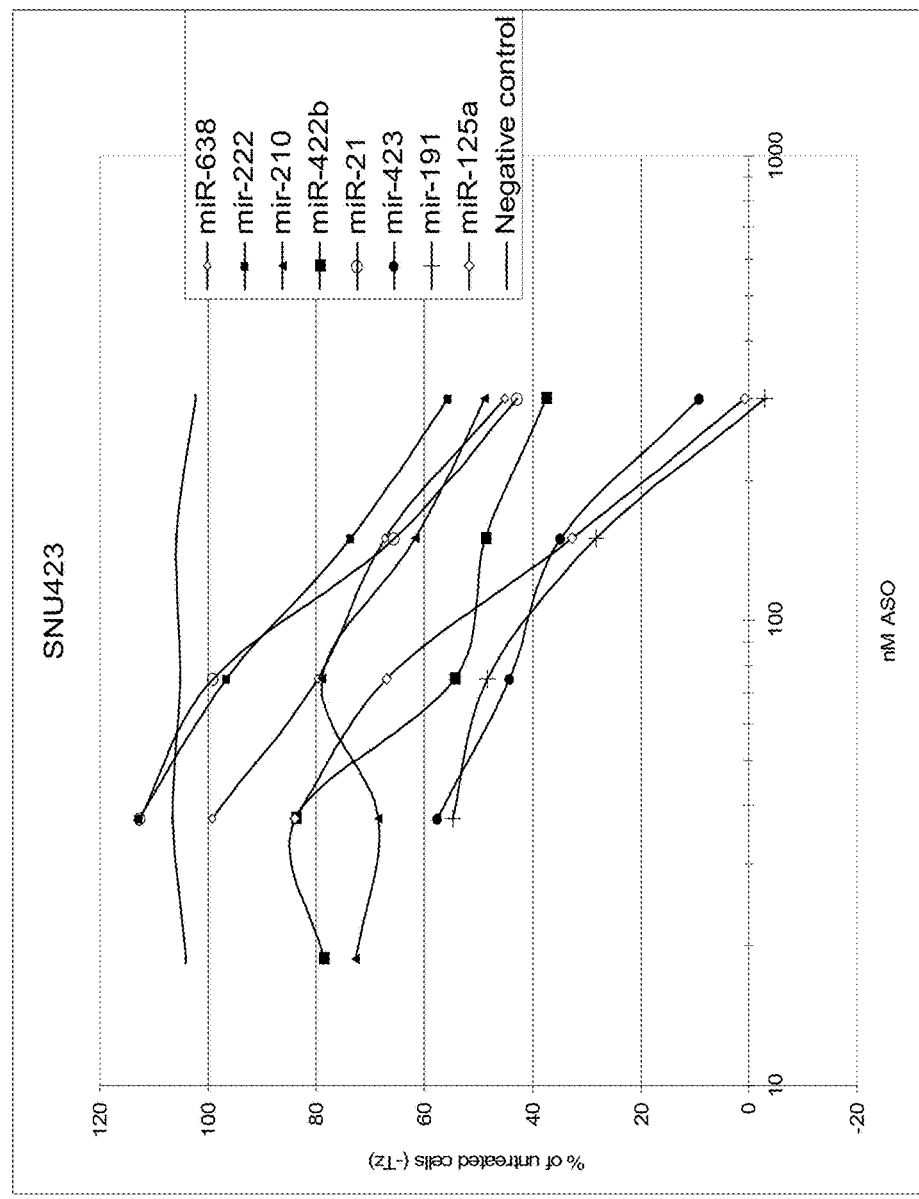
FIGS. 2A and 2B. Inhibition of cell proliferation in liver cancer cell lines following treatment with modified oligonucleotides targeted to miRNAs. Proliferation of both SNU423 (FIG. 2A) and Hep3B (FIG. 2B) cell lines was tested after transfection with modified oligonucleotides. A proliferation assay was performed 72 hours after transfection. Proliferation was measured and compared to proliferation of cells treated with a negative control oligonucleotide and to proliferation of untransfected cells. Modified oligonucleotides complementary to miR-21, miR-125a, miR-191, miR-210, miR-222, miR-378 (labeled as miR-422b), miR-423, and miR-638 resulted in antiproliferative activity.
Figure 2B:
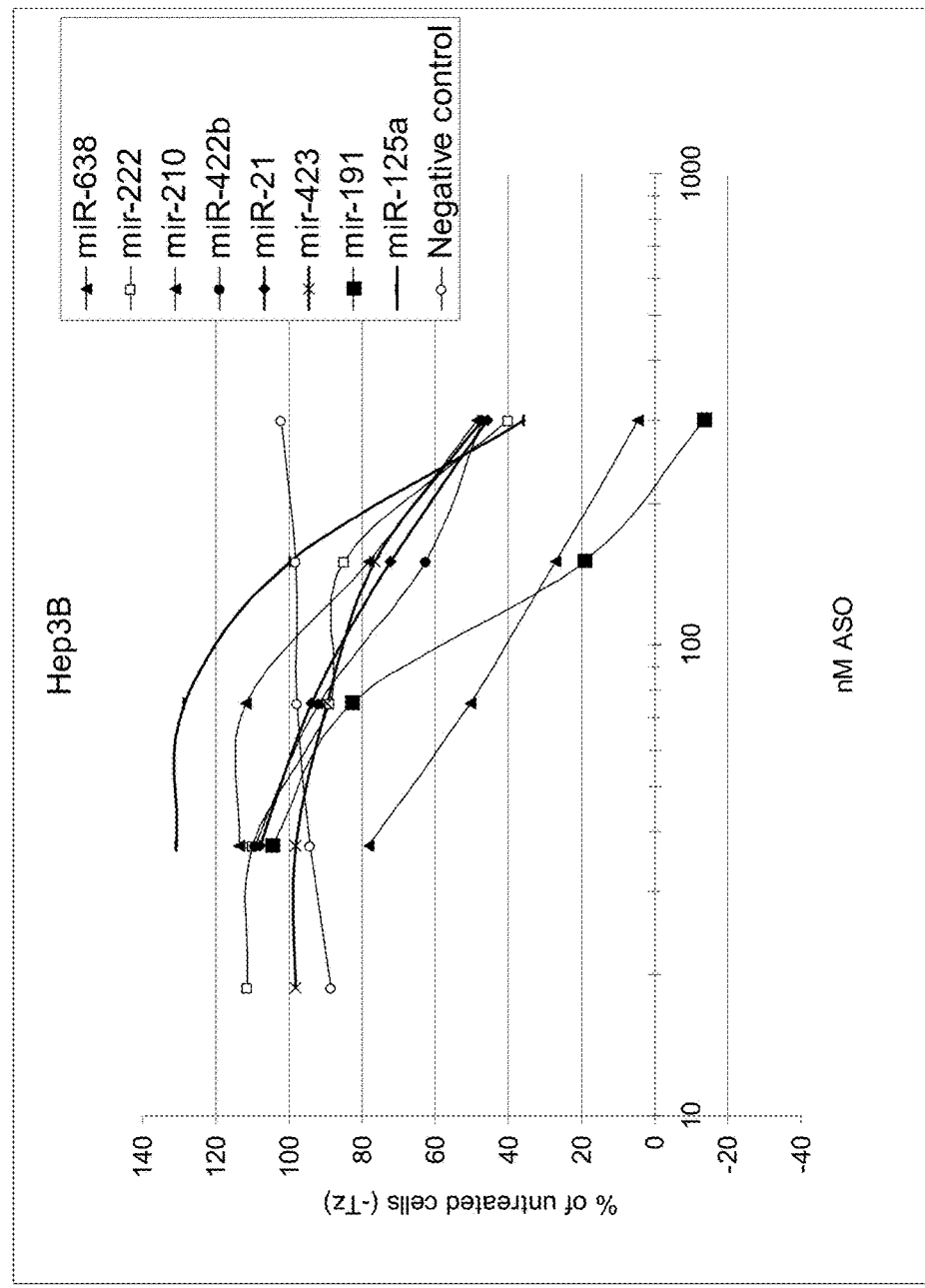

The number of cells in modified oligonucleotide-treated samples was compared to the number of cells in untreated control samples. In this way, the proliferation of cells was measured. The comparison revealed that antisense inhibition of miR-21, miR-125a-5p, miR-191, miR-210, miR-222, miR-378, miR-423-3p, and miR-638 resulted in inhibition of cell proliferation (FIG. 2). Thus, modified oligonucleotides complementary to a miR selected from miR-21, miR-125a-5p, miR-191, miR-210, miR-222, miR-378, miR-423-3p, and miR-638 exhibited anti-proliferative effects in HCC cell lines. As shown in FIG. 1, the expression of each of these 8 miRNAs is elevated in liver tumor samples, relative to normal liver tissue samples. Accordingly, such modified oligonucleotides are therapeutic agents for the treatment of HCC. Examples of such modified oligonucleotides are illustrated in Table 1.

Example 4: Apoptotic Activity of Modified Oligonucleotides

To determine the involvement of the candidate miRNAs in cell survival, modified oligonucleotides were used to inhibit the activity of the miRNAs, and caspase activity was used as an indicator of apoptosis.

Apoptosis was evaluated by measuring the activity of caspase 3 and caspase 7. A fluorogenic substrate was added to the wells of cells. When this substrate is cleaved by activated caspases 3 and 7, a fluorescent signal is generated. This signal can be quantitated in a fluorescence plate reader and used to determine the extent of capsase activation.

The modified oligonucleotides shown in Table 1 were tested for their effects on caspase 3 and caspase 7 activity in Hep3B cells. Cells were treated with 50, 100, 150, or 200 nM of modified oligonucleotide, in triplicate samples, for a period of 24 hours. Oligofectamine was used as the transfection reagent. Untreated cells served as controls as well as transfection with a modified oligonucleotide having 6 mismatches to has-miR-122.

Figure 3:
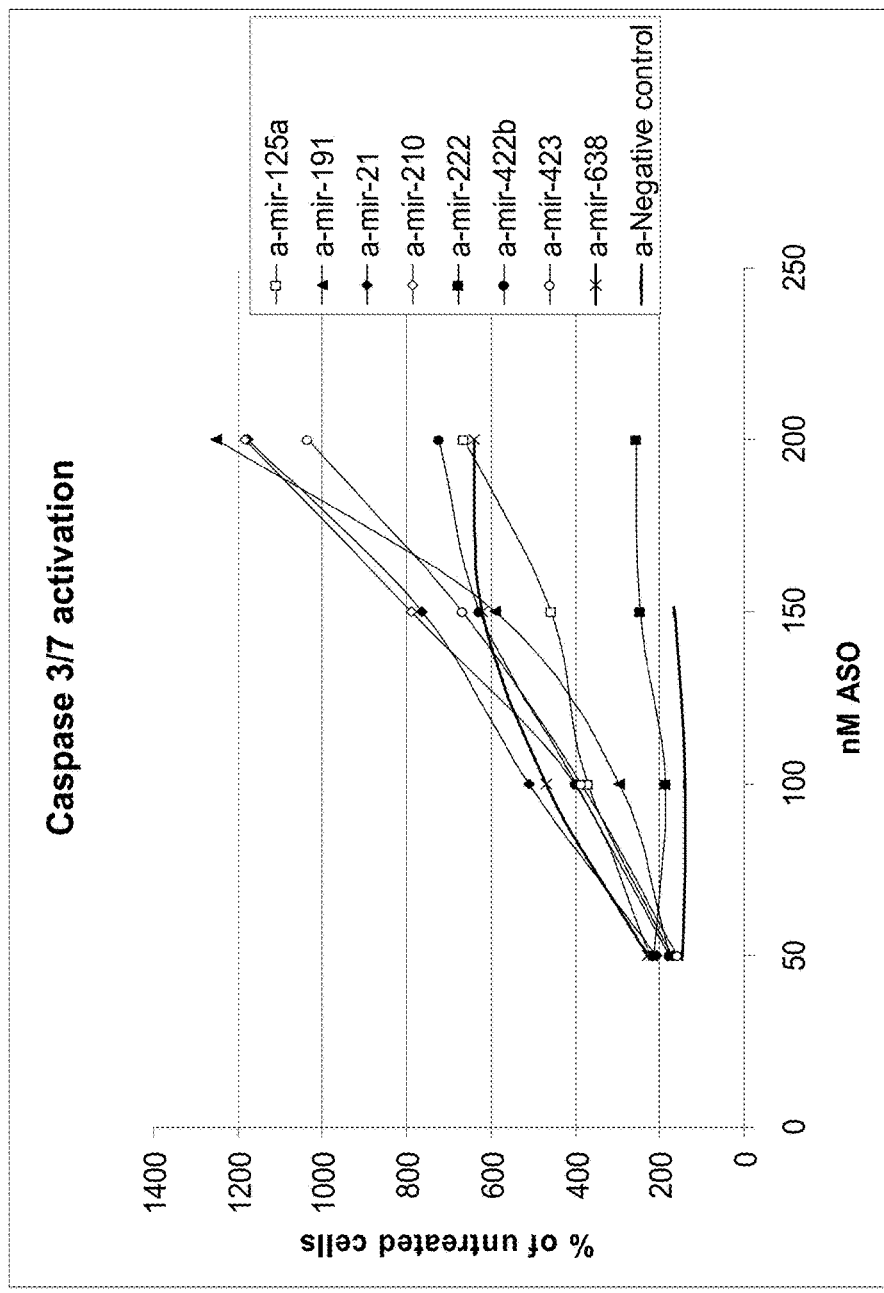
FIG. 3. Induction of apoptosis in liver cancer cells following treatment with modified oligonucleotides targeted to miRNAs. Hep3B cells were transfected with modified oligonucleotides. The induction of apoptosis was measured 24 hours after transfection, by testing Caspase 3/7 activation. Treatment of cells with modified oligonucleotides complementary to miR-21, miR-125a, miR-191, miR-210, miR-378 (labeled as miR-422b), miR-423, and miR-638 resulted in significant elevation of Caspase 3/7 activity, indicating an induction of apoptosis.

The caspase 3/7 activity in oligonucleotide-treated samples was compared to the caspase 3/7 activity in untreated control samples. In this way, the induction of apoptosis was measured. The comparison revealed that antisense inhibition of miR-21, miR-125a-5p, miR-191, miR-210, miR-378, miR-423-3p, and miR-638 resulted in increased caspase 3/7 activity (FIG. 3). Thus, modified oligonucleotides complementary to a miR selected from miR-21, miR-125a-5p, miR-191, miR-210, miR-378, miR-423-3p, and miR-638 induced apoptosis in Hep3B cells. Accordingly, such modified oligonucleotides are therapeutic agents for the treatment of HCC.

Example 5: Anti-Tumor Effects of Modified Oligonucleotides In Vivo

To determine the effects of modified oligonucleotides targeted to miRNAs on tumor growth, modified oligonucleotides were evaluated in a mouse model of hepatocellular carcinoma. In this mouse model, HCC-derived cells injected into nude mice form tumors, and modified oligonucleotides are tested for their ability to slow and/or inhibit tumor growth.

To induce tumor formation, a solution containing approximately $5 \times 10^6$ HepG2 cells suspended in Matrigel was injected subcutaneously into nude mice.

The modified oligonucleotides tested in this model included: MOE-modified anti-miR-21, a modified oligonucleotide targeted to miR-21 having a 2'-MOE modification at each sugar, phosphorothioate internucleoside linkages throughout, where each cytosine is a 5-methyl cytosine; and MOE-modified anti-miR-210 having a 2'-MOE modification at each sugar, phosphorothioate internucleoside linkages throughout, where each cytosine is a 5-methyl cytosine. Phosphate-buffered saline (PBS) was used as a control treatment.

Figure 4A:
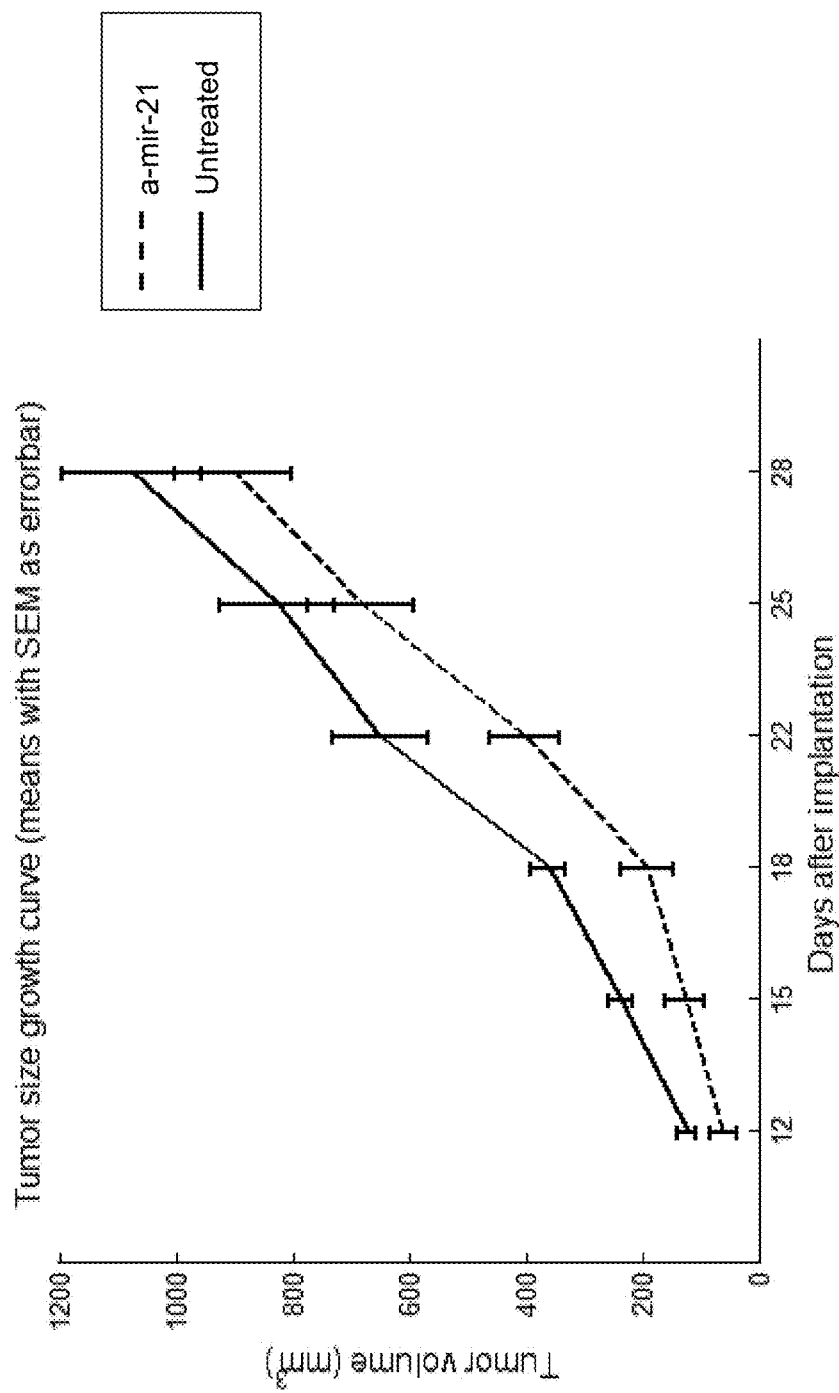
FIGS. 4A and 4B. Reduction of subcutaneous tumor volume in mice treated with modified oligonucleotides. Subcutaneous tumors were induced by the injection of HepG2 cells into nude mice. Treatment with MOE-modified oligonucleotides complementary to miR-21 (FIG. 4A) and miR-210 (FIG. 4B) was shown to reduce tumor volume, relative to saline control treatments.
Figure 4B:
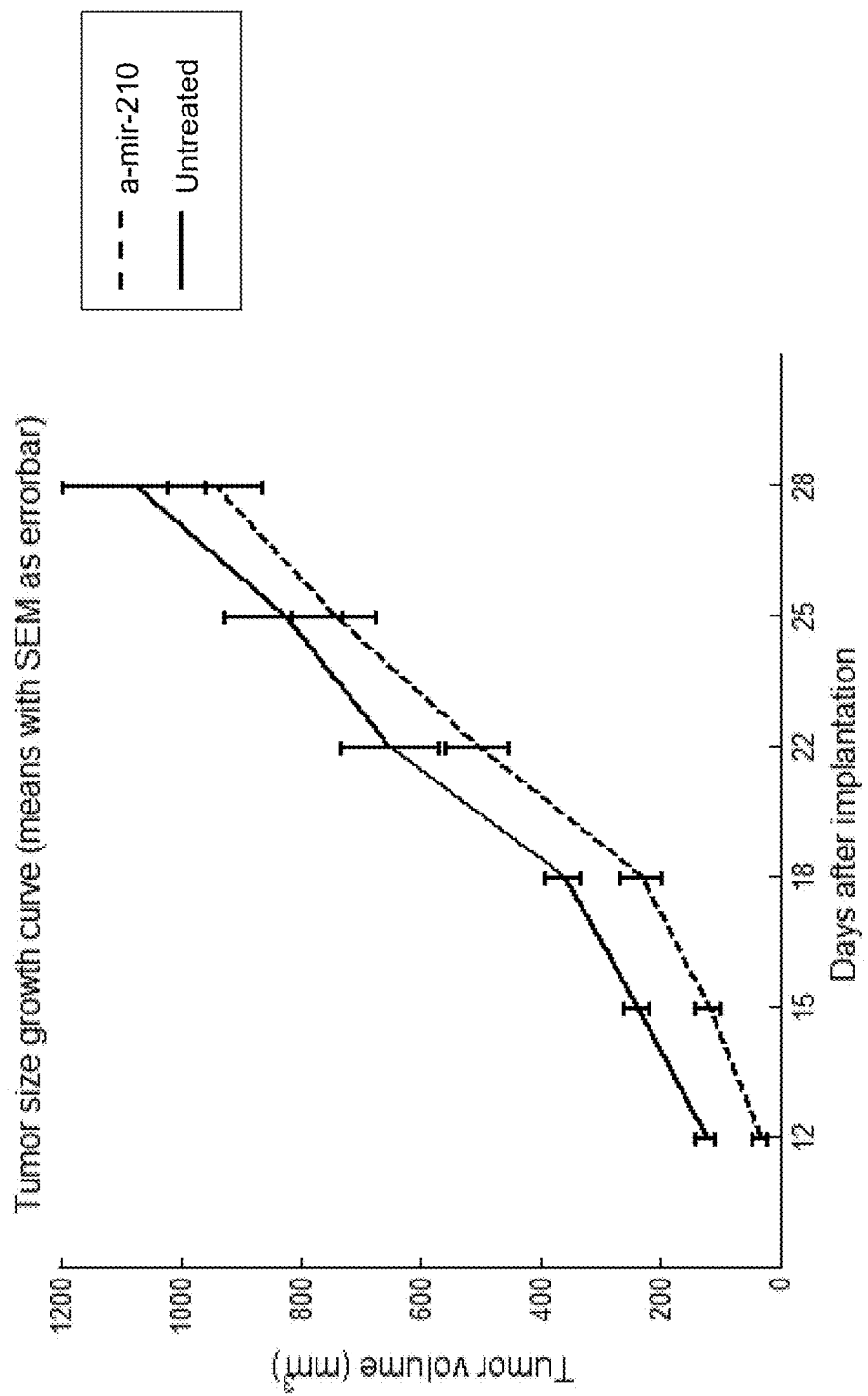

Treatment groups were as follows: (1) control; (2) 50 mg/kg MOE-modified anti-miR21; (3) 50 mg/kg MOE-modified anti-miR-210. Each treatment group contained 10 mice. Mice received intraperitoneal injections of control or modified oligonucleotide beginning on day 4 following tumor induction and continuing every other day for a total of 12 injections (i.e. days 4, 6, 8, 10, 12, 14, 16, 18, 20, 22, 24, and 26). Tumor size was monitored with calipers on days 12, 15, 18, 22, 25, and 28 following tumor induction. Tumor volume was calculated as $(L*W^2)/2$, where L=length (mm) and W=width (mm). Mean tumor volumes for modified oligonucleotide-treated groups were compared to mean tumor volumes for control-treated groups; fold changes in mean tumor volume are shown in Table 7 and FIG. 4. P-values were calculated by t-test.

TABLE 7

| Treatment | Days post tumor induction | Fold change in mean tumor volume | p-value |
|---|---|---|---|
| MOE-modified anti-miR-21 | 12 | 2 | 0.0466 |
| | 15 | 1.9 | 0.0109 |
| | 18 | 1.9 | 0.0067 |
| | 22 | 1.6 | 0.0251 |
| | 25 | 1.2 | 0.2973 |
| | 28 | 1.2 | 0.2785 |
| MOE-modified anti-miR-210 | 12 | 3.9 | 0.0004 |
| | 15 | 2 | 0.0006 |
| | 18 | 1.6 | 0.0113 |
| | 22 | 1.3 | 0.1531 |
| | 25 | 1.1 | 0.4919 |
| | 28 | 1.1 | 0.3646 |

As shown in Table 7, treatment with 50 mg/kg MOE-modified anti-miR-21 resulted in statistically significant smaller tumor size at days 12, 15, 18, and 22 following tumor induction, relative to tumor size in control-treated mice. Reductions in tumor size were also observed at days 25 and 28 following tumor induction. Similarly, treatment with 50 mg/kg MOE-modified anti-miR-210 resulted in statistically significant smaller tumor size at days 12, 15, 18, and 22 following tumor induction, relative to tumor size in control-treated mice. Reductions in tumor size were also observed at days 25 and 28 following tumor induction.

Accordingly, modified oligonucleotides complementary to miR-21 and miR-210 are therapeutic agents for the treatment of HCC.

Example 6: Induction of miR Expression by Activation of the AhR TF by TCDD

Figure 5:
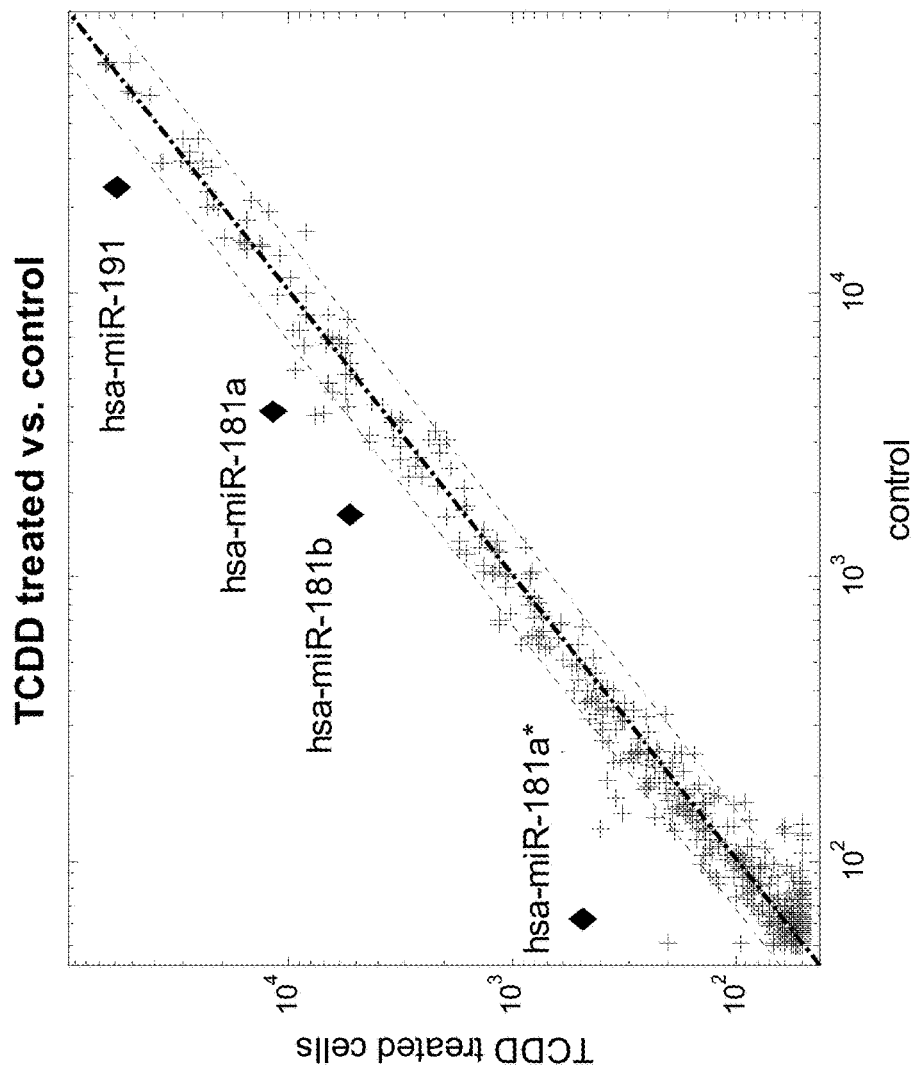
FIG. 5. Median expression value (in log(fluorescence)) of miRNA in HepG2 cells, wherein the X-axis represents cells 48 hours after TCDD treatment, and the Y-axis represents untreated cells. The dotted parallel lines describe a fold change of two in either direction. The middle line describes an identical median expression in both groups of cells.

HCC cells treated with TCDD were studied for miR expression on a microarray (microarray analysis was performed as described in Example 1). As demonstrated in FIG. 5, expression of each of hsa-miR-191, hsa-miR-181a, hsa-miR-181b and hsa-miR-181a* was shown to be elevated more than twofold in TCDD treated cells after 48 hours, compared to untreated cells.

Example 7: Dual-Luciferase Reporter Assay for miR-191

A dual-luciferase reporter assay was prepared to evaluate miR-191 activity. Custom-made 42-nucleotide long complementary oligonucleotides (IDT) were designed to be inserted into the 3' UTR of *renilla* luciferase in a psiCHECK-2 vector (Promega); these oligonucleotides included the reverse complement sequence to selected miRs. Complementary oligonucleotides were annealed, creating NotI and XhoI sticky ends. Sequences included the relevant reverse complement miR sequences and one negative control. These inserts were designed to create miR binding sites, and each insert was cloned in the 3'UTR of *renilla* luciferase in a psiCHECK-2 vector. Clones were verified in three stages: (1) colony PCR, (2) restriction with HindIII utilizing the site added with the insert, and (3) sequencing. SNU423 cells were transfected in triplicates with either one of the vectors or co-transfected with a vector and an ASO using Lipofectamine2000 reagent (Invitrogen, Cat#11668027) Luminescence was assayed 24 and 48 hours later using the Dual-Luciferase Reporter Assay System (Promega, Cat#E1961) according to manufacturer's instructions, on "The Reporter" microplate luminometer (Turner designs). Results were normalized to the constitutively expressed firefly luciferase from the same vector, and presented as the ratio between the various treatments and cells transfected with a non-modified vector.

As indicated in FIG. 6, endogenous hsa-miR-191 (bar a) indeed downregulates the reporter expression, and this effect is almost completely abolished by co-transfection of the reporter vector together with the antisense oligonucleotide inhibiting hsa-miR-191 (bar b). The bar-chart further shows the specificity of the response, since another control ASO could not abolish the miR regulation of the reporter (bar c), and the endogenous miR did not change the expression of the reporter on a control plasmid having an altered 3' UTR but with a non-relevant sequence, with (bar d) or without an ASO (bar e).

Example 8: AhR/Arnt and Regulation of Hsa-miR-191

Transcription factor binding site (TFBS) motifs were searched for at locations +/−1000 bp from the Transcription Start Site of hsa-miR-191. The AhR/Arnt TFBS was predicted at the following location:

| #hg18.tfbs | hg18.tfbsCo | hg18.tfbsCon | hg18.tfbsConsSites.name | hg18.tfbsC | hg18.tfbsC | hg18.tfbsC | hg18.tfbsConsFactors.id |
|---|---|---|---|---|---|---|---|
| Chr3 | 49034918 | 49034937 | V$AHRARNT_02 | + | 2.42 | AhR, Arnt, | P35869, P27540, |

A ChIP (Chromatin Immuno Precipitation) assay was conducted to validate the predicted TFBS and the involvement of this TF in the transcriptional regulation of hsa-miR-191.

The ChIP assay was performed as follows:

HepG2 cells were treated with TCDD at 10 nM concentration. Cells were then fixed when freshly-prepared 11% Formaldehyde Solution was added to the existing media.

Fixation was stopped by adding Glycine Solution. Cells are then scraped off from the culture surface, washed in chilled PBS-Igepal and treated with 1 mM PMSF. Cells are finally centrifuged and pellet is snap-frozen.

The immunoprecipitation is done at Genepathway and the binding of Chromatin to the precipitated TF was quantified by qPCR.

Data values were generated using a standard curve of genomic DNA with known copy numbers. Positive controls are genomic regions containing known binding sites for the factor under investigation, and the negative controls are genomic regions not bound by the factor under investigation. Analysis was done in triplicates.

Input DNA values (unprecipitated genomic DNA) were used to calculate the Primer Efficiency Ratio for every primer pair relative to the primer pair used in the standard curve. The data was presented as the Binding Events Per 1000 Cells for each genomic region tested. These values, which are calculated from the average of the triplicate qPCR values for each test, take into account the amount of chromatin that was immunoprecipitated plus the proportion tested by qPCR, and are normalized for primer efficiency. Also the standard deviations for each test are calculated, which have been normalized in the same way as the test values.

Genpathway has demonstrated that changes in factor binding as low as 1.3× can be reproducibly determined in a variety of biological systems. Therefore, genomic regions showing fold differences of 1.5 or greater are considered significant.

Since TCDD is a known ligand of AhR and activates this TF to induce the expression of CYP1 proteins, TCDD treatment was included as an activator for the TF, and CYP1A1 was chosen as a control gene in the ChIP assay. CYP1A1 has two TFBSs for the AhR/Arnt TF, both which were tested.

As seen in FIG. 7, which summarizes the results of the ChIP assay using a specific antibody for the AhR TF, AhR was found to bind to the promoter of the hsa-miR-191 transcript Similar results were achieved when a ChIP assay was conducted with an Ab against Arnt, which indicates the activity of the heterodimer AhR/Arnt.

The foregoing description of the specific embodiments so fully reveals the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for treating liver cancer comprising administering to a subject in need thereof (i) a compound comprising a modified oligonucleotide consisting of 15 to 30 linked nucleosides, wherein the modified oligonucleotide has a nucleobase sequence that is 100% identical over a region of 8 or more nucleobases of a sequence selected from SEQ ID NOs: 18 and 19 and (ii) at least one additional therapy, wherein the at least one additional therapy is a chemotherapeutic agent.

2. The method of claim 1, wherein the liver cancer is hepatocellular carcinoma.

3. The method of claim 1, wherein the subject is a human.

4. The method of claim 1, wherein the compound consists of a modified oligonucleotide.

5. The method of claim 1, wherein the modified oligonucleotide has a nucleobase sequence comprising at least 15, 16, 17, 18, 19, 20, 21, 22, or 23 contiguous nucleobases of a nucleobase sequence selected from SEQ ID NOs: 18 and 19.

6. The method of claim 1, wherein the modified oligonucleotide has a nucleobase sequence consisting of a nucleobase sequence selected from SEQ ID NOs: 18 and 19.

7. The method of claim 1, wherein at least one internucleoside linkage is a modified internucleoside linkage.

8. The method of claim 1, wherein the modified internucleoside linkage is a phosphorothioate internucleoside linkage.

9. The method of claim 1, wherein each internucleoside linkage is a modified internucleoside linkage.

10. The method of claim 9, wherein the modified internucleoside linkage is a phosphorothioate internucleoside linkage.

11. The method of claim 1, wherein at least one nucleoside comprises a modified sugar.

12. The method of claim 11, wherein each modified sugar is independently selected from a 2'-O-methoxyethyl sugar, a 2'-fluoro sugar, a 2'-O-methyl sugar, or a bicyclic sugar moiety.

13. The method of claim 1, wherein each nucleoside comprises a modified sugar.

14. The method of claim 13, wherein each modified sugar is independently selected from a 2'-O-methoxyethyl sugar, a 2'-fluoro sugar, a 2'-O-methyl sugar, or a bicyclic sugar moiety.

15. The method of claim 1, wherein at least one nucleoside comprises a modified nucleobase.

16. The method of claim 15, wherein the modified nucleobase is a 5-methylcytosine.

17. The method of claim 1 wherein the chemotherapeutic agent is selected from 5-fluorouracil, gemcitabine, doxorubicine, mitomycin c, sorafenib, etoposide, carboplatin, epirubicin, irinotecan, and oxaliplatin.

18. The method of claim 1, wherein the administering results in reduction of tumor size or tumor number, or wherein the administering prevents an increase in tumor size or tumor number.

19. The method of claim 1 wherein the administering prevents or slows metastatic progression.

20. The method of claim 1 wherein the administering extends overall survival time or progression-free survival time of the subject.

21. The method of claim 1 wherein the subject has elevated serum alpha-fetoprotein or elevated serum des-gamma-carboxyprothrombin.

22. The method of claim 21 wherein the administering reduces serum alpha-fetoprotein or serum des-gamma-carboxyprothrombin.

23. The method of claim 1 wherein the modified oligonucleotide has a nucleobase sequence comprising at least 17, 18, 19, 20, or 21 contiguous nucleobases of a nucleobase sequence selected from SEQ ID NOs: 18 and 19.

24. The method of claim 1 wherein the nucleobase sequence of the modified oligonucleotide has no mismatches to the nucleobase sequence of SEQ ID NO: 10.

* * * * *